(12) United States Patent
Fuertinger et al.

(10) Patent No.: US 9,679,111 B2
(45) Date of Patent: Jun. 13, 2017

(54) SYSTEM AND METHOD OF MODELING ERYTHROPOIESIS INCLUDING IRON HOMEOSTASIS

(71) Applicant: Fresenius Medical Care Holdings, Inc., Waltham, MA (US)

(72) Inventors: Doris Helene Fuertinger, Long Island City, NY (US); Franz Kappel, Graz (AT); Peter Kotanko, New York, NY (US); Nathan W. Levin, New York, NY (US); Stephan Thijssen, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 589 days.

(21) Appl. No.: 14/072,506

(22) Filed: Nov. 5, 2013

(65) Prior Publication Data

US 2014/0128791 A1 May 8, 2014

Related U.S. Application Data

(60) Provisional application No. 61/722,503, filed on Nov. 5, 2012.

(51) Int. Cl.
*G06F 19/00* (2011.01)
*A61M 1/14* (2006.01)
*A61M 1/34* (2006.01)

(52) U.S. Cl.
CPC ...... *G06F 19/3437* (2013.01); *G06F 19/3468* (2013.01); *A61M 1/14* (2013.01); *A61M 1/342* (2013.01)

(58) Field of Classification Search
None
See application file for complete search history.

(56) References Cited

U.S. PATENT DOCUMENTS 8,382,696 B2   2/2013  Beiriger et al.
2002/0095258 A1  7/2002  Agur et al.
(Continued)

FOREIGN PATENT DOCUMENTS

WO    WO 2013/036836 A2    3/2013

OTHER PUBLICATIONS

Formanowicz, D., Sackmann, A., Formanowicz, P. & Blazewicz, J. Petri net based model of the body iron homeostasis. Journal of Biomedical Informatics 40, 476-485 (2007).*

(Continued)

*Primary Examiner* — Soren Harward
(74) *Attorney, Agent, or Firm* — Hamilton, Brook, Smith & Reynolds, P.C.

(57) ABSTRACT

A method of adjusting a patient's undesired hematocrit and/or hemoglobin concentration to a value within a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, the model including iron homeostasis, and employing the patient parameters and an initially selected ESA administration regimen in the model to predict the patient's hematocrit and/or hemoglobin concentration at the predetermined time with the initially selected ESA administration regimen. The method then includes administering ESA to the patient with an ESA administration regimen predicted to adjust the patient's hematocrit and/or hemoglobin concentration to the desired range at the predetermined time. The method can be implemented in a hemodialysis system.

6 Claims, 23 Drawing Sheets

(56) References Cited

U.S. PATENT DOCUMENTS

| | | | |
|---|---|---|---|
| 2005/0075274 | A1 | 4/2005 | Willmann et al. |
| 2006/0047538 | A1 | 3/2006 | Condurso et al. |
| 2006/0089592 | A1 | 4/2006 | Kadhiresan et al. |
| 2007/0054331 | A1 | 3/2007 | Kirnasovsky et al. |
| 2007/0178167 | A1 | 8/2007 | Andrijauskas |
| 2009/0171697 | A1 | 7/2009 | Glauser et al. |
| 2010/0169063 | A1 | 7/2010 | Yudkovitch et al. |
| 2011/0004143 | A1* | 1/2011 | Beiriger ............... A61M 1/342 604/6.11 |
| 2011/0184379 | A1 | 7/2011 | Van Antwerp et al. |
| 2012/0150141 | A1* | 6/2012 | Weibel ................ A61M 1/3672 604/500 |
| 2014/0200181 | A1 | 7/2014 | Fuertinger et al. |

OTHER PUBLICATIONS

Franzone, P. C., Paganuzzi, A. & Stefanelli, M. A mathematical model of iron metabolism. Journal of Mathematical Biology 15, 173-201 (1982).*

Kemna, E., Pickkers, P., Nemeth, E., Van Der Hoeven, H. & Swinkels, D. Time-course analysis of hepcidin, serum iron, and plasma cytokine levels in humans injected with LPS. Blood 106, 1864-1866 (2005).*

Babitt, J. L., and Lin, H. Y., "Molecular Mechanisms of Hepcidin Regulation: Implications for the Anemia of CKD," *American Journal of Kidney Diseases*, 55(4):726-741 (Apr. 2010).

Banks, H.T., et al., "A Semigroup Formulation of a Nonlinear Size-Structured Distributed Rate Population Model," *Control and Estimation of Distributed Parameter Systems: Nonlinear Phenomena* (Desch, W., Kappel, F., and Kunisch, K. (eds.), International Series of Numerical Mathematics (ISNM), vol. 118, pp. 1-19, Birkhäuser, Basel (1994).

Feagan, C.J., et al., "Erythropoietin With Iron Supplementation to Prevent Allogenic Blood Transfusion in Total Hip Joint Arthroplasty," *Annals of Internal Medicine*, 133:845-854 (2000).

Fowler, W.M., and Barner, A.P., "Rate of Hemoglobin Regeneration in Blood Donors," *J. Amer. Medical Ass.*, 118:421-427 (1942).

Franzone, P.C., et al., "A Mathematical Model of Iron Metabolism," *Journal of Mathematical Biology*, 15:173-201 (1982).

Fuertinger, D.H. and Kappel, F., "A Numerical Method for Structured Population Equations Modeling Control of Erythropoiesis" $1^{st}$ IFAC Workshop on: Control of Systems Governed by Partial Differential Equation, Paris France, 4 pages (2013).

Fuertinger, D.H. and Kappel, F., A Parameter Identification Technique for Structured Population Equations Modeling Erythropoiesis in Dialysis Patients, Proceeding of the World Congress on Engineering and Computer Science 2013, Oct. 23-25, 2013 San Fancisco, CA, vol. 11:940-944.

Jaspan, D., "Erythropoietic Therapy: Cost Efficiency and Reimbursement," *Amer. J. Health Syst. Pharm.*, 65:19-29 (2007).

Kaufman, J.S., et al., "Subcutaneous Compared with Intravenous Epoetin in Patients Receiving Hemodialysis," *The New England Journal of Medicine*, 339(9):578-583 (1998).

Messana, J.M., "Association of Quarterly Average Achieved Hematocrit with Mortality in Dialysis Patients: A Time-Dependent Comorbidity-Adjusted Model," *American Journal of Kidney Diseases*, 53(3):503-512 (Mar. 2009).

Nooney, G.C., "An Erythron-Dependent Model of Iron Kinetics," *Biophysical Journal*, 6:601-609 (1965).

Nooney, G.C., "Iron Kinetics and Erythron Development," *Biophysical Journal*, 5:755-765 (1965).

Ponka, P., "Tissue Specific Regulation of Iron Metabolism and Heme Synthesis: Distinct Control Mechanisms in Erythroid Cells", *Blood*, 89:1-25 (1997).

Pottgiesser, T., et al., "Recovery of Hemoglobin Mass After Blood Donation," *Transfusion*, 48:1390-1397 (2008).

International Search Report and Written Opinion of the International Searching Authority for PCT/US2012/054264, "System and Method of Modeling Erythropoiesis and Its Management", date of mailing Aug. 14, 2013.

Notification Concerning Transmittal of International Preliminary Report on Patentability for PCT/US2012/054264, "System and Method of Modeling Erythropoiesis and Its Management", date of mailing Mar. 20, 2014.

Ackleh, A.S., et al., "A finite difference approximation for a coupled system of nonlinear size-structured population," *Nonlinear Analysis*, 50:727-748, 2002.

Ackleh, A.S., et al., "A structured erythropoiesis model with non-linear cell maturation velocity and hormone decay rate," *Mathematical Biosciences*, 204:21-48 (2006).

Adimy, M., et al., "Modeling hematopoiesis mediated by growth factors with applications to periodic hematological diseases," *Bulletin of Mathematical Biology*, 68:2321-2351 (2005).

Albert, S. N., "Blood Volume Measurement," In: *Nuclear Medicine In Vitro*. 2 ed. (PA: JB Lippincott Co.), (1983).

Alfrey, C. P. and Fishbane, S., "Implications of Neocytolysis for Optimal Management of Anaemia in Chronic Kidney Disease," *Nephron Clinical Practice*, 106:149-156 (2007).

Banks, H.T., et al., "Modelling and Optimal Regulation of Erythropoiesis Subject to Benzene Intoxication," *Mathematical Biosciences and Engineering*, 1:15-48 (Dec. 20, 2003).

Barosi, G., et al., "Erythropoiesis and Iron Kinetics," *British Journal of Haematology*, 40:3 503-504, Nov. 1978.

Belair, J., et al., "Age-Structured and Two-Delay Models for Erythropoiesis," *Mathematical Biosciences*, 128:317-346 (1995).

Bernard, P. J., "Measurement of Red-Cell and Plasma Volumes," *Nouv Rev Fr Hematol*, 36(2):155-157 (1994).

Bernard, P. J., "International Committee for Standardization in Haematology: Recommended Methods for Measurement of Red-Cell and Plasma Volume", *J Nucl Med* 21(8):793-800 (1980).

Besarab, A., et al., "The Effects of Normal as Compared with Low Hematocrit Values in Patients With Cardiac Disease Who Are Receiving Hemodialysis and Epoetin," *The New England Journal of Medicine*, 339:584-590 (Aug. 27, 1998).

Bratosin, D., et al., "Programmed Cell Death in Mature Erythrocytes: a Model for Investigating Death Effector Pathways Operating in the Absence of Mitochondria," *Cell Death Differentiation*, 8:1143-1156, (2001).

Chan, R. Y., et al., "Regulation of Transferrin Receptor MRNA Expression. Distinct Regulatory Features in Erythroid Cells," *European Journal of Biochemistry*, 220:683-692 (1994).

Chang, C-C., et al., "Changes of Red Blood Cell Surface Markers in a Blood Doping Model of Neocytolysis," *Journal of Investigative Medicine*, 57:650-654 (Jun. 2009).

Collins, A. J., et al., "Epoetin Alfa use in Patients With ESRD: An Analysis of Recent Use Prescribing Patterns and Hemoglobin Outcomes," *American Journal of Kidney Diseases*, 46:481-488 (2005).

Crauste, F., et al., "Mathematical study of feedback control roles and relevance in stress erythropoiesis," *Journal of Theoretical Biology*, 263(3):303-316(2010).

Crauste, F., et al., Adding self-renewal in committed erythroid progenitors improves the biological relevance of a mathematical model of erythropoiesis, *Journal of Theoretical Biology*, 250:322-338 (2007).

Crepaldi, C., et al., "Iron Management in Hemodialysis Patients: Optimizing Outcomes in Vicenza, Italy," *Hemodialysis International*, 7(3):216-221 (2003).

Crichton, R., "Iron Metabolism" In: *Molecular Mechanisms to Clinical Consequences*, (NY: J. Wiley), (2009).

Demin, I., et al., "A multi-scale model of erythropoiesis," *Journal of Biological Dynamics*, 4(1):59-70 (2010).

Drüeke, T. B., et al., "Normalization of Hemoglobin Level in Patients with Chronic Kidney Disease and Anemia," *The New England Journal of Medicine*, 355(20):2071-2084 (Nov. 16, 2006).

Finch, C. A., "Erythropoiesis, Erythropoietin, and Iron," *Blood. The Journal of American Society of Hematology*, 60(6): 1241-1246, (1982).

Finch, S., et al., "Iron Metabolism. Hematopoiesis Following Phlebotomy. Iron as a Limiting Factor," *The Journal of Clinical Investigation*, 29:1078-1086 (1950).

Fisher, J.W., "Erythropoietin: Physiology and pharmacology update," *Experimental Biology and Medicine*, 28:1-24 (2003).

(56) References Cited

OTHER PUBLICATIONS

Fleming, M. D., "The regulation of hepcidin and its effects on systemic and cellular iron metabolism," *J. Amer. Soc. Hematology*, pp. 151-158 (2008).

Foller, M., et al., "Enhanced susceptibility to suicidal death of erythrocytes from transgenic mice overexpressing erythropoietin," *American Journal of Physiology—Regulatory, Integrative and Comparative Physiology*, 293:R1127-R1134 (2007).

Foley, R. N., et al., "Erythropoietin therapy, hemoglobin targets, and quality of life in healthy hemodialysis patients: A randomized trial," *Clinical Journal of the American Society of Nephrology*, 4:726-733 (2009).

Fuertinger, D. H.,. *A model for erythropoiesis*. PhD thesis, University of Graz, Austria, 2012.

Fuertinger, D. H., et al., "A Model of Erythropoiesis in Adults with Sufficient Iron Availability," *Journal of Mathematical Biology*, 66(6):1209-1240 (2013).

Fuertinger, D. H. and Kappel, F., "A Parameter Identification Technique for Structured Population Equations Modeling Erythropoieses in Dialysis Patients," *WCECS*, II:23-25 (2013).

Föller, M., et al., "Erthrocyte programmed cell death," *IUBMB Life*, 60:661-668 (2008).

Gifford, S. C., et al., "A detailed study of time-dependent changes in human red blood cells: from reticulocyte maturation to erythrocyte senescence," *British Journal of Haematology*, 135:395-404 (2006).

Goodnough, L. T., "The role of iron in erythropoiesis in the absence and presence of erythropoietin therapy," *Nephrology Dialysis Transplantation*, 17:14-18 (2002).

Goodnough, L. T., et al., "Detection, evaluation and management of preoperative anaemia in the elective orthopaedic surgical patient: NATA guidelines," *British Journal of Anaesthesia*, 106(1):13-22 (2011).

Goodnough, L.T., et al., "Detection, evaluation, and management of iron-restricted erythropoiesis," *Blood*, 116:4754-4761 (2010).

Greer, J. P., In: "Wintrobe's Clinical Hematology," *12th edition, vol. 1*. (Lippincott Williams & Wilkins), (2009).

Jandl, J. H., In "Blood: Textbook of Hematology," $2^{nd}$ Ed. Little, Brown and Company, (1996).

Kalantar-Zadeh, K., et al., "Time-dependent associations between iron and mortality in hemodialysis patients," *Journal of American Society of Nephrology*, 16:3070-3080 (2005).

Lang, F., et al,. "Eryptosis, a Window to Systemic Disease," *Eryptosis, Cellular Physiology and Biochemistry*, 22:373-380 (2008).

Lang, F., et al., "Erythrocyte ion channels in regulation of apoptosis," *Advances in Experimental Medicine and Biology*, 559:211-217 (2004).

Lang, F., et al., "Mechanisms and significance of eryptosis," *Antioxidants & Redox Signaling*, 8:1183-1192, (2006).

Lichtman, M.A., E. Beutler, E., Kipps, T.J., Seligsohn, U., Kaushansky, K., and Prchal, J.T. (editors), "," *Williams Hematology, 7th edition*, (NY: McGraw-Hill), (2005).

Loeffler, M., et al., "Mathematical model of erythropoiesis in mice and rats, Part 1, Structure of the model," *Cell and Tissue Kinetics*, 22:13-30 (1989).

Loria, A., et al., "Red cell life span in iron deficiency anaemia ," *Br J Haematol*, 13(3):294-302 (1967).

Mahaffy, J.M., et al., "An age-structured model for erythropoiesis following a phlebotomy. Technical Report CRM-2598," Department of Mathematical Sciences, San Diego State University, San Diego, CA 92182-0314, Feb. 1999.

Mahaffy, J.M., et al., "Hematopoietic model with moving boundary condition and state dependent delay: Applications in erythropoiesis," *Journal of Theoretical Biology*, 190:135-146 (1998).

Myssina, S., et al , "Inhibition of erythrocyte cation channels by erythropoietin," *Journal of American Society of Nephrology*, 14:2750-2757 (2003).

Nadler, S. B., et al., "Prediction of blood volume in normal human adults," *Surgery*, 51:224-232 (1962).

Nemeth, E., et al., "Hepcidin Regulates Cellular Iron Efflux by Binding to Ferroportin and Inducing Its Internalization" *Science*, 306:2090-2093 (2004).

Parfrey, P. S., "Target Hemoglobin Level for EPO Therapy in CKD," *American Journal of Kidney Diseases*, 47(1):171-173 (2006).

Pfeffer, M. A., et al., "A Trial of Darbepoetin Alfa in Type 2 Diabetes and Chronic Kidney Disease," *The New England Journal of Medicine*, 361(21):2019-2032 (2009).

Phurrough, S, et al., "Proposed Coverage Decision Memorandum for the Use of Erythropoiesis Stimulating Agents in Cancer and Related Neoplastic Conditions"; Centers for Medicare and Medicaid Services; Administrative File: CAG #000383N; May 14, 2007.

Polenakovic, M. and Sikole, A., "Is erythropoietin a survival factor for red blood cells?," *Journal of American Society of Nephrology*, 7:1178-1182 (1996).

Ponka, P. and Lok, C. N., "The transferring receptor: role in health and disease," *The International Journal of Biochemistry & Cell Biology*, 31:1111-1137 (1999).

Rice, L., and Alfrey, C.P., "The negative regulation of red cell mass by neocytolysis: Physiologic and pathophysiologic manifestations," *Cellular Physiology and Biochemistry*, 15:245-250 (2005).

Rice, L., et al., "Neocytolysis contributes to the anemia of renal disease," *American Journal of Kidney Diseases*, 33:59-62 (1999).

Rice, L., et al., "Neocytolysis on descent from altitude: A newly recognized mechanism," *Annals Internal Medicine*, 134:652-656 (2001).

Roeder, I. and Loeffler, M., "A novel dynamic model of hematopoietic stem cell organization based on the concept of within-tissue plasticity," *Experimental Hematology*, 30:853-861 (2002).

Roeder., I., "Quantitative stem cell biology: Computational studies in the hematopoietic system," *Current Opinion in Hematology*, 13:222-228 (2006).

Schaefer, R. M. and Schaefer, L. "Iron monitoring and supplementation: How do we achieve the best results?," *Nephrology Dialysis Transplantation*, 13:9-12 (1998).

Schmidt, J. A., et al., "Control of erythroid differentiation: Possible role of the transferrin cycle," *Cell*, 46:41-51 (1986).

Schwartz, A. B., et al., "One year of rHuEPO therapy prolongs RBC survival may stabilize RBC membranes despite natural progression of chronic renal failure to uremia and need for dialysis," *ASAIO Transactions*, 36:M691-M696 (1990).

Singh, A. K., et al., "Correction of Anemia with Epoetin Alfa in Chronic Kidney Disease," *The New England Journal of Medicine*, 355(20):2085-2098 (2006).

Steadman's Medical Dictionary, $26^{th}$ Edition, Williams & Wilkins, 1995.

Stefanelli, M., et al., "Quantitation of Reticuloendothelial Iron Kinetics in Humans," *The American Journal of Physiology*, 247:842-849 (1984).

Strippoli, G. F. M., et al., "Hemoglobin Targets for the Anemia of Chronic Kidney Disease: A Meta-analysis of Randomized, Controlled Trials," *Journal of the American Society of Nephrology*, 15:3154-3165 (2004).

Strocchi, A., et al., "A simple carbon monoxide breath test to estimate erythrocyte turnover," *J Lab Clin Med*, 120(3):392-399 (1992).

Udden, M. M., et al., "Decreased production of red blood cells in human subjects exposed to microgravity," *The Journal of Laboratory and Clinical Medicine*, 125:442-449 (1995).

Volkova, N., and Arab, L., "Evidence-Based Systematic Literature Review of Hemoglobin/Hematocrit and All-Cause Mortality in Dialysis Patients," *Am J Kidney Dis*, 47(1):24-36 (2006).

Volpert, V., et al., "Spatial distribution of cell populations in the process of erythropoiesis," *IEJPAM*, 1(2):143-161 (2010).

Werre, J. M., et al., "The red cell revisited. Matters of life and death," *Cellular and Molecular Biology*, 50 (2):139-145 (2004).

Wichmann, H.E., et al., "A mathematical model of erythropoiesis in mice and rats. Part 2. Stimulated erythropoiesis," *Cell and Tissue Kinetics*, 22:31-49 (1989).

(56) References Cited

OTHER PUBLICATIONS

Willekens, F. L., et al., "Hemoglobin loss from erythrocytes in vivo results from spleen-facilitated vesiculation," *Blood*, 101:747-751 (2003).

Willekens, F. L., et al., "Quantification of loss of haemoglobin components from the circulating red blood cell in vivo," *European Journal of Haematology*, 58:246-250 (1997).

Wish, J. B., "Assessing iron status: Beyond serum ferritin and transferrin saturation," *Clinical Journal of the American Society of Nephrology*, 1:S4-S8 (2006).

Wrighting, D. M. and Andrews, N. C., "Iron Homeostasis and Erythropoiesis," *Current Topics in Developmental Biology*, 82:141-159 (2008).

Wu, H., et al., "Generation of committed erythroid BFU-E and CFU-E progenitors does not require erythropoietin or the erythropoietin receptor," *Cell*, 83(1):59-67 (1995).

Wulff, H., et al., "A mathematical model of erythropoiesis in mice and rats. Part 3: Suppressed erythropoiesis," *Cell and Tissue Kinetics*, 22:51-61 (1989).

Zwaal, R. F., et al., "Surface exposure of phosphatidylserine in pathological cells," *Cellular and Molecular Life Sciences*, 62:971-988 (2005).

Pollak, V., et al. "The importance of iron in long-term survival of maintenance hemodialysis patients treated with epoetim-alfa and intravenous iron: analysis of 9.5 years of prospectively collected data", BMC Nephrology, Feb. 26, 2009.

Demin, I., et al., "Spatial Distribution of Cell Populations in the Processes of Erythropoiesis", *International Electronic Journal of Pure and Applied Mathematics*, 1(2): 143-161 (2010).

Fishbane, S. and Nissenson, A.R., "The New FDA Label for Erythropoietin Treatment: How Does it Affect Hemoglobin Target?", *Kidney International*, 72:806-813 (2007).

Krzyzanski, W., et al., "Pahrmacokinetic and Pharmacodynamic Modeling of Recombinant Human Erythropoietin After Multiple Subcutaneous Doses in Healthy Subjects", *European Journal of Pharmaceutical Sciences*, 26:295-306 (2005).

Krzyzanski, W., et al., "Basic Pharmacodynamic Models for Agents that Alter the Lifespan Distribution of Natural Cells", *J Pharmacokinet Pharmctcodyn*, 35:349-377 (2008).

Nordenson, N.J., "Red Blood Cell Indices." In The Gale Encyclopedia of Medicine, Second Ed, vol. 4, J.L. Longe, ed (Gale Group/Thomson Learning), pp. 2837-2939 (2002).

Non-Final Office Action for U.S. Appl. No. 14/343,464, "System and Method of Modeling Erythropoiesis and Its Management", dated May 23, 2016.

\* cited by examiner

| Parameter | Meaning |
| --- | --- |
| $\beta^p$ | proliferation rate for BFU-E cells |
| $\beta^q$ | proliferation rate for CFU-E cells |
| $\beta^r$ | proliferation rate for erythroblasts |
| $\mu^p_{max}$ | maximal maturity for BFU-E cells |
| $\mu^q_{min}$ | minimal maturity for CFU-E cells |
| $\mu^q_{max}$ | maximal maturity for CFU-E cells |
| $\mu^r_{min}$ | minimal maturity for erythroblasts |
| $\mu^r_{max}$ | maximal maturity for erythroblasts |
| $h^r_{min}$ | minimal hemoglobin content for erythroblasts |
| $h^r_{max}$ | maximal hemoglobin content for erythroblasts |
| $\tau^r_{min}$ | minimal number of TfR expressed on erythroblasts |
| $\tau^r_{max}$ | maximal number of TfR expressed on erythroblasts |
| $\mu^s_{min}$ | minimal maturity for marrow reticulocytes |
| $\mu^s_{max}$ | maximal maturity for marrow reticulocytes |
| $h^s_{min}$ | minimal hemoglobin content for reticulocytes |
| $h^s_{max}$ | maximal hemoglobin content for reticulocytes |
| $\tau^s_{min}$ | minimal number of TfR expressed on reticulocytes |
| $\tau^s_{max}$ | maximal number of TfR expressed on reticulocytes |
| $\alpha^m_{rand}$ | intrinsic mortality rate for erythrocytes |
| $a_1, b_1, c_1, k_1$ | constants for the sigmoid apoptosis rate for CFU-E cells |
| $a_2, b_2, c_2, k_2$ | constants for the sigmoid maturation velocity for marrow reticulocytes |
| $d_1$ | rate constant for transferrin to bind to its receptor |
| $d_2$ | rate constant with which hemoglobin is synthesized after transferrin bound to the TfR |
| $a_3, b_3, c_3, h^r_*$ | constants for the function describing the change of the number of TfR expressed on erythroblasts and reticulocytes |
| $b_4, h^{}, \mu^{}$ | constants for the apoptosis rate for erythroblasts |
| $a_5, b_5, c_5, k_5$ | constants for the sigmoid maturation velocity for reticulocytes |
| $b_6, c_6, \mu^m_x$ | constants for the corpuscular hemoglobin decay in erythrocytes |
| $\mu^{m,n}_{min}$ | lower bound of erythrocytes which are possibly exposed to neocytolysis |
| $\mu^{m,n}_{max}$ | lower bound of erythrocytes which are possibly exposed to neocytolysis |
| $\mu_{max}$ | maximal life span for erythrocytes |
| $c_E$ | constant in the mortality rate for erythrocytes |
| $\tau_E$ | EPO threshold for neocytolysis |
| $a_7, b_7, c_7, k_7$ | constants for the sigmoid function governing the release of EPO by the kidneys |
| $c^{end}_{deg}$ | degradation rate of EPO released by the kidneys |
| $c^{ex}_{deg}$ | degradation rate of administered EPO (Epoetin alfa) |
| $S_0$ | number of cells committing to the erythroid lineage |
| $TBV$ | total blood volume |
| $k_{ij}$ | transfer rates from iron compartment $i$ to iron compartment $j$ |
| $a_{iv}$ | the amount of iron administered intravenously |
| $a_{gastro}$ | the amount of iron in the duodenum |
| $a_8, b_8, c_8, k_8$ | constants for the sigmoid function governing the flow rate from the duodenum into the plasma compartment |
| $a_H, b_H, c_H, k_H$ | constants for the sigmoid function governing the release of hepcidin by the liver |
| $c_U, c_{a_5}, c_i$ | constants for the auxiliary equation used in the sigmoid function governing the release of hepcidin by the liver |
| $c^H_{deg}$ | degradation rate of hepcidin |
| $a_9, b_9, c_9, k_9$ | constants for the sigmoid function describing the flow rate from the macrophages into the plasma compartment |
| $a_{10}, b_{10}, c_{10}, k_{10}$ | constants for the sigmoid function governing the flow rate from the storage into the plasma compartment |

FIG. 9

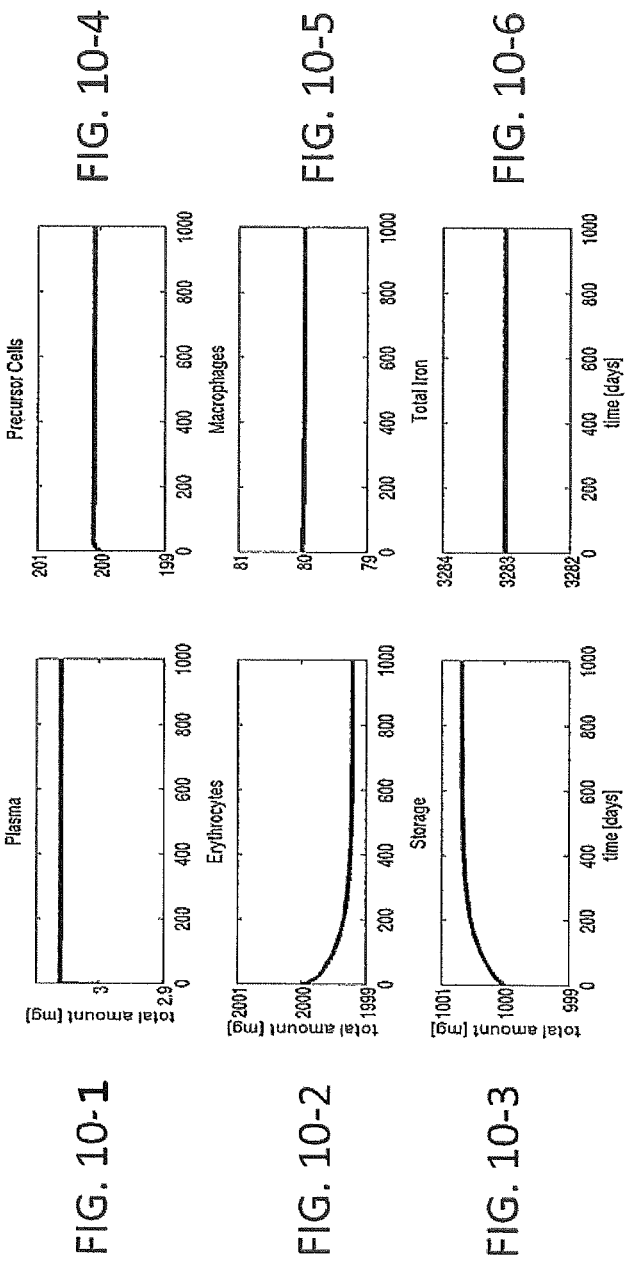

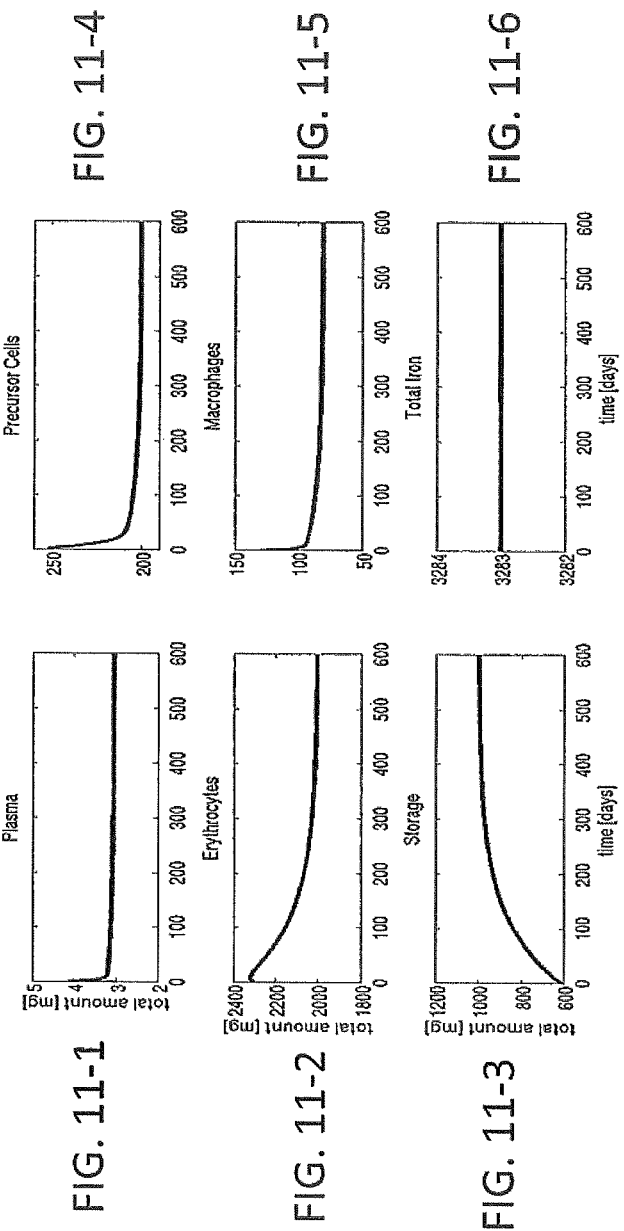

SYSTEM AND METHOD OF MODELING ERYTHROPOIESIS INCLUDING IRON HOMEOSTASIS

RELATED APPLICATION(S)

This application claims the benefit of U.S. Provisional Application No. 61/722,503, filed on Nov. 5, 2012. The entire teachings of this application are incorporated herein by reference.

BACKGROUND OF THE INVENTION

Red blood cells (erythrocytes) are essential for the transport of oxygen through the body. An understanding of the regulation of red blood cell production, called erythropoiesis, is important for the treatment of patients in a variety of clinical situations. Patients that are scheduled for elective surgery, such as hip or transplant surgery, can be prescribed an erythropoiesis stimulating agent (ESA) to compensate for the expected loss of blood, thus obviating the need for allogenic blood transfusions by raising the patient's hematocrit and/or hemoglobin concentration to a desired range at the predetermined time, in expectation of the surgery. Erythropoiesis stimulating agents (ESAs), including recombinant human erythropoietin, exert hematological effects analogous to the hormone erythropoietin (EPO), which is released into the blood stream by the kidneys based on a negative feedback mechanism that reacts to the partial pressure of oxygen in the blood. ESA treatment regimens are also prescribed for patients who suffer from insufficient erythropoiesis, such as cancer patients recovering from the effects of chemotherapy, and chronic kidney disease patients whose kidneys can no longer produce sufficient amounts of EPO. The dose and frequency of administration of an ESA treatment regimen are often determined based on the prior experience of the physician and on established guidelines, because predictive models of erythropoiesis under an ESA treatment regimen are not readily available.

Therefore, there is a need for a reliable predictive model of erythropoiesis under various ESA treatment regimens.

SUMMARY OF THE INVENTION

A model for erythropoiesis in humans is provided that is based on structured population models for the different cell stages in development, from stem cells in bone marrow to erythrocytes in the blood stream.

In one embodiment, a method of adjusting a patient's hematocrit and/or hemoglobin concentration to a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, the model including iron homeostasis, and employing the patient parameters and an initially selected ESA administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, the method includes employing the model with one or more different ESA administration regimens until the model predicts that the patient's hematocrit and/or hemoglobin concentration will be in the desired range at the predetermined time. The method then includes administering ESA to the patient with the ESA administration regimen predicted to adjust the patient's hematocrit and/or hemoglobin concentration to the desired range at the predetermined time. The ESA administration regimen can include iron administration, and the model includes iron homeostasis with iron administration, and modeling the influence of iron homeostasis on erythropoiesis. The patient parameters can include the starting hemoglobin concentration in the patient's blood, the total blood volume of the patient, the lifespan of red blood cells (RBCs) of the patient, the mean corpuscular volume of the RBCs, the rate of neocytolysis in the patient's blood, the distribution of cell hemoglobin content in the patient's blood, the distribution of red blood cell size, iron storage level of the patient, C-reactive protein (CRP) levels, interleukin-6 (IL-6) levels, and the hepcidin levels of the patient. The predetermined time can be, for example, in a range of between about 5 days and about 200 days into the ESA administration regimen. In some embodiments, the patient undergoes a medical procedure prior, during, or after initiation of an ESA administration regimen, including medical procedures such as blood donation, surgery, and dialysis, or any combination thereof. For dialysis patients, the desired hematocrit can be, for example, in the range of between about 28 percent and about 36 percent and the desired hemoglobin concentration can be, for example, in a range of between about 9.5 g/dL and about 12 g/dL.

In yet another embodiment, a computer system for adjusting a patient's hematocrit and/or hemoglobin concentration to a desired range at a predetermined time with an erythropoiesis stimulating agent (ESA) regimen includes a user input means for determining patient parameters from a user, a digital processor coupled to receive determined patient data from the input means, wherein the digital processor executes a modeling system in working memory, and an output means coupled to the digital processor, the output means provides to the user the patient's hematocrit and/or hemoglobin concentration under each ESA administration regimen at the predetermined time. The modeling system employs the patient parameters and an initially selected ESA administration regimen in the model to predict the patient's hematocrit and/or hemoglobin concentration at the predetermined time with the initially selected ESA administration regimen, the model including iron homeostasis. Optionally, if the patient's hematocrit and/or hemoglobin concentration is not predicted by the model to be in the desired range at the predetermined time, the model can be employed with one or more different ESA administration regimens until the model predicts that the patient's hematocrit and/or hemoglobin concentration will be in the desired range at the predetermined time.

In still another embodiment, a method of determining an ESA administration regimen to bring a patient's hematocrit and/or hemoglobin concentration into a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, the model including iron homeostasis, and employing patient parameters and an initially selected ESA administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, the method includes employing the model with one or more different ESA administration regimens until the model predicts that the patient's hematocrit and/or hemoglobin concentration will be in the desired range at the predetermined time. The method then can include administering ESA to the patient with the ESA administration regimen predicted to adjust the patient's hematocrit and/or hemoglobin concentration to the desired range at the predetermined time.

In another embodiment, a method of confirming that an ESA administration regimen is maintaining a patient's hematocrit and/or hemoglobin concentration within a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, the model including iron homeostasis, and employing patient parameters and an initially selected ESA administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, the method includes employing the model with one or more different ESA administration regimens until the model predicts that the patient's hematocrit and/or hemoglobin concentration will be in the desired range at the predetermined time. The method then can include administering ESA to the patient with the ESA administration regimen predicted to adjust the patient's hematocrit and/or hemoglobin concentration to the desired range at the predetermined time.

In yet another embodiment, a hemodialysis system includes a hemodialysis machine including a blood pump, a modular drug delivery device comprising at least one erythropoiesis stimulating agent (ESA) pump, at least one iron replacement product pump, at least one ESA vial holder, and at least one iron replacement product vial holder, and a housing to which the blood pump and the modular drug delivery device are secured.

The hemodialysis system further includes a blood line set comprising multiple blood lines and a drip chamber in fluid communication with the multiple blood lines, at least one of the blood lines being connected to the drip chamber, the blood line set being connected to the blood pump in a manner such that, when the blood line set is connected to a patient and the blood pump is operated, blood of the patient is passed through the blood line set. Additionally, the hemodialysis system includes a drug administration fluid line set comprising multiple drug lines, at least two of the drug lines of the drug line set being connected to the drip chamber of the blood line set, and the drug line set being connected to the at least one ESA pump and the at least one iron replacement product pump in a manner such that, when the drug line set is fluidly connected to an ESA vial contained in the at least one ESA vial holder and to an iron replacement product vial contained in the at least one iron replacement product vial holder, and the at least one ESA pump and the at least one replacement product pump are operated, ESA and iron replacement product are delivered from the ESA vial and the iron replacement vial, respectively, to the drip chamber of the blood line set via the drug line set.

The hemodialysis system is controlled by a control unit configured to adjust the patient's undesired hematocrit and/or hemoglobin concentration to a value within a desired range at a predetermined time by i) employing a model for predicting the patient's hematocrit and/or hemoglobin concentration at a predetermined time, the model including iron homeostasis, and by ii) operating the blood pump, the at least one ESA pump, and the at least one iron replacement product pump to deliver blood, ESA, and iron replacement product to the drip chamber via the at least one of the blood lines connected to the drip chamber and the at least two of the drug lines connected to the drip chamber, according to an ESA administration regimen predicted to adjust the patient's hematocrit and/or hemoglobin concentration to a value within the desired range at the predetermined time.

This invention has many advantages, including the achievement of an ESA regimen needed for a desired hematocrit and/or hemoglobin concentration for a patient, thereby, on the one hand, alleviating insufficient erythropoiesis, and, on the other hand, preventing excessively high ESA dose levels that raise the patient's blood pressure and increase the patient's risk of stroke and cardiovascular disease.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 9 is a list of definitions for model parameters for the equations set forth in Section 4.

FIGS. 10-1-6 are graphs of model results of the total amount [mg] of iron as a function of time [days] of FIG. 10-1: Plasma, FIG. 10-2: Erythrocytes, FIG. 10-3: Storage, FIG. 10-4: Precursor Cells, FIG. 10-5: Macrophages, FIG. 10-6: Total iron for the iron model for a 70 kg man started near the steady state.

FIGS. 11-1-6 are graphs of model results of the total amount [mg] of iron as a function of time [days] of FIG. 11-1: Plasma, FIG. 11-2: Erythrocytes, FIG. 11-3: Storage, FIG. 11-4: Precursor Cells, FIG. 11-5: Macrophages, FIG. 11-6: Total Iron for the iron model for a 70 kg man started with increased amounts of iron incorporated in hemoglobin and decreased storage.

DETAILED DESCRIPTION OF THE INVENTION

Figure 1:
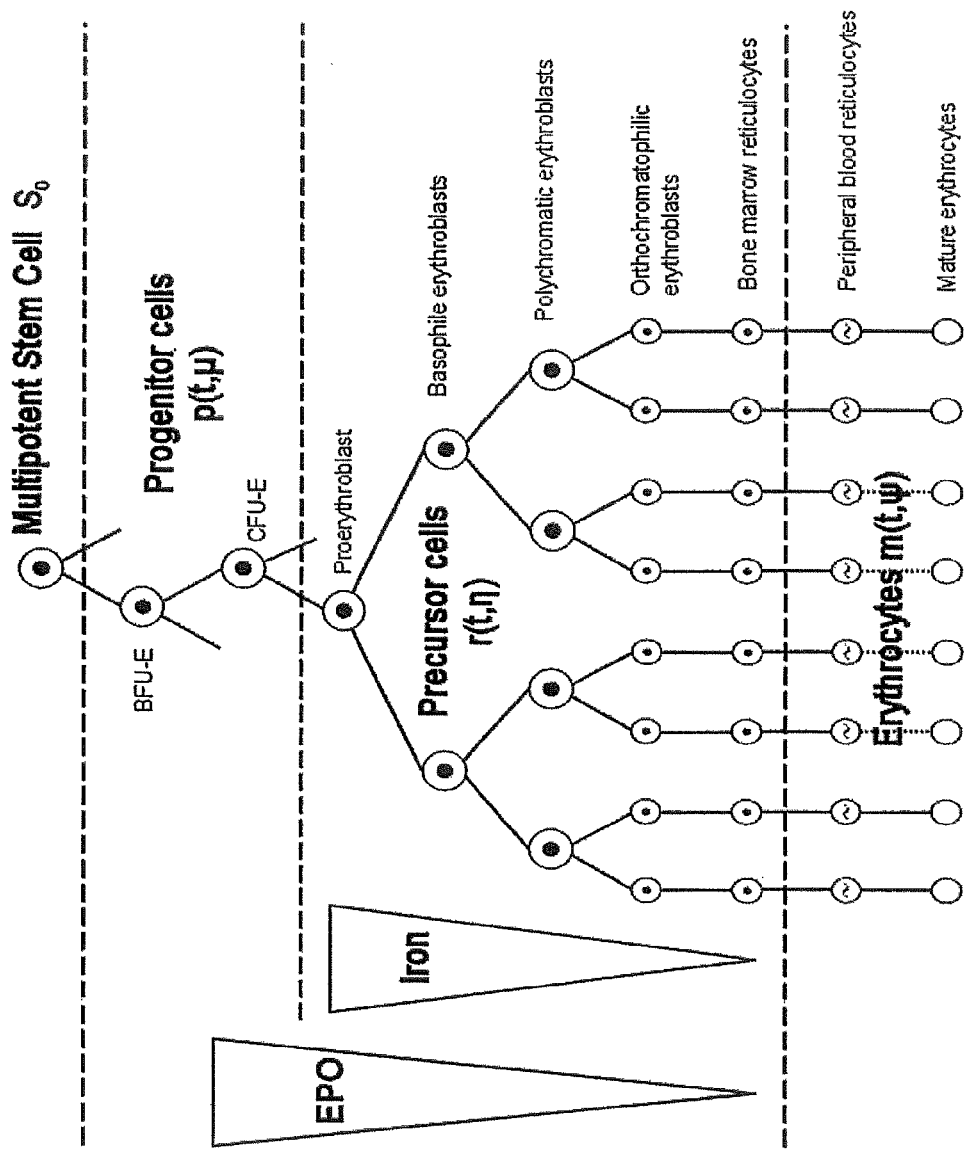
FIG. 1 is a schematic illustration of the influence of EPO and iron on cell stages during erythropoiesis in a human being.

Red blood cells (erythrocytes) are essential for the distribution of oxygen through the body to organs and tissues. They take up oxygen in the lungs and deliver it to tissues while squeezing through the capillaries. To fulfill this task properly, they are highly specialized. For instance, being shaped like biconcave disks optimizes the oxygen exchange. Furthermore, the nuclei, organelles, and mitochondria have been expelled in earlier developmental stages, and therefore more space for hemoglobin, the molecule which oxygen binds to, is available. Erythrocytes are very deformable and can therefore pass capillaries half their diameter. During microcirculation, they have to withstand high shear stresses, rapid elongation, folding, and deformation. Over time, the cell membrane is damaged by these extraordinary stresses. Because of the lack of nuclei and organelles, red blood cells cannot divide or repair their cell membranes. Senescent erythrocytes lose their flexibility due to their fragmented membranes. These stiff cells could do harm to small capillaries or even clog them. To avoid this potential harm, old erythrocytes are recognized by phagocytes and destroyed. This phagocytosis mainly takes place in the spleen and cells of the reticulo-endothelial system (RES). See Jandl, J. H., Blood: Textbook of Hematology, 2$^{nd}$ Ed. Little, Brown and Company, 1996 (hereinafter "Jandl").

To compensate for phagocytosis of senescent red blood cells, it is necessary to build new erythrocytes continuously. The maturation of undifferentiated stem cells to mature erythrocytes is called erythropoiesis and takes place in the bone marrow. Erythropoiesis not only has to compensate for the continuous loss of old erythrocytes, but also for the additional loss of cells due to random breakdown, as well as due to internal and external bleeding. Furthermore, the number of red blood cells has to be adjusted to varying environmental conditions, as for instance a transition from low to high altitudes or vice versa, by increasing the rate of erythropoiesis, or, conversely, by neocytolysis, a process believed to be wherein macrophages start to phagocytose young erythrocytes (neocytes).

During the process of erythropoiesis, the cell population undergoes a series of proliferations and differentiations. Starting from multipotential stem cells, erythroid cells mature to BFU-Es (earliest stage of erythroid committed cells), CFU-Es, different stages of erythroblasts, and finally reticulocytes. The reticulocytes are released from the bone marrow into blood and mature within 1-2 days to erythrocytes (see FIG. 1).

The primary control of erythropoiesis is governed by the hormone erythropoietin (EPO). EPO is released into the blood stream by the kidneys based on a negative feedback mechanism that reacts to the partial pressure of oxygen in blood. The concentration of EPO affects the number of circulating red blood cells by determining the number of cells that mature into erythrocytes, either by recruitment or by preventing apoptosis (programmed cell death), and by affecting the velocity of maturing of progenitor and precursor cells. Thus, disturbances in oxygen delivery can be adjusted for by an adaptive resetting of the rate of erythropoiesis. Additionally, as already mentioned above, there exists a physiological process which affects the selective degradation of young erythrocytes in situations of red cell excess, called neocytolysis. Neocytolysis seems to be triggered by a drop in the EPO level. See Rice, L., and Alfrey, C. P., Cellular Physiology and Biochemistry, 2005, Vol. 15, pp. 245-250 (hereinafter "Rice 2005"); Rice, L., Alfrey, C. P., Driscoll, T., Whitley, C. E., Hachey, D. L., and Suki, W., Amer. J. Kidney Diseases, 1999, Vol. 33, pp. 59-62 (hereinafter "Rice 1999"); and Rice, L., W. Ruiz, W., Driscoll, T., Whitley, C. E., Tapia, R., Hachey, D. L., Conzales, G. F., and Alfrey, C. P., Annals Internal Medicine. 2001, Vol. 134, pp. 652-656 (hereinafter "Rice 2001").

Another critical factor for effective erythropoiesis is the availability of iron which is indispensable for hemoglobin synthesis. If the body is not able to provide sufficient iron for this process, then ineffective erythropoiesis will result. See Finch, S., Haskins, D., and Finch, C. A., The Journal of Clinical Investigation. 1950, Vol. 29, pp. 1078-1086; and Lichtman, M. A., E. Beutler, E., Kipps, T. J., Seligsohn, U., Kaushansky, K., and Prchal, J. T. (editors), Williams Hematology, 7th edition, New York, McGraw-Hill, 2005 (hereinafter "Williams Hematology"). In normal subjects, the total iron content of the body stays within narrow limits (iron overload is toxic). Once an atom of iron enters the body it is conserved with remarkable efficiency and can remain in the body for more than ten years. Iron is lost via loss of cells (especially epithelial cells), bleeding and loss of very small amounts via urine and sweat. The balance of iron content is achieved by absorption and not by control of excretion. If the plasma concentration of iron is too low, then the level of the hormone hepcidin is decreased. The consequence of a lower hepcidin level is that more iron is taken up via the duodenum and more iron is released from macrophages and from the stores. See Crichton, R., Iron Metabolism. From Molecular Mechanisms to Clinical Consequences, New York, J. Wiley, 2009 (hereinafter "Crichton"); Fleming, M. D., J. Amer. Soc. Hematology, 2008, pp. 151-158 (hereinafter "Fleming"). Patients suffering from inflammation, such as dialysis patients, typically have higher hepcidin levels. Increasing iron availability in inflamed dialysis patients can be achieved by an increase of parenteral iron by increasing dose, frequency, or both, and by reducing inflammation by diagnosis and treatment of sources of inflammation, e.g., barrier breakdown (i.e., skin, periodontal disease, intestinal congestion), pulmonary or urinary tract infection, thrombosed fistulas or catheter, and by subsequent specific therapy, e.g., antibiotics, catheter removal, aseptic techniques when manipulating in-dwelling catheters, and surgical debridement of skin ulcers.

Since individual cells in the various cell populations which have to be considered have to be distinguished according to their age, age-structured population models are needed in order to describe the development of the cell populations. Besides these age-structured population models, the model of this invention includes a feedback loop including erythropoietin.

In one embodiment, a method of adjusting a patient's hematocrit and/or hemoglobin concentration to a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, the model including iron homeostasis, and employing the patient parameters and an initially selected ESA administration regimen in the model to predict the patient's hematocrit and/or hemoglobin concentration at the predetermined time with the initially selected ESA administration regimen. Examples of ESAs are provided in Table 1 (adapted from Phurrough S, Jacques L, Ciccanti M, Turner T, Koller E, Feinglass S: "Proposed Coverage Decision Memorandum for the Use of Erythropoiesis Stimulating Agents in Cancer and Related Neoplastic Conditions"; Centers for Medicare and Medicaid Services; Administrative File: CAG #000383N; May 14, 2007). See also Pfeffer, M. A., Burdmann, E. A., Chen, C-Y., Cooper, M. E., de Zeeuw, D., Eckardt, K-U., Feyzi, J. M., Ivanovich, P., Kewalramani, R., Levey, A. S., Lewis, E. F., McGill, J. B., McMurray, J. J. V., Parfrey, P., Parving, H-H., Remuzzi, G., Singh, A. K., Solomon, S. D., Toto, R., The New England Journal of Medicine, 2009, 361(21), pp. 2019-2032; and Singh, A. K., Szczech, L., Tang, K. L., Barnhart, H., Sapp, S., Wolfson, M., Reddan, D., The New England Journal of Medicine, 2006, 355(20), pp. 2085-2098 (hereinafter "Singh et al."). Note that unlike other ESAs listed in Table 1, Peginesatide is not a biologically derived EPO; it is a synthetic peptide that stimulates EPO receptors.

TABLE 1

Erythropoiesis Stimulating Agents: EPO = erythropoietin.

| Compound | Drug Names | Manufacturer |
| --- | --- | --- |
| EPO α | Epogen ® | Amgen |
| EPO α | Procrit ® | Amgen |
| EPO α (w/o serum albumin) | Eprex ® Epypo ® Epopen ® Epoxitin ® Globuren ® | J&J subsidiary (Otho Biologics) |
| EPO β | (Neo)Recormon | Roche |
| EPO β | Erantin ® | Boehringer Mannheim (Spain), Roche (Spain) |
| EPO β | Epoch ® | Chugai |
| EPO δ in human cell lines | Dynepo Gene Activated EPO | Aventis Transkaryotic Therapies |
| EPO Ω | Epomax ® Hemax ® Hemax ®-Eritron ® | Baxter |
| Modified EPO α Darbepoietin | Aranesp ® | Amgen |
| Modified EPO α Darbepoietin | Nespo ® | Amgen |
| Modified EPO β Continuous EPO Receptor Activator (Pegylation) | Mircera ® | Roche |
| Peginesatide | Omontys ® | Affymax |

Optionally, if the patient's hematocrit and/or hemoglobin concentration is not predicted by the model to be in the desired range at the predetermined time with the initially selected ESA administration regimen, the method includes employing the model with one or more different ESA administration regimens until the model predicts that the patient's hematocrit and/or hemoglobin concentration will be in the desired range at the predetermined time. The method then includes administering ESA to the patient with an ESA administration regimen predicted to adjust the patient's hematocrit and/or hemoglobin concentration to a value within the desired range at the predetermined time. The ESA administration regimen can include iron administration, and the model includes iron homeostasis with iron administration, and modeling the influence of iron homeostasis on erythropoiesis. The patient parameters can include, for example, the starting hematocrit and/or hemoglobin concentration in the patient's blood, the total blood volume of the patient, the lifespan of red blood cells (RBCs) of the patient, the mean corpuscular volume of the RBCs, the rate of neocytolysis in the patient's blood, the distribution of cell hemoglobin content in the patient's blood, the distribution of red blood cell size, iron storage level of the patient, transferrin saturation (TSAT), serum transferrin receptors, red cell zinc protoporphyrin level, hypochromic red blood cells, hypochromic reticulocytes, ferritin, endogenous EPO levels, C-reactive protein (CRP) levels, interleukin-6 (IL-6) levels, and the hepcidin levels of the patient.

The starting hematocrit and/or hemoglobin concentration in the patient's blood can be obtained from routine laboratory measurements known in the art. The total blood volume (BV) of the patient can be estimated as described further below, or measured by use of radio-labeling red blood cells with chromium-51 to estimate red blood cell volume (RCV) and using the formula $$BV=RCV/(0.9*Hctv)$$

where Hctv is the venous hematocrit, obtained from routine laboratory measurements known in the art. See Albert S. N., Blood volume measurement, In: Nuclear Medicine In Vitro. 2 ed. Philadelphia: JB Lippincott Co., 1983; Bernard P. J., Nouv Rev Fr Hematol 1994, 36(2), pp. 155-157; and International Committee for Standardization in Haematology:

Recommended methods for measurement of red-cell and plasma volume, J Nucl Med 1980, 21(8), pp. 793-800. The lifespan of RBCs of the patient can be estimated from endogenous alveolar carbon monoxide concentrations. See Strocchi A., Schwartz S., Ellefson M., Engel R. R., Medina A., Levitt M. D., J Lab Clin Med 1992, 120(3), pp. 392-399. The mean corpuscular volume can be obtained from routine laboratory measurements known in the art. The rate of neocytolysis in the patient's blood can be estimated from correlations with reduced expression of CD44 (homing-associated cell adhesion molecule) and CD71 (transferrin receptor). See Chang C. C., Chen Y., Modi K., Awar O., Alfrey C., Rice L., J Investig Med 2009, 57(5), pp. 650-654.

The models of this invention can track the patient's predicted hematocrit and/or hemoglobin concentration over time, such as between about 5 days and about 200 days of the ESA administration regimen. The predetermined time can be any future time after an ESA administration regimen is selected and the predicted regimen is initiated. In some embodiments, the patient undergoes a medical procedure prior, during, or after the ESA administration regimen, such as blood donation, surgery, and dialysis, or any combination thereof. For dialysis patients, the desired hematocrit is typically in the range of between about 28 percent and about 36 percent and the desired hemoglobin concentration is typically in a range of between about 9.5 g/dL and about 12 g/dL. See Drüeke, T. B., Locatelli, F., Clyne, N., Eckardt, K-U., Macdougall, I. C., Tsakiris, D., Burger, H-U., Scherhad, A., The New England Journal of Medicine, 2006, 355(20), pp. 2071-2084; Parfrey, P. S., 2006, American Journal of Kidney Diseases, 47(1), pp. 171-173; Strippoli, G. F. M., Craig, J. C., Manno, C., Schena, F. P., Journal of the American Society of Nephrology, 2004, 15, pp. 3154-3165 (hereinafter "Strippoli et al."); Volkova, N., Arab, L., Evidence-Based Systematic Literature Review of Hemoglobin/Hematocrit and All-Cause Mortality in Dialysis Patients, 2006, 47(1), pp. 24-36. For elective orthopaedic surgery patients, the desired hemoglobin concentration for males and females is typically greater than or equal to 13 g/dL, and 12 g/dL, respectively. See Goodnough L. T., Maniatis A., Earnshaw P., Benoni G., Beris P., Bisbe E., Fergusson D. A., Gombotz H., Habler O., Monk T. G., Ozier Y, Slappendel R., and Szpalski M., British Journal of Anaesthesia 106 (1) pp. 13-22 (2011).

In another embodiment, a method of determining a patient's hematocrit and/or hemoglobin concentration within a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, the model including iron homeostasis, and employing the patient parameters and an initially selected EPO administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, or a different ESA administration regimen is desired due to other considerations, the method includes employing the model with one or more different ESA administration regimens until the model predicts that the patient's hematocrit and/or hemoglobin concentration will be in the desired range at the predetermined time. The method then can include administering ESA to the patient with the ESA administration regimen predicted to adjust the patient's hematocrit and/or hemoglobin concentration to a value within the desired range at the predetermined time.

In yet another embodiment, a hemodialysis system includes a hemodialysis machine including a blood pump, a modular drug delivery device comprising at least one erythropoiesis stimulating agent (ESA) pump, at least one iron replacement product pump, at least one ESA vial holder, and at least one iron replacement product vial holder, and a housing to which the blood pump and the modular drug delivery device are secured.

Figure 2:
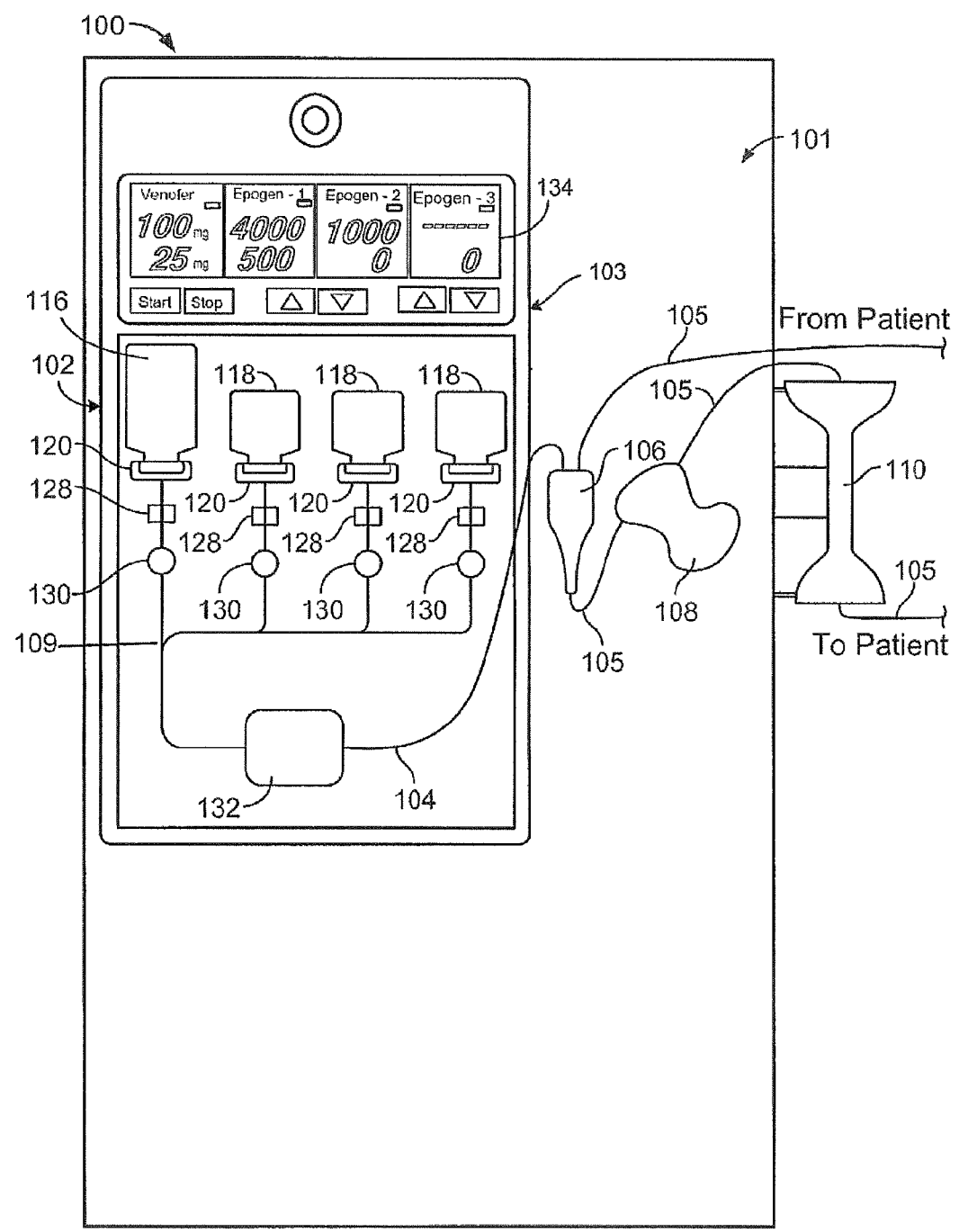
FIG. 2 is an illustration of a hemodialysis machine that includes a modular drug delivery device. A drug administration fluid line set and multiple drug vials are secured to the modular drug delivery device.

Referring to U.S. Pat. No. 8,382,696 B2 issued to Beiriger et al. on Feb. 26, 2013, and as shown in FIG. 2, a hemodialysis system 100 includes a hemodialysis machine 101 that has a drug delivery system 102. The drug delivery system 102 includes a modular drug delivery device 103 and a disposable drug administration fluid line set 109 that is connected to the drug delivery device 103. A drug delivery line 104 of the drug administration fluid line set 109 is fluidly connected to a blood circuit of the hemodialysis system 100. The blood circuit of the hemodialysis system 100 includes, among other things, a blood line set comprising multiple blood lines 105, a drip chamber 106, and a dialyzer 110. A blood pump (e.g., a peristaltic pump) 108 is configured to pump blood through the blood circuit during treatment. The hemodialysis system 100 also includes a dialysate circuit and various other components that, for the sake of simplicity, are not described in detail. During hemodialysis treatment, blood is drawn from the patient and, after passing through the drip chamber 106, is pumped through the dialyzer 110 where toxins are removed from the blood and collected in dialysate passing through the dialyzer. The cleansed blood is then returned to the patient, and the dialysate including the toxins (referred to as "spent dialysate") is disposed of or recycled and reused. As discussed in greater detail below, during the hemodialysis treatment, drugs (such as erythropoiesis stimulating agents, e.g., Epogen®, and iron replacement products, e.g., Venofer®) are also delivered to the drip chamber 106 using the drug delivery system 102. The drugs mix with the patient's blood within the drip chamber 106 and are then delivered to the patient along with the patient's blood.

Figure 3:
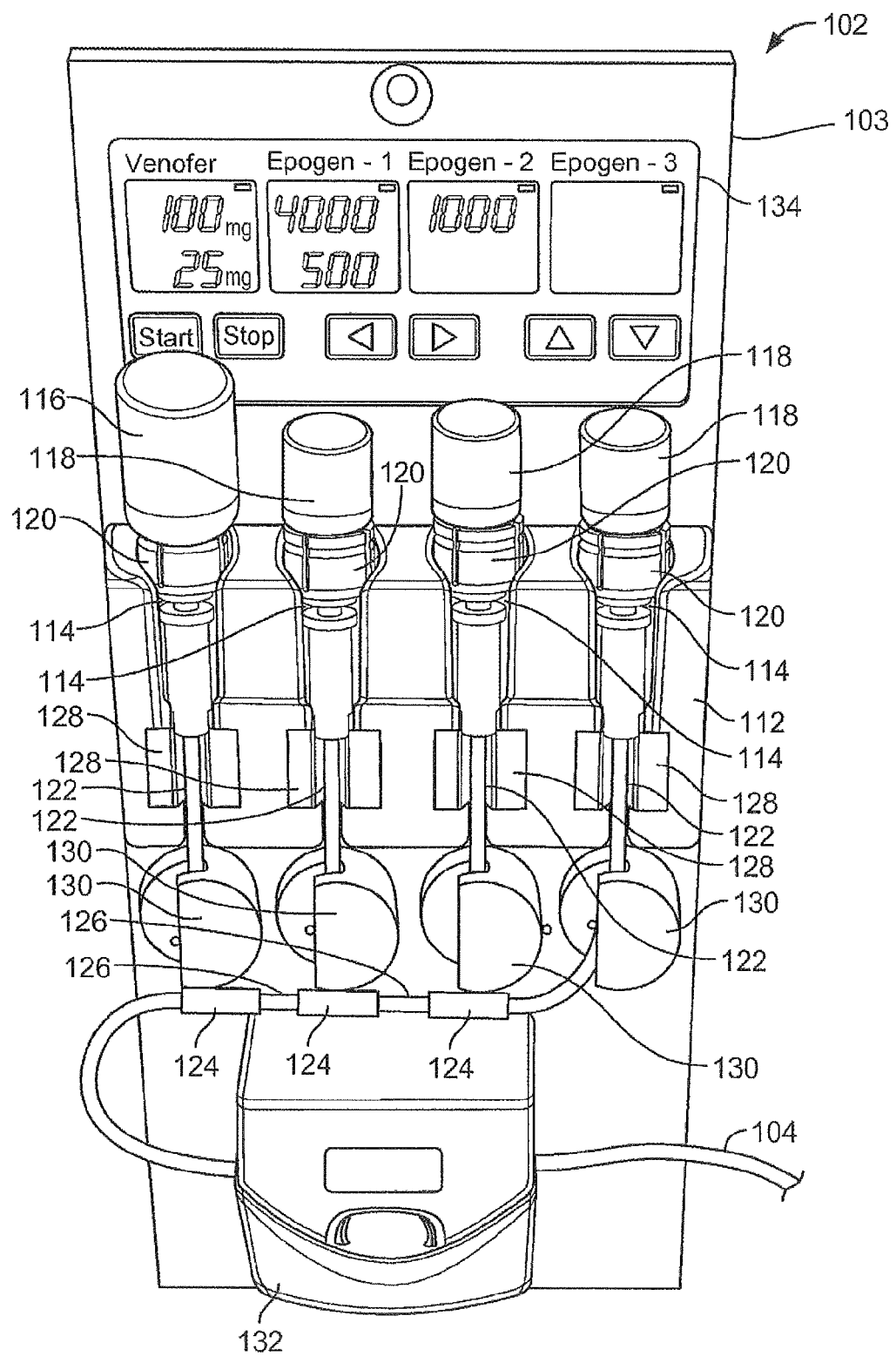
FIG. 3 is a perspective view of the modular drug delivery device of the hemodialysis machine shown in FIG. 2 and the drug administration fluid line set and drug vials that are secured to the modular drug delivery device.

As shown in FIG. 3, the modular drug delivery device 103 includes a drug vial holder 112 that defines four channels 114. Each of the channels 114 is designed to hold captive a drug vial 116, 118. The channels 114 can, for example, be recesses that are formed within the drug vial holder 112 and that are sized and shaped to receive only the caps and narrow neck portions of the vials 116, 118 such that the larger body portions of the vials sit above the holder 112. In the illustrated implementation, the vial 116 furthest to the left contains Venofer® and the three vials 118 to the right of the Venofer® vial 116 contain Epogen®. Venofer® (iron sucrose injection, USP) is a sterile, aqueous complex of polynuclear iron (III)-hydroxide in sucrose that is manufactured by American Regent, Inc. Venofer® is indicated in the treatment of iron deficiency anemia in patients undergoing chronic hemodialysis who are receiving supplemental erythropoietin therapy. Epogen® is a drug that stimulates the production of red blood cells and is also commonly used in dialysis patients. Epogen® is manufactured by Amgen, Inc.

The disposable drug administration fluid line set 109 is fluidly connected to each of the vials 116, 118. The drug administration fluid line set 109 includes four drug vial spikes 120 that connect to the vials 116, 118 in a manner to allow the drugs within the vials (e.g., the Venofer® and Epogen®) to flow into feeder lines 122 via the drug vial spikes 120. Each of the feeder lines 122 is attached to a T-connector 124. The T-connectors 124 and associated tubing segments 126 connect the feeder lines 124 to the drug delivery line 104. The drug vial spikes 120 can be formed of one or more relatively rigid medical grade plastics, such as polycarbonate or alphamethylstyrene (AMS), and the various fluid lines can be formed of a more flexible medical grade plastic, such as polyvinylchloride (PVC).

Each of the feeder lines 122, as shown in FIG. 3, passes through (e.g., is threaded through) a bubble detector 128. The bubble detectors 128 are capable of detecting air bubbles within the feeder lines 122. As a result, each of the bubble detectors 128 can determine whether its associated drug vial 116, 118 is empty during treatment, because air is drawn from the vial 116, 118 into the feeder line 122 when the vial is empty. In some implementations, the bubble detectors 122 are optical detectors. The OPB 350 bubble detector made by Optek can, for example, be used. Other types of optical detectors can alternatively or additionally be used. Similarly, other types of sensors, such as sensors utilizing ultrasound technology can be used as the bubble detectors. Examples of such sensors include the AD8/AD9 Integral Ultrasonic Air-In-Line, Air Bubble Detector and the BD8/BD9 Integral Ultrasonic Air Bubble, Air-In-Line & Liquid Level Detection Sensors (manufactured by Introtek International (Edgewood, N.Y.)). In some implementations, the bubble detector 128 includes a sensor that, in addition to sensing the presence of an air bubble within its associated feeder line 122, can sense the presence of the feeder line itself.

Downstream of the bubble detectors 128, the feeder lines 122 pass through (e.g., are threaded through) occluders 130. Each of the occluders 130 can be used to crimp the portion of the feeder line 122 disposed therein to prevent fluid from passing through the feeder line 122. In some implementations, the occluders 130 are solenoid based rams. Alternatively or additionally, other types of automated occluders can be used. The occluders 130 can be collectively operated in a manner such that only one feeder line 122 is unclamped at any particular time.

The drug delivery line 104 to which each of the feeder lines 122 is fluidly connected passes through (e.g., is threaded through) a peristaltic drug pump 132. The drug pump 132 includes multiple rollers that compress the drug delivery line 104 in a manner to create a "pillow" of fluid (i.e., a "pillow" of air or liquid) that is pinched between two points of the drug delivery line 104 that are compressed by the pump rollers. The rollers are arranged around a circumference of a rotatable frame. As the frame is rotated, the rollers force the "pillow" of fluid through the drug delivery line 104 toward the drip chamber 106 (shown in FIG. 2). When the pump 132 is being operated and one of the occluders 130 is open (i.e., not clamping its associated feeder line 122), vacuum pressure is applied to the drug vial 116, 118 that is connected to the feeder line 122 associated with the open occluder 130. In certain cases, the initial pressure in the drug vial 116, 118 is equal to the ambient pressure and when all of the drug has been delivered, the ending pressure within the vial is about −10 psi. In other words, the pressure within the drug vial 116, 118 progresses from ambient to −10 psi as the drug is delivered. The pump 132 is configured to generate a vacuum pressure within the drug delivery line 104 and feeder line 122 that exceeds the competing vacuum within the drug vial 116, 118. As a result, the drug is drawn from the vial 116, 118, through the drug vial spike 120, through the feeder line 122, and into the drug delivery line 104.

In some implementations, each channel 114 of the drug vial holder 112 includes a sensor to sense the presence of a vial or drug container. In certain implementations, each drug channel 114 includes a system which identifies the drug vial installed. The drug vial identification system can, for example, include a bar code reader that reads bar codes on the vials. Different types of sensors can alternatively or additionally be used. In some implementations, for example, the vial identification system uses RFID technology. Other examples of suitable sensors include color sensors for sensing the color of color coded drug vials and/or for sensing the color of the drug within the vial, photo sensors (e.g., cameras) that are equipped with text recognition software to read text on the drug vial, capacitive sensors that permit different size vials to be detected, load cells or scales that detect the mass of the vial, and conductivity or electrical impedance sensors that can be used to determine the type of drug within the vial.

The drug delivery device 103 also includes a control unit (e.g., a microprocessor) that can power the various components of the drug delivery device 103. The control unit can receive signals from and send signals to the various components of the drug delivery device 103, including, but not limited to, the bubble detectors 128, the occluders 130, the drug pump 132, the drug vial ID sensors, and other sensors along the drug lines. The control unit can control the various components of the drug delivery device 103 based on information received from these components. For example, the control unit can control the occluders 130 to ensure that only one of the occluders 130 is open at a time. This helps to ensure that drug is pulled from only one of the vials 116, 118 at a time during treatment. The control unit can also determine the volume of drug delivered based on operation data of the drug pump 132 and can control the occluders 130 based on the drug volume determined to have been delivered. For example, upon determining that the prescribed volume of the drug has been delivered, the control unit can close the occluder 130 associated with that drug vial 116, 118 and open the occluder 130 associated with the next drug to be delivered.

The control unit can also control the timing with which the various occluders 130 are opened and closed. For example, after the full contents of a vial have been evacuated, air will be sucked into the feeder line 122 associated with that vial. As the air passes through the feeder line 122, the bubble detector 128 will detect the air and transmit a signal to the control unit indicating that the vial is empty. In response, the control unit can close the occluder 130 associated with the empty vial and open the occluder 130 associated with the vial containing the next drug to be delivered. Upon receiving information from the bubble detectors 128 indicating that all of the vials have been emptied, the control unit can turn off the drug pump 132.

The control unit can also control certain components of the drug delivery device 103 based on signals received from the drug vial ID sensors, which indicate the presence of a vial and/or the identity of the vial contents. Such an arrangement can help to ensure that the correct vials (e.g., the correct number of vials and the vials containing the correct contents) are used for the treatment. Upon receiving signals from the drug vial ID sensors that do not match the inputted treatment information, for example, an alarm (e.g., an audible and/or visual alarm) can be activated. Alternatively or additionally, the drug delivery device 103 can be configured so that treatment cannot be initiated until the sensors detect the correct combination of vials.

The control unit can also be configured to adjust the patient's undesired hematocrit and/or hemoglobin concentration to a value within a desired range at a predetermined time by i) employing a model for predicting the patient's hematocrit and/or hemoglobin concentration at a predetermined time, the model including iron homeostasis, and by ii) operating the blood pump, the at least one ESA pump, and the at least one iron replacement product pump to deliver blood, ESA, and iron replacement product to the drip chamber via the at least one of the blood lines connected to the drip chamber and the at least two of the drug lines connected to the drip chamber, according to an ESA administration regimen predicted to adjust the patient's hematocrit and/or hemoglobin concentration to a value within the desired range at the predetermined time. Delivery of ESA and iron replacement product to the drip chamber can be simultaneous, consecutive, or independent of one another.

The drug delivery device 103 (e.g., the control unit of the drug delivery device 103) is configured to sense if the blood pump 108 of the dialysis machine 101 is running and to pause drug delivery if the blood pump 108 is stopped. This technique prevents 'pooling' of the delivered drug in the drip chamber 106 during treatment.

Still referring to FIG. 3, the drug delivery device 103 further includes a user interface 134 that is connected to the control unit. The user interface 134 includes right/left arrow keys that allow the user to navigate through displays associated with the vials 116, 118. The user interface 134 also includes up/down arrow keys that enable the user to set the desired dosage for each of the vials 116, 118. In addition, the user interface 134 includes start and stop keys that allow the user to start and stop the drug delivery device 103.

Any of various other types of user interfaces can alternatively or additionally be used. In some implementations, the drug delivery device includes a user interface that allows the user to select a drug to infuse from a menu. In certain implementations, the user may confirm that the drug identified by the drug vial ID sensor is correct and/or make appropriate adjustments. The user interface can be used to input and/or monitor various different treatment parameters. Examples of such parameters include drug dosage, drug delivery rate, amount of drug delivered, status of the drug delivery for each drug channel, time, percent complete, percent remaining, time remaining, time delivered, date, patient ID, patient name, alarms, alerts, etc. Such user interfaces can include a color graphical display. In certain implementations, for example, the user interface is color coded according to drug, dosing, or status of drug delivery (e.g., done, running, ready, etc.).

The drug delivery device 103 also includes an alarm and/or alert system to which the control unit of the drug delivery device 103 is connected. The alarm and/or alert system can be configured to emit a visual and/or audio alarm and/or alert. The alarm and/or alert system can further include pre-programmed alarm and/or alert limitations so that when a user modifies any aspect of the system to be outside of the limitations, or the machine itself detects any aspects of the system to be outside of the limitations, the module emits an alarm and/or alert.

Turning back to modeling the life cycle of red blood cells, an erythrocyte (i.e., a red blood cell (RBC)) that reaches an age of 120 days, has traveled approximately 480 kilometers, making about 170,000 circuits, in each cycle enduring osmotic swelling and shrinkage and a number of deformations while passing through capillaries. The accumulated damage to the membrane of the RBC is believed to lead to the destruction of the cell.

About two decades ago it was observed that erythrocytes actually undergo suicidal death. The suicidal death of erythrocytes is called eryptosis. This term was chosen in order to point out the differences from and similarities to apoptosis, the programmed cell death of nucleated cells. Although there exist a number of studies concerning eryptosis, and some parts are understood in great detail, the precise process and mechanisms remain elusive.

Stimulation of eryptosis is governed by a complex signaling network and involves activation of cation channels. (F. Lang, C. Birka, S. Myssina, K. S. Lang, P. A. Lang, V. Tanneur, C. Duranton, T. Wieder, and S. M. Huber. *Advances in Experimental Medicine and Biology,* 559:211-217, 2004). Shortly before they are phagocytosed by macrophages, which takes place mainly in the spleen, one can observe distinctive cell shrinkage, plasma membrane microvesiculation and an exposure of phosphatidylserine (PS) on the cell surface. These PS-exposing erythrocytes are recognized, engulfed and degraded by macrophages. (D. Bratosin, J. Estaquier, F. Petit, D. Arnoult, B. Quatannens, J. P. Tissier, C. Slomianny, C. Sartiaux, C. Alonso, J. J. Huart, J. Montreuil, and J. C Ameisen. *Cell Death Differ,* 8(12):1143-1156, December 2001).

The normal lifespan and senescence can be either accelerated or delayed by environmental signals. Triggers of eryptosis include osmotic shock, oxidative stress, prostaglandin E2, energy depletion, chlorpromazine, aluminum, mercury, etc. Diseases which are associated with an early expression of PS and thus accelerated eryptosis are, for instance, iron deficiency, sepsis, hemolytic uremic syndrome and sickle-cell anemia. See R. F. Zwaal, P. Comfurius, and E. B. Bevers *Cellular and molecular life sciences,* 62:971-988, 2005. On the other hand eryptosis may be inhibited by erythropoietin, adenosine, catecholamines, nitric oxide and activation of G-kinase. See M. Föller, S. M. Huber, and F. Lang. *IUBMB Life,* 60:661-668, 2008. Thus, EPO seems not only to increase the number of circulating erythrocytes by preventing apoptosis of progenitor cells but also by prolonging the lifespan of circulating RBC by inhibiting the cation channels. See F. Lang, K. S. Lang, P. A. Lang, S. M. Huber, and T. Wieder *Antioxidants & Redox Signaling,* 8:1183-1192, 2006; A. B. Schwartz, B. Kelch, L. Terzian, J. Prior, K. E. Kim, E. Pequinot, and B. Kahn. *ASAIO transactions,* 36:M691M696, 1990. The cation channels are volume-sensitive, and, after activation of the channel, phosphatidylserine asymmetry is reversed and phosphatidylserine is exposed to the outside of the erythrocyte. Binding of erythropoietin to RBC and inhibition of the channels may contribute to an increase in the erythrocyte number during erythropoietin therapy. See S. Myssina, S. M. Huber, C. Birka, P. A. Lang, K. S. Lang, B. Friedrich, T. Risler, T. Wieder, and F. Lang. *Journal of American Society of Nephrology,* 14:2750-2757, 2003. Surprisingly, it was recently observed that erythrocytes from erythropoietin overexpressing mice die faster ex vivo. See M. Foeller, R. S. Kasinathan, S. Koka, S. M. Huber, B. Schuler, J. Vogel, M. Gassmann, and F. Lang. *American Journal of Physiology—Regulatory, Integrative and Comparative Physiology,* 293:R1127R1134, 2007. This observation leaves room for discussion. It has been suggested that: "Possibly, erythropoietin stimulates the expression of genes in progenitor cells, which foster eryptosis and thus accelerate erythrocyte death as soon as the erythropoietin concentrations decline." See F. Lang, E. Gulbins, H. Lerche, S. M. Huber, D. S. Kempe, and M. Föller. Eryptosis, *Cellular Physiology and Biochemistry,* 22:373-380, 2008.

Erythropoiesis and its Regulatory Mechanisms

The daily production rate in a healthy adult totals about $200 \times 10^9$ red blood cells under normal conditions. This number can vary due to varying internal and environmental conditions. The body has to be able to adapt the number of erythrocytes to situations of anemia and/or hypoxia (e.g. after bleeding, due to a shortened RBC lifespan, due to an enhanced eryptosis, . . . ) as well as to situations of excessive red blood cells (e.g., high altitude dwellers descending to sea level).

The production of new erythrocytes takes place in the bone marrow. Undifferentiated stem cells in the bone marrow commit to the erythroid lineage and undergo a series of proliferations and differentiations. The earliest stage of erythroid committed cells are called BFU-Es (Burst-Forming Unit Erythroid). Within a few days the BFU-Es mature to CFU-Es (Colony-Forming Unit Erythroid), then they undergo different stages of erythroblasts, and finally they become reticulocytes. The reticulocytes are released to the blood stream and within 1-2 days they appear as mature erythrocytes. See Williams Hematology. Throughout the description below, the term progenitor cells is used to refer to BFU-E and CFU-E cells, and the term precursor cells is used to subsume proerythroblasts, basophilic erythroblasts, orthochromatophilic erythroblasts and bone marrow reticulocytes.

The primary control of erythropoiesis is governed by the hormone erythropoietin. EPO is produced mainly by peritubular cells in the renal cortex based on a negative feedback mechanism. The kidneys detect the partial pressure of oxygen in blood and react by releasing more EPO if the oxygen content is too low and vice versa. The concentration of EPO affects the number of circulating RBC by determining the number of cells that mature into erythrocytes. Erythropoietin plays a role in the recruitment of stem cells to the erythroid lineage, prevents apoptosis of progenitor cells and affects the maturation velocity of progenitor and precursor cells. Thus, disturbances in oxygen delivery can be adjusted for by an adaptive resetting of the rate of erythropoiesis. Additionally, there exists a physiological process wherein macrophages start to phagocytose young erythrocytes (neocytes), which is called neocytolysis. Neocytolysis seems to be triggered by a drop in the EPO level and helps to regulate situations of excessive red cell mass. See Rice 2001. Further, recent studies suggest that the concentration of EPO in blood influences the clearance of senescent RBCs and that EPO can prolong the lifespan of erythrocytes by inhibiting cation channels.

Progenitor and Precursor Cells

When a stem cell is committed to the erythroid lineage, it develops into an erythrocyte. The number of stem cells which enter the different hematopoietic lineages is determined by interleukines and growth factors. The immature erythrocyte undergoes a number of changes in structure, appearance and its requirements during the process of differentiation and proliferation. BFU-E cells, the first committed erythroid cells, express only a very small number of EPO-receptors (EpoR) and therefore they are almost EPO-independent for their survival. Within a few days they develop into CFU-E cells.

As cells mature to CFU-Es, the number of EpoR on the cell surface increases distinctly, and the cells become absolutely dependent on erythropoietin to prevent them from apoptosis. See H. Wu, X. Liu, R. Jaenisch, and H. F. Lodish. Cell, 83(1):59-67, 1995 (hereinafter "Wu et al."). Under normal conditions, large numbers of generated CFU-E are not surviving. After that very EPO-sensitive phase, the density of EpoRs declines sharply on early erythroblasts and EpoRs almost disappear at the stage of orthochromatophilic erythroblasts. See J. P. Greer, J. Foerster, G. M. Rodgers, F. Paraskevas, B. Glader, D. A. Arber, and R. T. Jr. Means. *Wintrobe's Clinical Hematology*, volume 1. Lippincott Williams & Wilkins, 12th edition, 2009 (hereinafter "Wintrobe's Clinical Hematology"). Under high levels of EPO, the marrow transit time of precursor cells is shortened, and high EPO levels result in release of still immature reticulocytes, which are referred to as stress reticulocytes. (See Williams Hematology).

One significant difference between progenitor and precursor cells is the synthesis of hemoglobin. Unlike progenitor cells, all types of precursor cells synthesize heme and the increased demand for iron for this process is reflected by a sharp increase in the number of transferrin receptors (TfR) in proerythroblasts (transferrin receptors are the path of iron uptake). TfRs reach their peak in intermediate erythroblasts and decline afterward and mature bone marrow reticulocytes express only a few TfRs (in comparison). A diagram of the different erythroid cell types is shown in FIG. 1.

Neocytolysis

The body has to be able to deal with situations of too few circulating erythrocytes as well as with excessive red blood cells. Whereas it is very effective to change the rate of erythropoiesis to adapt the system to situations when red cell numbers are low, this is not an adequate regulatory mechanism in situations of red cell mass excess. This is because a decrease in the rate of erythropoiesis takes relatively long to have a noticeable effect on the number of circulating red blood cells, due to the long lifespan of erythrocytes.

A mere 20 years ago, preventing apoptosis of red cell progenitors had been thought to be the sole regulating effect of EPO. Because this would only allow for a slow adaption in situations of too many RBC, the control of the body of red cell mass would be coarse. A decline in erythropoietin level results in more progenitor cells dying, but a suppression of the hormone has no effect on maturation of erythroid precursors. Thus, no decrement in the erythrocyte production would be observable within one week after EPO has declined. However, studies done on residents at very high altitude who rapidly descended to sea level, showed a decrease in red cell mass of 10-18% in the first 7-10 days. (See Rice 2001). Persons living in hypoxic environments, like high altitude, are normally polycythemic. Thus, their hematocrit is too high under normal conditions and as a consequence the release of EPO is suppressed.

Further investigations of situations where EPO levels are lower than normal (polycythemic high altitude dwellers, anemia of renal failure, human model based on EPO administration then withdrawal), suggest that a suppression of EPO leads to selective hemolysis of young red blood cells. (See Rice 2005). This process is called neocytolysis, to stress the fact that young erythrocytes (i.e., neocytes) are uniquely susceptible. See C.-C. Chang, Y. Chen, K. Modi, O. G. Awar, C. P. Alfrey, and L. Rice. *Journal of Investigative Medicine*, 57:650-654, 2009; Rice 2005; M. M. Udden, Pickett M. H. Driscoll, T. B., C. S. Leach-Huntoon, and C. P. Alfrey. *The Journal of Laboratory and Clinical Medicine*, 125:442-449, 1995.

Neocytolysis is initiated by a fall in erythropoietin levels and in Rice 2005 it was shown that, for instance, low doses of EPO, administered to high altitude dwellers on descent, completely abrogated neocytolysis. At the moment it remains unclear whether it is the rate of decline in EPO level or the drop of EPO beneath a certain threshold that acts as a trigger for neocytolysis. See C. P. Alfrey and S. Fishbane.

*Nephron Clinical Practice,* 106:149-156, 2007 (hereinafter "Alfrey et al."); Rice 1999. The current approach to treatment of anemia with ESAs deviates significantly from the normal internal systemic process. Neocytolysis, for instance, contributes to renal anemia. It is precipitated by the pathologic endogenous erythropoietin deficiency of renal disease and the short bursts in EPO concentration followed by sharp declines in serum levels due to administration of the hormone (especially during intravenous (i.v.) administration). It would be desirable to choose dosing schedules such that neocytolysis is minimized or totally prevented. (See Alfrey et al.; Rice 1999). A mathematical model could be very useful to define better ESA administration schemes which stimulate erythropoiesis in a more natural way and abrogate neocytolysis. Better and/or alternative administration schemes can include daily ESA administration, continuous ESA administration (e.g., via a pump), or monthly ESA administration.

Iron and Erythropoiesis

Erythropoiesis is a very complex process and even though erythropoietin is the key regulator, there are other proteins (e.g., interleukins, etc.) and substances (e.g., iron, folic acid, vitamin $B_{12}$, etc.) that are needed for an optimal erythropoiesis. Iron is a very critical factor for an effective production of red blood cells. The metal is indispensable for hemoglobin synthesis and the hemoglobin protein is the actual oxygen transporter in erythrocytes. The molecule makes up about 97% of the dry weight of red blood cells. If the body is not able to provide sufficient iron for the production of erythrocytes, then impaired erythropoiesis will result. (S. Finch, D. Haskins, and C. A. Finch. *The Journal of Clinical Investigation,* 29:1078-1086, 1950; Williams Hematology). In general, a healthy adult has difficulty providing sufficient iron to support production rates greater than three times basal. Higher rates may be possible when administering EPO and iron and in some diseases, e.g. hemochromatosis. (L. T. Goodnough. *Nephrology Dialysis Transplantation,* 17:14-18, 2002 (hereinafter "Goodnough 2002"); C. A. Finch. *Blood. The Journal of American Society of Hematology,* 60(6):1241-1246, 1982) (hereinafter "Finch 1982"). An undersupply of iron additionally leads to an increase in the number of hypochromic RBC. Hypochromic cells (i.e., cells in which the amount of hemoglobin is lower than the normal 26 pg) are small, have a reduced oxygen carrying capacity and are relatively fragile, and thus are likely to die earlier than normochromic erythrocytes. See D. M. Wrighting and N. C. Andrews. Iron Homeostasis and erythropoiesis. *Current Topics in Developmental Biology,* 82:141-159, 2008 (hereinafter "Wrighting"); A. Loria, L. Sánchez-Medal, R. Lisker, E. De Rodríguez, and J. Labardini. *Br J Haematol,* 13(3):294-302, May 1967.

Erythroid precursor cells are the most avid consumers of iron in the body. See P. Ponka and C. N. Lok. *The International Journal of Biochemistry & Cell Biology,* 31:1111-1137, 1999 (hereinafter "Ponka 1999"). The immature erythrocyte has only a few days to synthesize all the hemoglobin which the mature cell contains. Hemoglobin is a metalloprotein. The name refers to its special structure. A hemoglobin molecule consists of four subunits each composed of a globular protein embedding a heme group, and every heme group in turn contains one iron atom. Erythroid cells rely completely on transferrin receptors to take up iron. See R. Y. Chan, C. Seiser, H. M. Schulman, L. C. Kuhn, and P. Ponka. *European Journal of Biochemistry,* 220:683-692, 1994. Unlike progenitor cells, all types of precursor cells synthesize heme and the increased demand for iron for this process is reflected by a sharp increase in the number of TfR in proerythroblasts. Transferrin receptors reach their peak in intermediate erythroblasts followed by a decrease with further maturation.

In precursor cells, heme is essential for maintaining a "normal" number of TfR. Studies showed that inhibition of heme synthesis strongly inhibited TfR expression. It seems that there exists a positive feedback mechanism in which heme promotes a high rate of transferrin receptor synthesis. A high number of transferrin receptors enhances iron uptake and that in turn keeps hemoglobin synthesis at high levels. See P. Ponka. *Blood,* 89:1-25, 1997. There is evidence that precursor cells which have a low hemoglobin content are still able to proliferate but do not differentiate and undergo apoptosis. See J. A. Schmidt, J. Marshall, M. J. Hayman, P. Ponka, and H. Beug. *Cell,* 46:41-51, 1986 (hereinafter "Schmidt").

1. Iron Homeostasis

Iron plays a vital role in metabolic processes in all living organisms, including oxygen transport, DNA synthesis, and electron transport. It is the most important essential trace element and amounts to about 35-45 and 50-55 mg/kg body weight in adult women and men, respectively. See Williams Hematology; Ponka 1999. For a very good overview of iron homeostasis and metabolism, see Crichton and Lieu. Homeostasis is the state of equilibrium (balance between opposing pressures) in the body with respect to various functions and to the chemical compositions of the fluids and tissues. See Steadman's Medical Dictionary, $26^{th}$ Edition, Williams & Wilkins, 1995.

Iron is a key component of many cellular enzymes (e.g. oxidases, catalases, peroxidases, cytochromes, etc.). These enzymes are critical in many basic cellular processes, including cell proliferation and differentiation, DNA and RNA synthesis and electron transport. Further, iron, bound in heme, is essential for oxygen transport. Under normal conditions, total body iron burden is very tightly regulated, because excessive iron leads to tissue damage. Once an atom of iron enters the body, it is conserved with remarkable efficiency and can remain in the body for more than ten years. Iron is only lost via loss of cells (epithelial cells, bleeding) and very small amounts are lost via urine and sweat. Unlike other mammals, humans are not able to actively excrete iron. Thus, because of the toxic nature of iron, it is very important to keep absorption and needs well balanced.

Iron is absorbed from dietary sources via the duodenum. The uptake is regulated by the hormone hepcidin. Under normal conditions, the daily absorption of iron amounts to 1-2 mg. In general, in the organism iron is bound to proteins, because free iron results in formation of free radicals and destroys cells. The iron exporter ferroportin is needed to egress the metal from cells (e.g. enterocytes, macrophages, hepatocytes). Ferroportin is not only the effector of cellular iron export but also the receptor of the iron regulating hormone hepcidin. See Williams Hematology.

Much of the iron in the human body can be found in circulating erythrocytes incorporated in hemoglobin (1 ml of packed cells contain about 1 mg of iron). However, most of the iron used for the production of new erythrocytes comes from hemoglobin recycling and not from absorption. When a senescent red cell is phagocytosed, the macrophage internalizes hemoglobin, degrades it, and exports it back out into blood circulation.

Iron is stored in the form of ferritin or hemosiderin, where the latter is more a kind of a long-term storage, because iron within deposits of hemosiderin is very poorly available. Storage sites can be found mainly in the liver, the spleen, and the bone marrow but, for instance, small amounts of hemosiderin can be found in almost any tissue. There are differences between men and women in the amount of iron that is stored (men: about 200-400 mg, women: about 1000 mg,). See C. Crepaldi, A. Brendolan, V. Bordoni, M. R. Carta, V. D. Intini, F. Gastaldon, P. Inguaggiato, and C. Ronco. Hemodialysis International, 7(3):216-221, 2003 (hereinafter "Crepaldi").

Iron is carried around in plasma by a transport protein, which is called transferrin. Transferrin is produced by the liver. Cells which are in need for iron express transferrin receptors, and, after transferrin forms a complex with this receptor, iron is transported into the cell. Transferrin exists in three different forms: iron-free (apotransferrin), one iron (monoferric transferrin) and two iron (differic transferrin) atoms bound. The concentration of iron and the amount of transferrin present in plasma determine the relative abundance of each form. Although iron bound to transferrin amounts to only about 3 mg of total body iron, it is the most important iron pool with the highest rate of turnover, about 30 mg/day. Approximately 80% of this iron is transported to the bone marrow and used by erythroid cells. See Lieu. The amount of transferrin-bound iron is determined by three processes: macrophage iron recycling, iron storage (hepatic) and duodenal iron absorption. See Wrighting.

In the last 15 years, understanding of the regulation of systemic iron homeostasis has changed substantially. The antimicrobial peptide hepcidin (hepatic bactericidal protein), which is secreted by the liver, was identified to be the systemic iron regulator.

Figure 4:
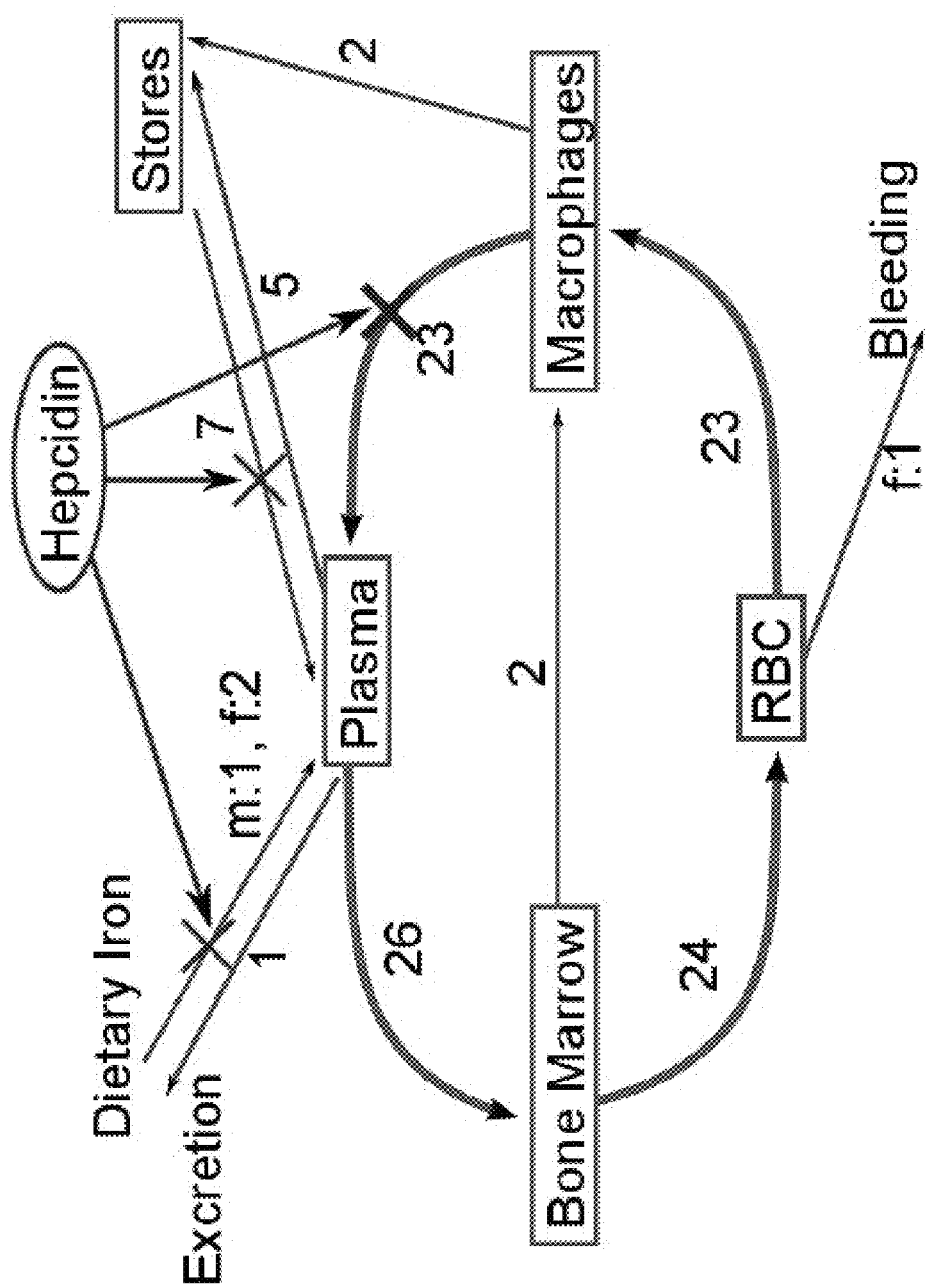
FIG. 4 is a schematic illustration of the iron cycle in an adult. The numbers indicate the amount of iron (in mg) that is shifted per day under normal conditions. Approximately 1 mg of iron is excreted daily because of shedding of epithelial cells, via urine and sweat. Women additionally lose iron due to menses or pregnancy.
Figure 5:
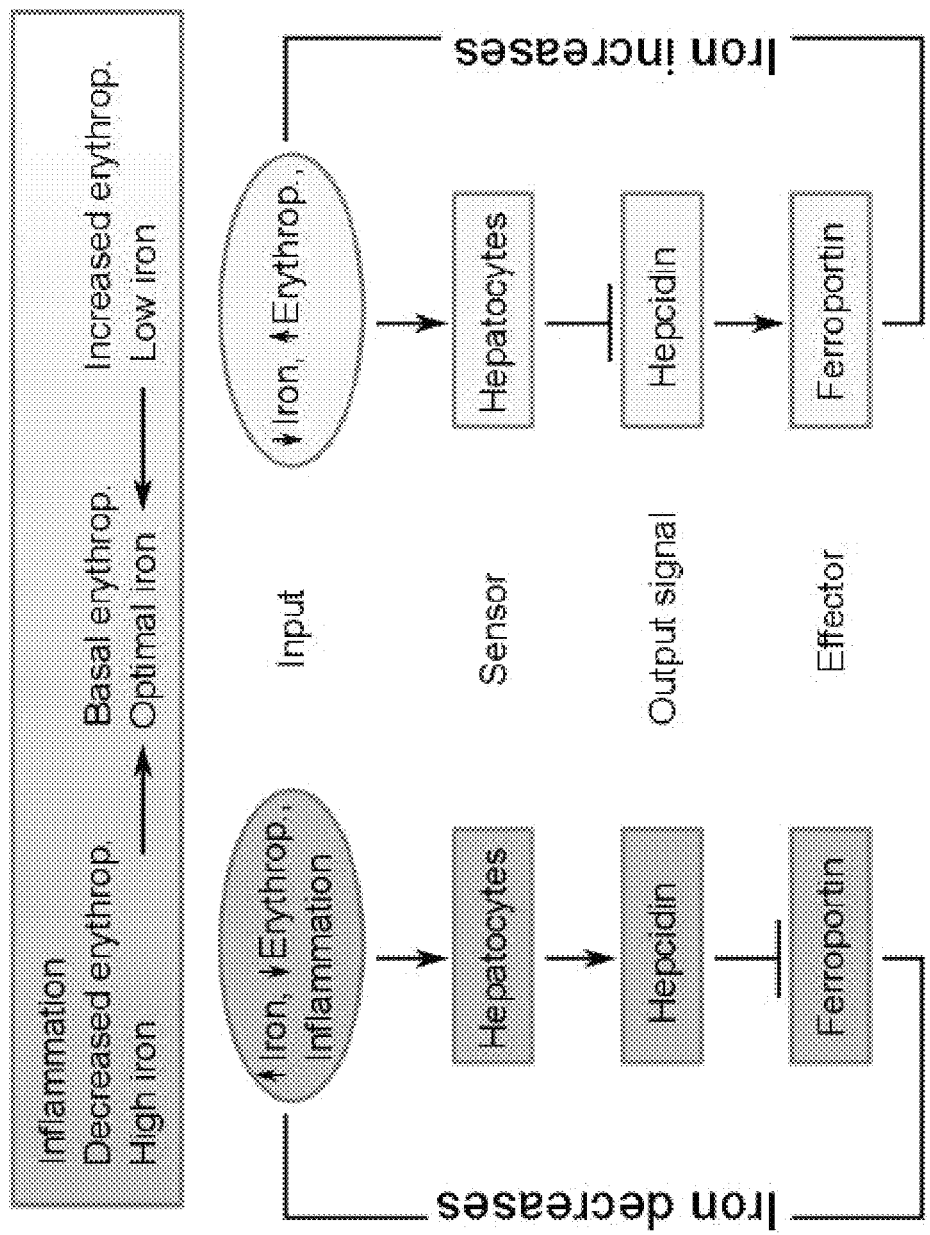
FIG. 5 is a schematic illustration of systemic iron regulation.

Hepcidin inhibits iron transport by binding to the iron exporter ferroportin. Hence, it keeps gut enterocytes from secreting iron into circulation, thereby functionally reducing iron absorption. Further, it prevents iron release from macrophages and blocks the stores as well, by shutting off the means of transport out of cells. See FIG. 4 for a diagram of the iron cycle and daily turnover rates and FIG. 5 for a sketch of systemic iron regulation.

There exist some sensing mechanisms in the liver that gauge the amount of iron needed to support erythropoiesis. Note that hepatocytes in the liver, which secrete hepcidin, also release transferrin into circulation and are one of the major iron storage sites. If the concentration of iron in stores is too low and/or erythropoiesis is increased, then the level of the hormone hepcidin is decreased. Thus, for instance, low hepcidin concentrations are observed in patients with absolute iron-deficiency anemia, or anemias with high erythropoietic activity. See L. T. Goodnough, E. Nemeth, and T. Ganz. Blood, 116:4754-4761, 2010 (hereinafter "Goodnough 2010"). The consequence of a lower hepcidin level is that more iron is taken up via the duodenum and more iron is released from macrophages and from the stores. See Crichton; Fleming. If iron stores are full and/or erythropoiesis is decreased, then more hepcidin is secreted by hepatocytes. As a result of the binding to the iron exporter ferroportin, dietary iron absorption, macrophage iron recycling, and release of iron from stores are partly or fully blocked.

Hepcidin is an acute phase-reactant, and, during inflammation, cytokines stimulate overproduction of hepcidin. Hence, the feedback is altered during inflammation, which is a prominent problem in chronic kidney disease. As a consequence, the body is not able to sufficiently supply developing red blood cells with iron and erythropoiesis is impaired, even though there might be more than enough iron in stores and macrophages, but it is simply not available. This paradoxical situation is called functional iron deficiency, whereas a situation when the iron content of the body is too low (depleted stores) is referred to as absolute iron deficiency.

2. A Mathematical Model for Erythropoiesis Including Iron Homeostasis

For healthy persons, one can assume that erythropoiesis is always sufficiently supplied with iron. This assumption certainly does not hold for some types of anemia and it is not valid for the majority of dialysis patients. Therefore, the model developed in this section incorporates an extensive iron model in order to expand the possible applications to all dialysis patients and to pathologies where an unbalanced iron homeostasis leads to an abnormal erythropoiesis (e.g., anemia of absolute and functional iron deficiency, hemochromatosis, etc.). The incorporation of an iron submodel and its effects on erythropoiesis has a significant influence on the structure of the population equations.

A reduced reaction of the body to erythropoietin or ESAs is often the result of an insufficient iron availability in the body. A model which gathers the balance between developing precursor cells and iron that can be delivered to the bone marrow for hemoglobin synthesis is needed. Further, iron homeostasis itself is a very complex process. There are complex feedback mechanisms which determine how much iron is shifted around from one place to another in the body and how much is absorbed via dietary input. Unfortunately, most of these feedback mechanisms are not well understood.

A compartmental model for iron is considered and linked to a structured population model which governs the dynamics of the erythroid cell population. For a detailed explanation of amendments and modifications in the population equations for the iron model see Section 2.1. In Section 2.2 the derivation of the iron model is explained. For an overview of how the model developed in this section is organized, see FIG. 6B.

2.1. Population Model.

The structured population equations are designed to link the iron model to the cell population model in a physiologically meaningful way. Five different cell population classes (BFU-E, CFU-E, erythroblasts, marrow reticulocytes, circulating RBCs) are considered. The inclusion of iron makes it necessary to consider some physiological processes in detail. In many applications of structured population equations, the only attribute used to distinguish cells is the cell age. This concept is insufficient for the population class of the precursor cells, where iron is used to synthesize hemoglobin. Here, cells are characterized by their hemoglobin content, and the number of tranferrin receptors on the cell membrane, in addition to the cell age. For mature erythrocytes, cell age and hemoglobin content are used as attributes.

The two equations describing the progenitor cell populations (BFU-Es and CFU-Es) are solely structured using cell age. These types of cells do not synthesize hemoglobin and, therefore, they are not among the major consumers of iron. Hence, these two classes can be described by population equations of the form $$\frac{\partial}{\partial t}u(t,\mu) + v(E(t))\frac{\partial}{\partial \mu}u(t,\mu) = (\beta(E(t),\mu) - \alpha(E(t),\mu))u(t,\mu),$$

where $u(t,\mu)$ is the population density of cells at time t with cell age $\mu$. The functions $\beta$ and $\alpha$ describe the rate of division and rate of apoptosis, respectively, of the cells. Further, v describes the maturation velocity.

Precursor cells are the only erythroid cells that synthesize hemoglobin. In order to introduce these phenomena in the model and to keep track of the amount of hemoglobin the cells are synthesizing, two additional attributes are introduced in addition to cell age:

the number $\tau$ of TfRs per cell and
the amount h of hemoglobin each cell is carrying.

Thus, the general population equation for precursor cells is $$\frac{\partial}{\partial t}u(t, \mu, h, \tau) + \frac{\partial}{\partial \mu}(v_1(t, \mu, h, \tau)u(t, \mu, h, \tau)) + \quad (1)$$
$$\frac{\partial}{\partial h}(v_2(t, \mu, h, \tau)u(t, \mu, h, \tau)) + \frac{\partial}{\partial \tau}(v_3(t, \mu, h, \tau)u(t, \mu, h, \tau)) =$$
$$8\beta(t, \mu, 2h, 2\tau)u(t, \mu, 2h, 2\tau) -$$
$$(\beta(t, \mu, h, \tau) + \alpha(t, \mu, h, \tau))u(t, \mu, h, \tau).$$

Here $u(t,\mu,h,\tau)$ denotes the population density of the cell population at time t with maturity $\mu$, hemoglobin content h and number of transferrin receptors $\tau$. Further, the functions $\beta$ and $\alpha$ describe the rate of division and rate of apoptosis of the cells. The functions $v_1$, $v_2$, $v_3$ define the rate with which the structural variables $\mu$, h and $\tau$ are changing, respectively. For a derivation of the partial differential equation (1), see below.

Circulating red blood cells carry hemoglobin but they do not express TfRs for synthesis of the hemoglobin molecule and, therefore, a distinction is made between cells using only cell age $\mu$ and hemoglobin content h as structural variables. Hence, the general population equation reads as follows $$\frac{\partial}{\partial t}u(t, \mu, h) + \frac{\partial}{\partial \mu}(v_1(t, \mu, h)u(t, \mu, h)) + \frac{\partial}{\partial h}(v_2(t, \mu, h)u(t, \mu, h)) =$$
$$-\alpha(t, \mu, h)u(t, \mu, h).$$

2.1.1. Progenitor Cells: BFU-E and CFU-E Cells.

Assumptions:
1. The number of stem cells, which commit to the erythroid lineage depends on EPO.
2. Cells normally stay in this stage for 8 days (3 days BFU-E and 5 days CFU-E).
3. The number of transferrin receptors on BFU-E and CFU-E cells is negligible.
4. EPO has no effect on the number of divisions or the rate of apoptosis of BFU-E.
5. The proliferation rate of CFU-E cells is constant.
6. The rate of apoptosis depends strongly on EPO levels.
7. The maturation velocities of BFU-E and CFU-E cells are constant.

Different kinds of growth factors affect the number of stem cells and in vitro studies suggest that high levels of EPO can result in up to 20% more stem cells committing to the erythroid lineage. BFU-E and CFU-E cells express only a very small number of transferrin receptors on the cell membrane and the influence of iron on these cells is neglected. This is not entirely true, because, like all proliferating cells, they need a small amount of iron for division. These amounts are so small compared to the consumption of iron for hemoglobin synthesis that they are neglected. Even in situations of iron deficiency, the assumption is that there is enough iron for cell divisions of progenitor cells available and only hemoglobin synthesis is impaired. Thus, the following population equation is obtained for BFU-E cells:

$$\begin{cases} \frac{\partial}{\partial t}p(t, \mu^p) + \frac{\partial}{\partial \mu^p}p(t, \mu^p) = \beta^p p(t, \mu^p), \\ p(t, 0) = S_0(E(t)), \\ p(0, \mu^p) = p_0(\mu^p), \end{cases}$$

where $p(t,\mu^p)$ is the population density of the cell class at time t with maturity $\mu^p$, $0 \leq \mu^p \leq \mu_{max}^p = 3$, t>0. Further, $\beta^p$ is the constant proliferation rate (Assumption 4) and $p_0(\mu^p)$ is the population density at t=0. The number $S_0(E(t))$ of cells committing to the erythroid lineage is given by a sigmoidal function, $$S_0(E(t)) = \frac{a_1 - b_1}{1 + e^{-k_1 E(t) + c_1}} + b_1,$$

where E(t) is the EPO concentration at time t and $a_1$, $b_1$, $c_1$ and $k_1$ are positive constants and $a_1 > b_1$. The function $S_0$ increases monotonically with increasing EPO concentration (Assumption 1).

The equation for CFU-E cells is:

$$\begin{cases} \frac{\partial}{\partial t}q(t, \mu^q) + \frac{\partial}{\partial \mu^q}q(t, \mu^q) = (\beta^q - \alpha^q(E(t)))q(t, \mu^q), \\ q(t, \mu_{min}^q) = p(t, \mu_{max}^p), \\ q(0, \mu^q) = q_0(\mu^q), \end{cases}$$

where $q(t,\mu^q)$ is the population density of the CFU-E class at time t with maturity $\mu^q$, t>0 and $3 = \mu_{min}^q \leq \mu^q \leq \mu_{max}^q = 8$. The constant $\beta^q$ describes the division rate (Assumption 4) and $\alpha^q(E(t))$ the apoptosis rate which depends on the EPO-concentration (Assumption 5). Moreover, the number of cells leaving the BFU-E cell stage and entering the CFU-E cell stage per unit time requires the boundary condition $q(t,\mu_{min}^q) = p(t,\mu_{max}^p)$. Finally, $q_0(\mu^q)$ is the population density at t=0.

Again, a sigmoidal function is used to describe the dependence of the rate of apoptosis on EPO, $$\alpha^q(E(t)) = \frac{a_2 - b_2}{1 + e^{k_2 E(t) - c_2}} + b_2,$$

where E(t) is the EPO concentration and $a_2$, $b_2$, $c_2$ and $k_2$ are positive constants, $a_2 > b_2$. The function $\alpha^q$ is per definition a monotonically decreasing function. Thus, a higher level of EPO causes more cells to survive.

Finally, because of Assumption 7, it is assumed that cell age equals the actual age of the cells, i.e., $v^p = v^q \equiv 1$, $\forall t \geq 0$.

2.1.2. Precursor Cells: Erythroblasts and Marrow Reticulocytes.

Assumptions:
8. The class erythroblasts consists of all cell stages from proerythroblast to orthochromatophilic erythroblast.
9. Cells normally stay in this stage for 6-8 days (5 days erythroblasts and 1-3 days marrow reticulocytes).
10. Under high levels of EPO, so called "stress reticulocytes" are released.
11. All types of precursor cells synthesize hemoglobin.
12. The rate at which the amount of hemoglobin in precursor cells changes, depends on the number of TfRs on the cell surface and the currently available amount of iron.

13. The rate of change of TfRs in precursor cells depends on the cell age and the hemoglobin content of the cell.
14. Cells entering the erythroblast class may be equipped with different numbers of TfRs, i.e., TfRs need not be uniformly distributed among the erythroblast population at time t=0.
15. Hemoglobin is conserved during cell division and a mother cell divides into 2 daughter cells carrying equal amounts of hemoglobin.
16. TfRs are conserved during division and a mother cell divides into 2 daughter cells with equal numbers of TfRs.
17. The maturation velocity of erythroblasts is constant.
18. The proliferation rate of erythroblasts is constant.
19. The rate of apoptosis of erythroblasts depends on cell age and hemoglobin.
20. The maturation velocity of reticulocytes depends on EPO.
21. The rate of apoptosis of reticulocytes depends on cell age and on hemoglobin.
22. Reticulocytes mature but do not proliferate.
23. Iron that enters a precursor cell is incorporated into hemoglobin, i.e., no free iron in the cell is considered.

The number of TfRs increases sharply in the proerythroblasts and reaches its peak in intermediate erythroblasts before declining again (proerythroblasts: 300,000 TfRs/cell; basophilic erythroblasts: 800,000 TfRs/cell; mature reticulocytes: 100,000 TfRs/cell). See Wintrobe's Clinical Hematology. This reflects the increased demand of the cells for iron to synthesize hemoglobin Almost all iron contained in the cells is synthesized to hemoglobin, leaving mature erythrocytes with only a negligible amount of non-heme iron (Assumption 23). Depending on the maturity of cells different numbers of TfRs are to be expected (Assumption 13). Cells that are saturated with hemoglobin reduce the level of receptors. Further, there is evidence that in contrast to other cells, in the precursor cells the number of transferrin receptors is also controlled by a positive feedback involving the amount of already synthesized hemoglobin in the cell. In vitro hemoglobin was shown to be essential for these cells to maintain a normal number of TfRs. See Ponka 1999.

For the erythroblasts population class, the following PDE is obtained $$\begin{cases} \frac{\partial}{\partial t}r(t,\mu^r,h^r,\tau^r) + \frac{\partial}{\partial \mu^r}r(t,\mu^r,h^r,\tau^r) + \\ \quad v_2^r(\tau,a_1(t))\frac{\partial}{\partial h^r}r(t,\mu^r,h^r,\tau^r), \\ + \frac{\partial}{\partial \tau^r}(v_3^r(\mu^r,h^r,\tau^r)r(t,\mu^r,h^r,\tau^r)) = 8\beta u(t,\mu^r,2h^r,2\tau^r) - \\ \quad (\beta + \alpha^r(\mu^r,h^r))r(t,\mu^r,h^r,\tau^r), \\ r(t,\mu_{min}^r,0,\tau^r) = q(t,\mu_{max})\cdot\eta(\tau^r), \\ r(t,\mu^r,h^r,\tau^r) = 0, \text{ if } (\mu^r,h^r,\tau^r) \text{ is a boundary point} \\ \quad \text{and } h^r > 0, \\ r(0,\mu^r,h^r,\tau^r) = r_0(\mu^r,h^r,\tau^r), \end{cases}$$

where $r(t,\mu^r,h^r,\tau^r)$ is the population density of the erythroblast class at time t with maturity $\mu^r$, hemoglobin content $h^r$ and number of TfRs $\tau^r$, $8=\mu_{min}^r \leq \mu^r \leq \mu_{max}^r=13$, $0 \leq h^r \leq h_{max}^r$, $\tau_{min}^r \leq \tau^r \leq \tau_{max}^r$, $t>0$. The population density at t=0 is given as $r_0(\mu^r,h^r,\tau^r)$. Assumption 17 allows setting $v_\mu^r \equiv 1$, i.e., the cell age of the cell coincides with the actual age of the cell. The contact rate between the TfRs of a cell and transferrin molecules in plasma carrying iron is governed by the law of mass action:

$$d_1 \tau^r(t)a_1(t),$$

where $d_1$ is a rate constant, $\tau^r(t)$ is the number of TfRs on the cell membrane at time t and $a_1(t)$ is the concentration of iron in plasma at time t. Thus, the amount of hemoglobin in a cell evolves according to $$v_2^r(\tau^r,a_1) = d_2\tau^r a_1, \quad (2)$$

where $d_2$ is a rate constant that is different from $d_1$ (note that four atoms of iron are needed for one hemoglobin molecule). The change of the number of TfRs on the cell surface is described by a function $v_\tau^r$, depending on the cell age $\mu^r$ and the amount of hemoglobin $h^r$ (Assumption 13). The function $v_\tau^r$ is chosen such that it increases in the beginning and then decreases when the cells are "fully saturated" with hemoglobin.

$$v_3^r(\mu^r,h^r,\tau^r) = a_3\tau^r(h_*^r - b_3(h^r)^2) - c_3\max(\tau^r,0)(\mu^r - \mu_{max}^q)/(1+h^r),$$

where $a_3$, $h_*^r$, $b_3$ and $c_3$ are constants and $\mu_{max}^q$ is the maximal maturity of progenitor cells. The second term assures that cells which progress in maturation, but do not accumulate sufficient iron, lose transferrin receptors. The term $\max(\tau^r,0)$ is needed to guarantee that the number of TfRs can not become negative. The maximum function is not differentiable, therefore it is approximated by the following function $$s\max(\tau^r) = 0.5\tau^r + 0.5\sqrt{(\tau^r)^2 + 0.01}.$$

The rate of division $\beta^r$ is constant (Assumption 15). Note that the term $8\beta u(t,\mu^r,2h^r,2\tau^r)$ in the equation arises because of Assumptions 15 and 16. For further details see below. To model the rate of apoptosis $\alpha^r$, a decrease in expression of TfRs is taken into account and leads to a decrease in iron uptake and, thus, less hemoglobin is synthesized. Cells containing small amounts of hemoglobin arrest in differentiation (proliferation is not affected) and this leads to premature cell death. See Schmidt Therefore, it is assumed that $\alpha^r$ depends on $\mu^r$ and $h^r$ (Assumption 19)

$$\alpha^r(\mu^r,h^r) = b_4(h^{}-h^r)^2/(1+(\mu^{}-(\mu^r-\mu_{max}^q))^2), \quad (3)$$

where $b_4$, $h^{}$, $\mu^{}>0$ are constants. The parameters $h^{}$ and $\mu^{}$ can, for instance, be chosen as $$h^{}=h_{max}^r, \quad \mu^{}=\mu_{max}^r - \mu_{max}^q, \quad (4)$$

where $h_{max}^r$ is the maximal hemoglobin amount of precursor cells and $\mu_{max}^r$ is the maximal maturity of precursor cells.

Figure 7:
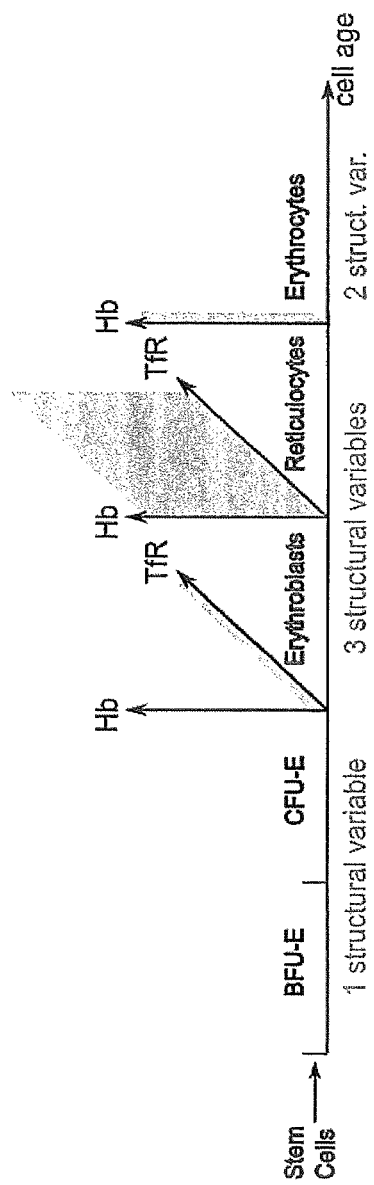
FIG. 7 is a schematic illustration of the fluxes through the different boundaries. Parts of the boundaries which are non-zero are depicted in gray.

In principle, the boundary conditions arise as a result of the fact that cells from the precedent class leave the class when they reach the maximum maturity and enter the next population class. Hence, there is a constant flux of cells from the CFU-E class to the erythroblasts class. However, the passage is more complicated because there is a flux from a population class with only one structural variable to a population class with three attributes. Thus, it has to carefully considered at which points of the boundary the cells are entering. It is useful to keep the physiological situation in mind. Progenitor cells do not synthesize hemoglobin. Hence, there are no cells entering the erythroblasts population class with h>0. On the other hand, it is not natural to apply the same assumption for transferrin receptors. For although the number of TfRs on progenitor cells is neglected, in fact, very mature CFU-E express a number of TfRs. Further, it seems reasonable to assume that at the time when they become proerythroblasts not all cells incorporate exactly the same amount of TfRs on the surface, but that there is some distribution of this attribute among the cells (Assumption 14). Thus, the concept for the boundary includes, that $$\int_{\tau_{min}^s}^{\tau_{max}^s} \eta(\tau) d\tau = 1,$$

where, for instance, $\eta(\tau)$ can be chosen such that the structural variable $\tau$ is normally distributed with a certain mean value and variance. For an illustration of this situation see FIG. 7.

The revisited population equation for marrow reticulocytes reads $$\begin{cases} \frac{\partial}{\partial t} s(t, \mu^s, h^s, \tau^s)) + v_1^s(E(t)) \frac{\partial}{\partial \mu^s} s(t, \mu^s, h^s, \tau^s) + \\ \quad v_2^s(\tau^s, a_1(t)) \frac{\partial}{\partial h^s} s(t, \mu^s, h^s, \tau^s)), \\ + \frac{\partial}{\partial \tau^s} (v_3^s(\mu^s, h^s, \tau^s) s(t, \mu_{min}^s, h^s, \tau^s)) = -\alpha^s(\mu^s, h^s) s(t, \mu^s, h^s, \tau^s), \\ v^s(E(t)) s(t, \mu_{min}^s, h^s, \tau^s) = r(t, \mu_{max}^r, h^r, \tau^r), \\ s(0, \mu^s, h^s, \tau^s) = s_0(\mu^s, h^s, \tau^s), \end{cases}$$

where $s(t,\mu^s,h^s,\tau^s)$ is the population density of the marrow reticulocytes class at time t with maturity $\mu^s$, amount of hemoglobin $h^s$ and number of TfRs $\tau^s$, $13=\mu_{min}^s \leq \mu^s \leq \mu_{max}^s=15$, $h_{min}^s \leq h^s \leq h_{max}^s$, $\tau_{min}^s \leq \tau^s \leq \tau_{max}^s$, $t>0$. The boundary condition $v^s(E(t))s(t,\mu_{min}^s,h^s,\tau^s)=r(t,\mu_{max}^r,h^r,\tau^r)$ describes the flux of cells leaving the erythroblast class and entering the reticulocytes population class carrying a certain amount of hemoglobin and expressing a certain number of TfRs. Finally, $s_0(\mu^s,h^s,\tau^s)$ is the population density at $t=0$.

A sigmoid function is used to describe the changes in the maturation velocity $v_\mu^s$, $$v_1^s(E(t)) = \frac{a_5 - b_5}{1 + e^{-k_5 E(t) + c_5}} + b_5,$$

where E(t) is the EPO concentration at time t and $a_5$, $b_5$, $c_5$ and $k_5$ are some positive constants with $a_5 > b_5$. The maturation velocity increases with a rising concentration of EPO (Assumption 10). Note, a slower maturation velocity causes the cells to reach the maximum cell age $\mu_{max}^s$ at a later point, whereas a faster maturation velocity shortens the transit time, i.e., the cells reach $\mu_{max}^s$ earlier. The change of the amount of hemoglobin $v_h^s$ in a cell, the development of TfRs $v_\tau^s$ on the cell surface and the rate of apoptosis $\alpha^s$ are described with the same functions as for the erythroblast class, i.e.

$$v_2^s(\tau, a_1) = v_2^r(\tau, a_1), v_3^s(\mu, h, \tau) = v_3^r(\mu, h, \tau), \alpha^s(\mu, h) = \alpha^r(\mu, h).$$

Further, $\beta^s \equiv 0$ because of Assumption 22.

So far, Assumption 19 has not been accounted for. The assumption can be applied in the following way: If $E(t) > E^*$ the reticulocyte class is skipped and erythroblasts with maximal maturity directly enter the erythrocytes class.

2.1.3. Erythrocytes.
Assumptions:
24. Erythrocytes and blood reticulocytes are subsumed in one class.
25. Cells mature but do not proliferate.
26. There is a fixed random daily break-down of red blood cells (not to be confused with loss of erythrocytes due to senescence).
27. A drop in EPO concentration beneath a threshold precipitates neocytolysis.
28. Erythrocytes with age between 14-21 days are likely to be affected by neocytolysis.
29. Erythrocytes lose hemoglobin during senescence.
30. The expected life span of normochromic cells in healthy persons is 120 days, but can decrease significantly in uremic patients.
31. Cells in which hemoglobin content drops beneath a certain threshold or which reach the maximum cell age are phagocytosed.

Up to this point, it has been assumed that red blood cells carry approximately the same amount of hemoglobin. This assumption is not valid in many pathologies, different types of anemia, and the majority of dialysis patients, where a wide distribution of corpuscular hemoglobin can be observed. Additionally, it is desirable to account for hemoglobin which is lost during senescence. This loss, which amounts to about 15-20%, is a non-negligible amount of iron that flows back to the macrophages. See S. C. Gifford, J. Derganc, Y. Shevkoplyas, S. S. Yoshida, and M. W. Bitensky, British Journal of Haematology, 135:395-404, 2006; F. L. Willekens, F. H. Bosch, B. Roerdinkholder-Stoelwinder, Y. A. Groenen-Döpp, and J. M. Were, European Journal of Haematology, 58:246-250, 1997; J. M. Werre, F. Willekens, F. H. Bosch, L. D. de Haans, S. G. van der Vegt, A. G. van den Bos, and G. J. Bosman, Cellular and Molecular Biology 50 (2), 139-145, 2004; F. L. Willekens, B. Roerdinkholder-Stoelwinder, Y. A. Groenen-Döpp, H. J. Bos, G. J. Bosman, A. G. van den Bos, A. J. Verkleij, and J. M. Were, Blood, 101:747-751, 2003. Further, the binding of oxygen is pivotal for delivery of oxygen by hemoglobin, and thus a reduction of 15-20% in the hemoglobin mass will have a noticeable impact on the oxygen carrying capacity. Hence, there are several good reasons that suggest including hemoglobin content $h^m$ as a structural variable. Further, the attribute $h^m$ allows one to relatively easily compute the amount of iron which is set free when an erythrocyte is phagocytosed. Moreover, it enables tracking of how much iron is set free daily because of shedding of hemoglobin containing vesicles.

Altogether, the following equation is obtained for erythrocytes:

$$\begin{cases} \frac{\partial}{\partial t} m(t, \mu^m, h^m)) + \frac{\partial}{\partial \mu^m} m(t, \mu^m, h^m) + v_2^m(\mu^m) \frac{\partial}{\partial h^m} m(t, \mu^m, h^m), \\ = -\alpha^m(E(t), \mu^m, h^m), m(t, \mu^m), \\ m(t, \mu^m, h_{min}^m) = 0, \\ m(t, 0, h^m) = \begin{cases} v^s(E(t)) \int_{\tau_{min}^s}^{\tau_{max}^s} s(t, \mu_{max}^s, h^s, \tau^s) d\tau^s & \text{for } E(t) \leq E^*, \\ \int_{\tau_{min}^r}^{\tau_{max}^r} r(t, \mu_{max}^r, h^r, \tau^r) d\tau^r & \text{for } E(t) > E^*, \end{cases} \\ m(0, \mu^m, h^m) = m_0(\mu^m, h^m), \end{cases}$$

where $m(t,\mu^m,h^m)$ is the population density for the erythrocyte class at time t with maturity $\mu^m$ and cell hemoglobin $h^m$, $0 = \mu_{min}^m \leq \mu^m \leq \mu_{max}^m = 120$, $h_{min}^m \leq h^m \leq h_{max}^m$ and $t \geq 0$ and $m_0(\mu^m,h^m)$ is the population density at $t=0$. Moreover, $m(t, 0, h^m)$ is defined by the number of reticulocytes or the number of erythroblasts entering the blood stream carrying a certain amount of hemoglobin $h^m$, respectively. To describe the corpuscular hemoglobin decay, a function $v_h^m$ is used, of the form $$v_2^m(\mu^m) = b_6(\mu^m - \mu_*^m)^2 - c_6,$$

with $b_6, c_6, \mu_*^m > 0$ constant. Choosing appropriate constants $b_6, c_6$ and $\mu_*^m$ allows for a wide range of possible forms of the function $h^m(t)$, with $dh^m(t)/dt = v_2^m(\mu^m(t))$.

The mortality rate $\alpha^m(E(t),\mu^m,h^m)$ is the sum of three terms:

1. The rate of cells dying due to senescence, which is assumed to happen when the cell reaches the maximal cell age $\mu_{max}^m$ or the minimal hemoglobin content $h_{min}^m$ (Assumption 30).
2. Cells dying because of random break-down.
3. Cells dying because of neocytolysis.

Altogether, $$\alpha^m(E(t), \mu^m, h^m) = \begin{cases} \gamma^m(\mu^m, h^m) + \min(c_E/E(t)^{k_E}, b_E) & \text{for } E(t) < \tau_E, \mu_{min}^{m,n} \leq \mu^m \leq \mu_{max}^{m,n}, \\ \gamma^m(\mu^m, h^m) & \text{otherwise,} \end{cases}$$

where $b_E, c_E, k_E$ are positive constants, $\tau_E$ is the threshold beneath which neocytolysis is triggered (Assumption 27). Further, $[\mu_{min}^{m,n}, \mu_{max}^{m,n}] = [14,21]$ is the age-interval during which cells are affected by neocytolysis (Assumption 28) and $t \geq 0$. Since it is assumed that a cell is phagocytosed when it reaches the maximal cell age $\mu_{max}^m$ or the minimal cell hemoglobin $h_{min}^m$, the mortality rate $\gamma^m(\mu^m, h^m)$ needs to be chosen such that $\gamma^m(\mu^m, h^m) = \alpha_{rand}^m$ for $\mu_{min}^m \leq \mu^m \leq \mu_{max}^m - \delta$, $h_{min}^m + \delta \leq h^m \leq h_{max}^m$ with $\delta > 0$ sufficiently small and $\int_{\mu_{max}^m - \delta}^{\mu_{max}^m} \int_{h_{min}^m}^{h_{min}^m + \delta} \alpha^m(\mu, h) d\mu dh = \infty$. Here, $\alpha_{rand}^m$ denotes the random breakdown of cells (Assumption 26). A possible choice for $\gamma^m(\mu^m, h^m)$ is $$\gamma^m(\mu^m, h^m) = \begin{cases} \alpha_r^m & \text{for } \mu^m \in [\mu_{min}^m, \mu_{max}^m - \delta], h^m \in [h_{min}^m + \delta, h_{max}^m], \\ \gamma_\mu^m(\mu^m)\gamma_h^m(h^m) & \text{for } \mu^m \in (\mu_{max}^m - \delta, \mu_{max}^m), h^m \in (h_{min}^m, h_{min}^m + \delta), \\ \infty & \text{for } \mu^m \geq \mu_{max}^m, h^m \leq h_{min}^m, \end{cases}$$

where $$\gamma_\mu^m(\mu^m) = \frac{3\alpha_{rand}^m \delta^2}{(\mu^m)^2 - 2(\mu_{max}^m + \delta)\mu^m + (\mu_{max}^m + 2\delta)\mu_{max}^m},$$

and $$\gamma_h^m(h^m) = \frac{3\delta^2}{(h^m)^2 - 2(h_{min}^m - \delta)h^m + (h_{min}^m - 2\delta)h_{max}^m},$$

In case of bleeding an additional term $\alpha_{bleed}^m(t)$ needs to be added. What this term looks like depends on whether the bleeding lasts minutes or hours or is prolonged for several days or weeks.

2.1.4. Erythropoietin.

Assumptions:

32. Release of EPO is controlled by a negative feedback mechanism according to the oxygen content.
33. Oxygen carrying capacity is directly proportional to the amount of hemoglobin of circulating red blood cells.
34. The degradation rate of EPO is constant.
35. There is a slight delay in reaction of the EPO production rate to the number of RBCs but this is negligible compared to the duration of development of erythrocytes.

The equation which describes the release of EPO by the kidneys is $$E_{in}^{end}(t) = \frac{a_7 - b_7}{1 + e^{k_7 \tilde{H}b(t) - c_7}} + b_7,$$

where $\tilde{H}b(t) = Hb(t)/TBV$ is the hemoglobin concentration. Here, TBV is the total blood volume and $Hb(t) = \int_{h_{min}^m}^{h_{max}^m} m(t,\mu^m,h^m) dh^m$ is the total amount of hemoglobin in blood. Furthermore, $a_7, b_7, c_7$ and $k_7$ are positive constants with $a_7 > b_7$.

The dynamics of the endogenous EPO concentration $E^{end}(t)$ are described by the following ordinary differential equation:

$$\dot{E}^{end}(t) = \frac{1}{TBV} E_{in}^{end}(t) - c_{deg}^{end} E^{end}(t),$$

where $E^{end}(t)$ is the endogenous EPO concentration, $E_{in}^{end}$ is the amount of EPO released by the kidneys and $c_{deg}^{end}$ describes the degradation rate of endogenous EPO. The change in the concentration $E^{ex}(t)$ of an ESA reads $$\dot{E}^{ex}(t) = \frac{1}{TBV} E_{in}^{ex}(t) - c_{deg}^{ex} E^{ex}(t),$$

where $E_{in}^{ex}(t)$ is the rate at which the artificial hormone is administered $c_{deg}^{ex}$ is the rate with which the exogenous hormone is degraded. In intravenous administration, the total amount of the agent is injected into a vein, within a very short time interval. In this case $E_{in}^{ex}(t)$ can be approximated by $E_0^{ex}(t)\delta_{t_0}(t)$, where $E_0^{ex}$ is the amount of artificial hormone administered and $\delta_{t_0}(t)$ is the Dirac delta impulse located at $t_0$, the time when the administration takes place. In addition, the degradation rate for exogenous EPO $c_{deg}^{ex}$ differs from the one for endogenous EPO and varies according to the kind of ESA administered. The overall concentration of EPO in plasma consists of the naturally produced erythropoietin in the body and the administered ESA $$E(t) = E^{ex}(t) + E^{end}(t).$$

3. The Iron Submodel.

Assumptions:

37. Five iron pools are considered within the body: a plasma pool, iron in precursor cells, iron in erythrocytes, iron in the macrophages and a storage pool.
38. Other iron in the body is ignored.
39. Hepcidin regulates iron homeostasis.
40. Stressed erythropoiesis and depleted stores decrease the amount of hepcidin released into plasma.
41. Large iron stores and inflammation increase hepcidin levels.
42. The amount of iron in plasma is proportional to the amount of transferrin molecules carrying iron. (Free iron is neglected.)
43. No distinction is made between monoferric and differic transferrin.

44. Iron is lost via loss of cells.

45. Iron lost via urine and sweat is neglected.

Iron is a part of hemoglobin which provides the means of $O_2$ transport to the tissue. The rate at which iron can be released to plasma from existing stores and macrophages may easily limit the rate of iron delivery for hemoglobin synthesis. Therefore, a strong relationship between impaired erythropoiesis and total body iron burden exists. An excellent description of iron homeostasis and its effects can be found in Crichton.

Iron is a substance which is very tightly controlled from the body as iron overload is toxic. Iron homeostasis can be only achieved by the control of absorption because the human body, unlike other mammals, is not able to influence the excretion of iron.

Under normal circumstances the average daily loss of iron is very small (men: 1 mg, women: 2 mg, because of menstruation or pregnancy).

Figure 8:
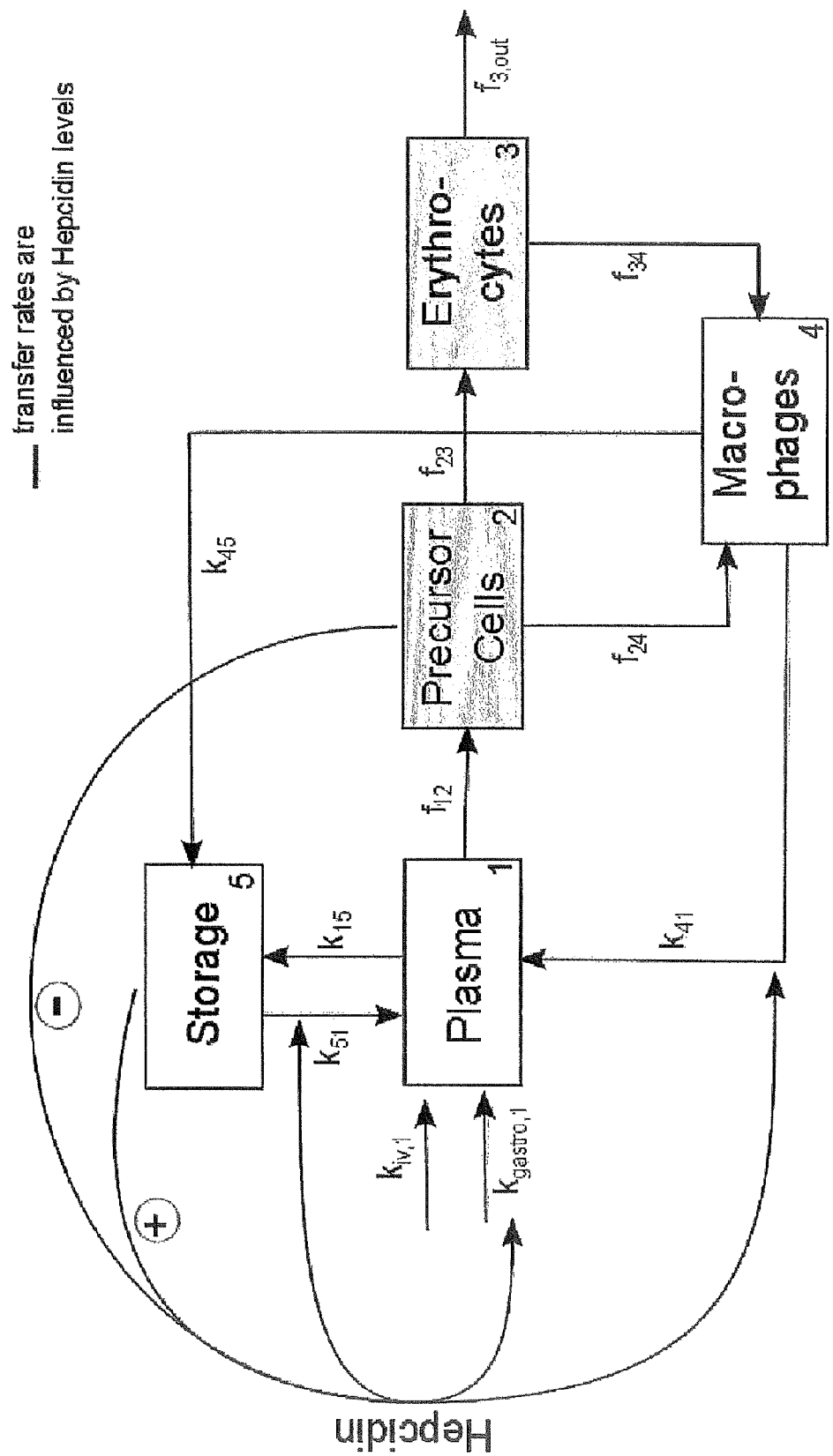
FIG. 8 is a schematic illustration of the organizational diagram of the iron submodel.

For the iron submodel, five dynamic iron pools are considered within the body: a plasma pool, iron in precursor cells, iron in erythrocytes, iron in the macrophages and a storage pool. Hence, ferritin and hemosiderin stores are combined. Other iron in the body is ignored. For an illustration of the organizational structure of the iron submodel see FIG. 8. The amount of iron lost via urine and sweat is neglected. Thus, in this model, excretion of iron takes place only when cells are lost. On one hand, this can be due to loss of RBCs, i.e., due to external bleeding, and on the other hand there is a daily loss of epithelial cells, which amount for about 1 mg/day. Further, it is assumed that only the precursor cells in the bone marrow uptake iron and ineffective erythropoiesis depends on the amount of iron which can be provided for erythropoiesis. Moreover, the model accounts for the loss of iron from erythrocytes during senescence.

The general form of the compartmental iron model is as follows:

$$\frac{d}{dt}a_1 = k_{41}(H)a_4 + k_{iv,1}a_{iv} + k_{gastro,1}(H)a_{gastro} + k_{51}(H)a_5 - k_{15}a_1 - k_{12}a_1,$$

$$\frac{d}{dt}a_2 = k_{12}a_1 - f_{24} - f_{23},$$

$$\frac{d}{dt}a_3 = f_{23} - f_{34} - f_{3,out},$$

$$\frac{d}{dt}a_4 = f_{24} + f_{34}a_3 - k_{41}(H)a_4 - k_{45}a_4,$$

$$\frac{d}{dt}a_5 = k_{15}a_1 + k_{45}a_4 - k_{51}(H)a_5.$$

Note, in the above equations, the dependence of particular components on t was not explicitly stated to simplify notation. Furthermore, $a_i$, i=1, . . . , 5, denotes the amount of iron in the compartment i and $k_{ij}$, i, j=1, . . . , 5 are the transfer rates from compartment i to compartment j, i.e., $k_{ij}a_i$ is the rate at which iron is moving from compartment i to compartment j. Further, $f_{ij}$ denote the rates at which iron is transferred from compartment i into compartment j, when it is not of the simple form $k_{ij}a_i$; $f_{3,out}$ is the amount of iron which is lost by bleeding. Additionally, $a_{iv}$ denotes the amount of iron intravenously administered, whereas $a_{gastro}$ is the amount of iron in the duodenum. Finally, $k_{iv,1}$ and $k_{gastro,1}(H)$ are the corresponding flow rates. The rate $k_{gasto,1}$ can be described by a decreasing sigmoidal function $$k_{gastro,1}(H(t)) = \frac{a_8 - b_8}{1 + e^{-k_8 H(t) + c_8}} + b_8,$$

where $a_8$, $b_8$, $c_8$ and $k_8$ are positive constants with $a_8 > b_8$. The function H(t) is the solution of the differential equation (5).

Since the time needed to administer iron is very short compared to other time constants in the system, the following can be taken $$k_{iv,1}a_{iv} = a_{iv,total}\delta_{t_0}.$$

Here $a_{iv,total}$ is the total amount of iron administered and $\delta_{t_0}$ is the Dirac delta function located at $t_0$.

3.1. Hepcidin Feedback.

The regulator of iron homeostasis is hepcidin, a peptide hormone produced by the liver. Hepcidin negatively regulates the availability of iron in plasma by binding to ferroportin on the membranes of iron-exporting cells. Hepcidin binding induces the endocytosis and proteolysis of ferroportin, and thereby decreases the delivery of iron to the plasma. See Nemeth E., Tuttle M. S., Powelson J., Vaughn M. B., Donovan A., Ward D. M., Ganz T., and Kaplan J., Science 306 pp. 2090-2093 (2004). Ferroportin is the iron exporter required for iron egress from iron exporting cells, as for instance, enterocytes and macrophages. Hepcidin acts as a medium to withhold iron from certain invasive bacteria, as they are not able to proliferate under conditions of insufficient iron supply. The dynamics of the hepcidin concentration in plasma is calculated according to $$\frac{d}{dt}H(t) = \frac{1}{TBV}H_{prod}(t) - c_{deg}^H H(t), \qquad (5)$$

where $H_{prod}(t)$ is the rate at which hepcidin, produced by the hepatocytes, is released into the plasma at time t. TBV is the total blood volume, and $c_{deg}^H$ is the rate at which hepcidin is degraded. The production rate $H_{prod}(t)$ of hepcidin is obtained as the result of a feedback loop involving the total precursor cell population, the amount of iron stored and the state of inflammation of the patient $$H_{prod}(t) = f(U(t), a_5(t), i(t)).$$

Here $$U(t) = \int_{\mu_{min}^r}^{\mu_{max}^r}\int_{h_{min}^r}^{h_{max}^r}\int_{\tau_{min}^r}^{\tau_{max}^r} r(t, \mu^r, h^r)d\mu^r dh^r d\tau^r + \int_{\mu_{min}^s}^{\mu_{max}^s}\int_{h_{min}^s}^{h_{max}^s}\int_{\tau_{min}^s}^{\tau_{max}^s} s(t, \mu^s, h^s)d\mu^s dh^s d\tau^s,$$

where U(t) describes the total precursor cell population (erythroblasts+reticulocytes). Further, $a_5(t)$ is the amount of iron stored and i(t) is the inflammation status at time t. The feedback is modeled using a monotonically increasing sigmoidal function $$H_{prod}(t) = \frac{a_H - b_H}{1 + e^{-k_H C(t) + c_H}} + b_H,$$

where $a_H$, $b_H$, $c_H$ and $k_H$ are positive constants with $a_H > b_H$. The function $$C(t) = -c_U U(t) + c_{a_5} a_5(t) + c_i i(t),$$

is an auxiliary equation that increases if storage amount or inflammation status rises, and decreases when more RBCs are produced. Here, $c_U$, $c_{a_5}$ and $c_i$ are positive constants.

3.2. Detailed Description of the Iron Compartments.

3.2.1. Plasma (Compartment 1).

The rate at which iron enters erythroid cells at time t is given by $$d_0 a_1(t) \left( \int_{\mu_{min}^r}^{\mu_{max}^r} \int_{h_{min}^r}^{h_{max}^r} \int_{\tau_{min}^r}^{\tau_{max}^r} \tau^r r(t, \mu^r, h^r) d\mu^r dh^r d\tau^r + \int_{\mu_{min}^s}^{\mu_{max}^s} \int_{h_{min}^s}^{h_{max}^s} \int_{\tau_{min}^s}^{\tau_{max}^s} \tau^s s(t, \mu^s, h^s) d\mu^s dh^s d\tau^s \right),$$

where $r(t,\mu^r,\tau^r,h^r)$ and $s(t,\mu^s,\tau^s,h^s)$ denote the population densities of hemoglobin synthesizing cells, erythroblasts and reticulocytes, respectively. At the same time this is the rate at which iron leaves the plasma compartment and enters the precursor cell compartment.

Only a very small amount of iron can be found in this pool (about 3 mg; ≤1%) bound to transferrin, but it is a very important compartment because of its rapid turnover rate. See Finch 1982. Iron normally turns over at least 10 times each day. See Williams Hematology. Inflow into the plasma compartment comes from macrophages, the storage pool, iron absorbed through the duodenum and via intravenously administered iron. Outflow leaves the plasma compartment to the precursor cells and the storage compartment. The flow rates $k_{41}$, $k_{gastro,1}$ and $k_{51}$ are dependent on the hepcidin concentration $H(t)$ at time t. They decrease when the hepcidin level rises and vice versa. Inflammation and full iron stores increase the release of hepcidin from the hepatocytes in the liver, whereas a stressed erythropoiesis and depleted stores suppress the production of hepcidin. The outflow to the precursor cell compartment $k_{12}a_1$ is altered by the amount of iron needed from the cells to synthesize hemoglobin. As erythroid cells are only able to take up iron through transferrin receptors, their need for iron can be associated with the number of receptors expressed on precursor cells. Thus, the rate $k_{12}$ is given by $$k_{12} = d_0 \left( \int_{\mu_{min}^r}^{\mu_{max}^r} \int_{h_{min}^r}^{h_{max}^r} \int_{\tau_{min}^r}^{\tau_{max}^r} \tau^r r(t, \mu^r, h^r) d\mu^r dh^r d\tau^r + \int_{\mu_{min}^s}^{\mu_{max}^s} \int_{h_{min}^s}^{h_{max}^s} \int_{\tau_{min}^s}^{\tau_{max}^s} \tau^s s(t, \mu^s, h^s) d\mu^s dh^s d\tau^s \right),$$

For an explanation of the various terms see the statements concerning erythroblasts in Subsection 2.1.2. Hence, the change of amount of iron in the plasma compartment is $$\frac{d}{dt} a_1(t) = k_{41}(H(t)) a_4(t) + a_{iv,total}(t)\delta_{t_0}(t) + k_{gastro,1}(H(t)) a_{gastro}(t) +$$

-continued $$k_{51}(H(t)) a_5(t) - k_{15} a_1(t) - d_0 \left( \int_{\mu_{min}^r}^{\mu_{max}^r} \int_{h_{min}^r}^{h_{max}^r} \int_{\tau_{min}^r}^{\tau_{max}^r} \tau^r r(t, \mu^r, h^r) d\mu^r dh^r d\tau^r + \int_{\mu_{min}^s}^{\mu_{max}^s} \int_{h_{min}^s}^{h_{max}^s} \int_{\tau_{min}^s}^{\tau_{max}^s} \tau^s s(t, \mu^s, h^s) d\mu^s dh^s d\tau^s \right) a_1(t).$$

The transfer rate $k_{41}(H(t))$ and $k_{51}(H(t))$ can be described by monotonically decreasing sigmoidal functions $$k_{41}(H(t)) = \frac{a_9 - b_9}{1 + e^{-k_9 H(t) + c_9}} + b_9, \tag{6}$$

and $$k_{51}(H(t)) = \frac{a_{10} - b_{10}}{1 + e^{-k_{10} H(t) + c_{10}}} + b_{10}, \tag{7}$$

respectively. The parameters $a_9$, $b_9$, $c_9$, $k_9$, $a_{10}$, $b_{10}$, $c_{10}$ and $k_{10}$ are positive constants with $a_9 > b_9$ and $a_{10} > b_{10}$. The hepcidin level $H(t)$ at time t is determined by equation (5).

3.2.2. Precursor Cells (Compartment 2).

Inflow into the precursor cell compartment comes from plasma. One outflow of this compartment leaves to the erythrocytes compartment and describes the amount of hemoglobin carried from reticulocytes, which enter the blood stream. Thus, the flow $f_{23}(\cdot)$ from compartment 2 to compartment 3, is defined by the cells that leave the bone marrow and the amount of hemoglobin these cells are carrying. These quantities can be calculated from the population model and $$k_{23} a_2 = f_{23}(v^s(E(t))s(t,\mu_{max}^s,\tau^s),h^s(\mu_{max}^s)),$$

where $v^s(E(t))s(t,\mu_{max}^s,\tau^s)$ determines how many cells are leaving the bone marrow at a certain time t and the distribution function $h^s(\mu_{max}^s)$ at the maximum maturity level $\mu_{max}^s$ indicates how much hemoglobin they carry. Here $v^s(E(t))$ is the maturation velocity of reticulocytes depending on EPO, $s(t,\mu_{max}^s,\tau^s)$ is the density of reticulocyte population with maximal maturity $\mu_{max}^s$, and $\tau^s \in [\tau_{min}^s,\tau_{max}^s]$ is the number of transferrin receptors at time t. The hemoglobin distribution function $h^s(\mu_{max}^s)$ arises as a result of the population model, in particular the precursor cell population part.

The second outflow of this compartment leaves to the macrophages and is defined by the precursor cells that die. Hence, the flow from compartment 2 to compartment 4 is defined by the amount of iron that dying cells carry, i.e., $$k_{24} a_4 = \int_{\mu_{min}^r}^{\mu_{max}^r} \int_{h_{min}^r}^{h_{max}^r} \int_{\tau_{min}^r}^{\tau_{max}^r} h^r \alpha^r(\mu^r, h^r) r(t, \mu^r, h^r) d\mu^r dh^r d\tau^r + \int_{\mu_{min}^s}^{\mu_{max}^s} \int_{h_{min}^s}^{h_{max}^s} \int_{\tau_{min}^s}^{\tau_{max}^s} h^s \alpha^s(\mu^s, h^s) s(t, \mu^s, h^s) d\mu^s dh^s d\tau^s, \tag{8}$$

where $r(t,\mu^r,\tau^r)$ and $s(t,\mu^s,h^s)$ are the densities of the two precursor cell populations. Further, $\mu^i \in [\mu_{min}^i,\mu_{max}^i]$ denotes the maturity, $h^i \in [h_{min}^i,h_{max}^i]$ denotes the amount of hemoglobin carried by a cell and $\tau^i \in [\tau_{min}^i,\tau_{max}^i]$ denotes the number of transferrin receptors for i=r, s. The function $\alpha^i(\mu^i,h^i)$, i=r, s describes the mortality rate of precursor cells, where $\alpha^r = \alpha^s$ is determined by equations (3) and (4).

Altogether the change of amount of iron in the iron-precursors compartment is given by $$\frac{d}{dt}a_2(t) = d_0\left(\int_{\mu_{min}^r}^{\mu_{max}^r}\int_{h_{min}^r}^{h_{max}^r}\int_{\tau_{min}^r}^{\tau_{max}^r}\tau^r r(t,\mu^r,h^r)d\mu^r dh^r d\tau^r + \int_{\mu_{min}^s}^{\mu_{max}^s}\int_{h_{min}^s}^{h_{max}^s}\int_{\tau_{min}^s}^{\tau_{max}^s}\tau^s s(t,\mu^s,h^s)d\mu^s dh^s d\tau^s\right)a_1(t) -$$
$$f_{23}(v^s(E(t))s(t,\mu_{max}^s,\tau^s),h^s(\mu_{max}^s)) -$$
$$\int_{\mu_{min}^r}^{\mu_{max}^r}\int_{h_{min}^r}^{h_{max}^r}\int_{\tau_{min}^r}^{\tau_{max}^r}h^r\alpha^r(\mu^r,h^r)r(t,\mu^r,h^r)d\mu^r dh^r d\tau^r +$$
$$\int_{\mu_{min}^s}^{\mu_{max}^s}\int_{h_{min}^s}^{h_{max}^s}\int_{\tau_{min}^s}^{\tau_{max}^s}h^s\alpha^s(\mu^s,h^s)s(t,\mu^s,h^s)d\mu^s dh^s d\tau^s.$$

Note that it is not necessary to determine the function $f_{23}$, because there is no need to explicitly observe the rate of change of the precursor cell compartment. The amount of iron $a_2(t)$ in this compartment at time t can be directly computed from the population classes. It is defined by the total number of precursor cells and the amount of hemoglobin they carry:

$$a_2(t) = \int_{\mu_{min}^r}^{\mu_{max}^r}\int_{h_{min}^r}^{h_{max}^r}\int_{\tau_{min}^r}^{\tau_{max}^r}h^r r(t,\mu^r,h^r)d\mu^r dh^r d\tau^r +$$
$$\int_{\mu_{min}^s}^{\mu_{max}^s}\int_{h_{min}^s}^{h_{max}^s}\int_{\tau_{min}^s}^{\tau_{max}^s}h^s s(t,\mu^s,h^s)d\mu^s dh^s d\tau^s.$$

However, it is important to know the flux of hemoglobin to the macrophage compartment which arises from dying cells, because this flux (see equation (8)) is a source term in the macrophage compartment.

3.2.3. Erythrocytes (Compartment 3).

Inflow into the erythrocytes compartment comes from the precursor cell compartment, and iron leaves the compartment to the macrophages compartment (phagocytosis of senescent cells, random break-down of cells and neocytolysis, shedding of hemoglobin containing vesicles)

$$k_{34}a_3 = \int_{\mu_{min}^m}^{\mu_{max}^m}\int_{h_{min}^m}^{h_{max}^m}h^m\alpha^m(E(t),\mu^m,h^m)m(t,\mu^m,h^m)d\mu^m dh^m + \int_{\mu_{min}^m}^{\mu_{max}^m}\int_{h_{min}^m}^{h_{max}^m}v_2^m(\mu^m)m(t,\mu^m,h^m)d\mu^m dh^m, \quad (9)$$

or is excreted via bleeding $$k_{3,out}a_3 = \int_{\mu_{min}^m}^{\mu_{max}^m}\int_{h_{min}^m}^{h_{max}^m}h^m\alpha_{bleed}^m(t)m(t,\mu^m,h^m)d\mu^m dh^m.$$

Here $\alpha^m$ denotes the mortality rate of erythrocytes due to phagocytosis of senescent cells, random break-down of cells and neocytolysis. Furthermore, $h^m$ is the amount of hemoglobin carried by a cell, $m(t,\mu^m,h^m)$ is the population density of erythrocytes with cell age $\mu^m$ and cellular hemoglobin $h^m$ at time t and $\alpha_{bleed}^m(t)$ is the rate with which RBCs are lost due to bleeding. Thus, the change of amount of iron in the erythrocyte compartment is $$\frac{d}{dt}a_3(t) = f_{23}(v^s(E(t))s(t,\mu_{max}^s,\tau^s),h^s(\mu_{max}^s)) -$$
$$\int_{\mu_{min}^m}^{\mu_{max}^m}\int_{h_{min}^m}^{h_{max}^m}h^m\alpha_{bleed}^m(t)m(t,\mu^m,h^m)d\mu^m dh^m -$$
$$\int_{\mu_{min}^m}^{\mu_{max}^m}\int_{h_{min}^m}^{h_{max}^m}h^m\alpha^m(E(t),\mu^m,h^m)m(t,\mu^m,h^m)d\mu^m dh^m -$$
$$\int_{\mu_{min}^m}^{\mu_{max}^m}\int_{h_{min}^m}^{h_{max}^m}v_2^m(\mu^m)m(t,\mu^m,h^m)d\mu^m dh^m.$$

Similar to compartment 2, it is not necessary to observe the rate of change of the erythrocyte cell compartment to compute the amount of iron $a_3(t)$ at time t. The quantity $a_3(t)$ can be directly computed from the population class and is defined by the total number of circulating red blood cells and the amount of hemoglobin they carry:

$$a_3(t) = \int_{\mu_{min}^m}^{\mu_{max}^m}\int_{h_{min}^m}^{h_{max}^m}h^m m(t,\mu^m,h^m)dh^m d\mu^m.$$

However, the term $k_{34}a_3(t)$ needs to be known explicitly (see equation (9)). This flux, which is the rate of hemoglobin released by erythrocytes, appears as a source term in the macrophage compartment.

3.2.4. Macrophages (Compartment 4).

Inflow into the macrophages compartment comes from the erythrocytes compartment (erythrocytes phagocytosed by macrophages, iron set free by random break-down of RBCs and shedding of hemoglobin containing vesicles) and the precursor cells compartment. Outflow of this compartment leaves to the plasma and to the storage compartment. Therefore, the change of iron in the compartment is $$\frac{d}{dt}a_4(t) = \int_{\mu_{min}^m}^{\mu_{max}^m}\int_{h_{min}^m}^{h_{max}^m}h^m\alpha^m(E(t),\mu^m,h^m)m(t,\mu^m,h^m)d\mu^m dh^m +$$
$$\int_{\mu_{min}^m}^{\mu_{max}^m}\int_{h_{min}^m}^{h_{max}^m}v_2^m(\mu^m)h^m m(t,\mu^m,h^m)d\mu^m dh^m +$$
$$\int_{\mu_{min}^r}^{\mu_{max}^r}\int_{h_{min}^r}^{h_{max}^r}\int_{\tau_{min}^r}^{\tau_{max}^r}h^r r(t,\mu^r,h^r)d\mu^r dh^r d\tau^r +$$
$$\int_{\mu_{min}^s}^{\mu_{max}^s}\int_{h_{min}^s}^{h_{max}^s}\int_{\tau_{min}^s}^{\tau_{max}^s}h^s s(t,\mu^s,h^s)d\mu^s dh^s d\tau^s -$$
$$k_{41}(H(t))a_4(t) - k_{45}a_4(t),$$

where $k_{41}(H(t))$ is given by equation (6).

3.2.5. Storage (Compartment 5.)

Inflow into the storage compartment comes from the plasma and the macrophages compartment and iron leaves this compartment to the plasma compartment. Hence, the change of iron in the storage compartment is $$\frac{d}{dt}a_5(t) = k_{15}a_1(t) + k_{45}a_4(t) - k_{51}(H(t))a_5(t),$$

where $k_{51}(H(t))$ is given in equation (7).

The iron submodel can be applied independently of erythropoiesis to a variety of iron disorders, such as true iron deficiency states (e.g., bleeding, malabsorption), functional iron deficiencies (e.g., anemias of chronic disease, usually with chronic inflammatory disorders or malignancies), or iron overload disorders (e.g., all forms of hemochromatosis, iron intoxication, polytransfusions of blood, chronic hepatopathies, and hyper plastic erythroid disorders such as thalassemias).

4. A Complete Listing of the Equations for the Mathematical Model.

The model consists of the following structured population equations using the symbols defined in FIG. 9:

$$\frac{\partial}{\partial t} p(t, \mu^p) + \frac{\partial}{\partial \mu^p} p(t, \mu^p) = \beta^p p(t, \mu^p),$$

$$\frac{\partial}{\partial t} q(t, \mu^q) + \frac{\partial}{\partial \mu^q} q(t, \mu^q) = (\beta^q - \alpha^q(E(t))) q(t, \mu^q),$$

$$\frac{\partial}{\partial t} r(t, \mu^r, h^r, \tau^r) + \frac{\partial}{\partial \mu^r} r(t, \mu^r, h^r, \tau^r) + v_2^r(\tau, a_1(t)) \frac{\partial}{\partial h^r} r(t, \mu^r, h^r, \tau^r),$$

$$+ \frac{\partial}{\partial \tau^r} (v_3^r(\mu^r, h^r, \tau^r) r(t, \mu^r, h^r, \tau^r)) =$$

$$8\beta u(t, \mu^r, 2h^r, 2\tau^r) - (\beta + \alpha^r(\mu^r, h^r)) r(t, \mu^r, h^r, \tau^r),$$

$$\frac{\partial}{\partial t} s(t, \mu^s, h^s, \tau^s) + v_1^s(E(t)) \frac{\partial}{\partial \mu^s} s(t, \mu^r, h^r, \tau^r) +$$

$$v_2^s(\tau^s, a_1(t)) \frac{\partial}{\partial h^s} s(t, \mu^s, h^s, \tau^s) +$$

$$\frac{\partial}{\partial \tau^s} (v_3^s(\mu^s, h^s, \tau^s) s(t, \mu^s, h^s, \tau^s)) = -\alpha^s(\mu^s, h^s) s(t, \mu^s, h^s, \tau^s),$$

$$\frac{\partial}{\partial t} m(t, \mu^m, h^m, \tau^m) + \frac{\partial}{\partial \mu^m} m(t, \mu^m, h^m) + v_2^m(\mu_m) \frac{\partial}{\partial h^m} m(t, \mu^m, h^m) =$$

$$-\alpha^m(E(t), \mu^m, h^m) m(t, \mu^m),$$

$$\frac{d}{dt} E^{end}(t) = \frac{1}{TBV} E_{in}^{end}(t) - c_{deg}^{end} E^{end}(t),$$

$$\frac{d}{dt} E^{ex}(t) = \frac{1}{TBV} E_{in}^{ex}(t) - c_{deg}^{ex} E^{ex}(t).$$

Further, the iron model can be described as follows:

$$\frac{d}{dt} a_1(t) =$$

$$k_{41}(H(t)) a_4(t) + a_{iv,total}(t) \delta_{t_0}(t) + k_{gastro,1}(H(t)) a_{gastro}(t) + k_{51}(H(t)) a_5(t) -$$

$$k_{15} a_1(t) - d_0 \left( \int_{\mu_{min}^r}^{\mu_{max}^r} \int_{h_{min}^r}^{h_{max}^r} \int_{\tau_{min}^r}^{\tau_{max}^r} \tau^r r(t, \mu^r, h^r) d\mu^r dh^r d\tau^r + \right.$$

$$\left. \int_{\mu_{min}^s}^{\mu_{max}^s} \int_{h_{min}^s}^{h_{max}^s} \int_{\tau_{min}^s}^{\tau_{max}^s} \tau^s s(t, \mu^s, h^s) d\mu^s dh^s d\tau^s \right) a_1(t).$$

$$a_2(t) = \int_{\mu_{min}^r}^{\mu_{max}^r} \int_{h_{min}^r}^{h_{max}^r} \int_{\tau_{min}^r}^{\tau_{max}^r} h^r r(t, \mu^r, h^r) d\mu^r dh^r d\tau^r +$$

$$\int_{\mu_{min}^s}^{\mu_{max}^s} \int_{h_{min}^s}^{h_{max}^s} \int_{\tau_{min}^s}^{\tau_{max}^s} h^s s(t, \mu^s, h^s) d\mu^s dh^s d\tau^s.$$

$$a_3(t) = \int_{\mu_{min}^m}^{\mu_{max}^m} \int_{h_{min}^m}^{h_{max}^m} h^m m(t, \mu^m, h^m) dh^m d\mu^m.$$

$$\frac{d}{dt} a_4(t) = \int_{\mu_{min}^m}^{\mu_{max}^m} \int_{h_{min}^m}^{h_{max}^m} h^m \alpha^m(E(t), \mu^m, h^m) m(t, \mu^m, h^m) d\mu^m dh^m +$$

$$\int_{\mu_{min}^m}^{\mu_{max}^m} \int_{h_{min}^m}^{h_{max}^m} v_2^m(\mu^m) h^m m(t, \mu^m, h^m) d\mu^m dh^m +$$

$$\int_{\mu_{min}^r}^{\mu_{max}^r} \int_{h_{min}^r}^{h_{max}^r} \int_{\tau_{min}^r}^{\tau_{max}^r} h^r r(t, \mu^r, h^r) d\mu^r dh^r d\tau^r +$$

$$\int_{\mu_{min}^s}^{\mu_{max}^s} \int_{h_{min}^s}^{h_{max}^s} \int_{\tau_{min}^s}^{\tau_{max}^s} h^s s(t, \mu^s, h^s) d\mu^s dh^s d\tau^s -$$

$$k_{41}(H(t)) a_4(t) - k_{45} a_4(t),$$

$$\frac{d}{dt} a_5(t) = k_{15} a_1(t) + k_{45} a_4(t) - k_{51}(H(t)) a_5(t),$$

$$\frac{d}{dt} H(t) = \frac{1}{TBV} H_{prod}(t) - c_{deg}^H H(t).$$

The boundary conditions are $$p(t, 0) = S_0(E(t)),$$

$$q(t, \mu_{min}^q) = p(t, \mu_{max}^p),$$

$$r(t, \mu_{min}^r, 0, \tau^r) = q(t, \mu_{max}) \eta(\tau^r),$$

$r(t, \mu^r, h^r, \tau^r) = 0$, if $(\mu^r, h^r, \tau^r)$ is a boundary point and $h^r > 0$, $$v^s(E(t)) s(t, \mu_{min}^s, h^s, \tau^s) = r(t, \mu_{max}^r, h^r, \tau^r),$$

$$m(t, \mu^m, h_{min}^m) = 0,$$

$$m(t, 0, h^m) = \begin{cases} v^s(E(t)) \int_{\tau_{min}^s}^{\tau_{max}^s} s(t, \mu_{max}^s, h^s, \tau^s) d\tau^s & \text{for } E(t) \leq E^*, \\ \int_{\tau_{min}^r}^{\tau_{max}^r} r(t, \mu_{max}^r, h^r, \tau^r) d\tau^r & \text{for } E(t) > E^*, \end{cases}$$

and the initial values are given by
$p(0, \mu^p) = p_0(\mu^p)$,
$q(0, \mu^q) = q_0(\mu^q)$,
$r(0, \mu^r, h^r, \tau^r) = r_0(\mu^r, h^r, \tau^2)$,
$s(0, \mu^s, h^s, \tau^s) = s_0(\mu^s, h^s, \tau^s)$,
$m(0, \mu^m, h^m) = m_0(\mu^m, h^m)$,
$E^{end}(0) = E_0^{end}$,
$E^{ex}(0) = E_0^{ex}$,
$a_1(0) = a_{1,0}$,
$a_2(0) = a_{2,0}$,
$a_3(0) = a_{3,0}$,
$a_4(0) = a_{4,0}$,
$a_5(0) = a_{5,0}$,
$H(0) = H_0$.

Moreover, there are a number of auxiliary equations for the cell population model $$S_0(E(t)) = \frac{a_1 - b_1}{1 + e^{-k_1 E(t) + c_1}} + b_1,$$

$$\alpha^q(E(t)) = \frac{a_2 - b_2}{1 + e^{k_2 E(t) - c_2}} + b_2,$$

$$v_2^r(\tau^r, a_1) = d_2 \tau^r a_1,$$

$$v_3^r(\mu^r, h^r, \tau^r) = a_3 \tau^r (h_*^r - b_3(h^r)^2) - c_3 \max(\tau^r, 0)(\mu^r - \mu_{max}^q)/(1 + h^r),$$

$$\alpha^r(\mu^r, h^r) = b_4(h^{} - h^r)^2 / (1 + (\mu^{} - (\mu^r - \mu_{max}^q))^2),$$

$$\int_{\tau_{min}}^{\tau_{max}} \eta(\tau) d\tau = 1,$$

$$v_1^s(E(t)) = \frac{a_5 - b_5}{1 + e^{-k_5 E(t) + c_5}} + b_5,$$

$$v_2^s(\tau_s, a_1) = d_2 \tau^s a_1,$$

$$v_3^s(\mu^s, h^s, \tau^s) = a_3 \tau^s (h_*^s - b_3(h^s)^2) - c_3 \max(\tau^s, 0)(\mu^s - \mu_{max}^r)/(1 + h^s),$$

-continued $$\alpha^s(\mu^s, h^s) = b_4(h^{} - h^s)^2 / (1 + (\mu^{} - (\mu^s - \mu_{max}^r))^2),$$

$$v_2^m(\mu^m) = b_6(\mu^m - \mu_*^m)^2 - c_6,$$

$$\alpha^m(E(t), \mu^m, h^m) =$$

$$\begin{cases} \gamma^m(\mu^m, h^m) + \min\left(\dfrac{c_E}{E(t)^{k_E}, b_E}\right) & \text{for } \begin{array}{l} E(t) < \tau_E, \\ \mu_{min}^{m,n} \le \mu^m \le \mu_{max}^{m,n}, \end{array} \\ \gamma^m(\mu^m, h^m) & \text{otherwise,} \end{cases}$$

$$\gamma^m(\mu^m, h^m) = \begin{cases} \alpha_r^m & \text{for } \begin{array}{l} \mu^m \in [\mu_{min}^m, \mu_{max}^m - \delta], \\ h^m \in [h_{min}^m + \delta, h_{max}^m], \end{array} \\ \gamma_\mu^m(\mu^m)\gamma_h^m(h^m) & \text{for } \begin{array}{l} \mu^m \in [\mu_{max}^m - \delta, \mu_{max}^m], \\ h^m \in [h_{min}^m, h_{min}^m + \delta], \end{array} \\ \infty & \text{for } \mu^m \ge \mu_{max}^m, h^m \le h_{min}^m, \end{cases}$$

$$\gamma_\mu^m(\mu^m) = \dfrac{3\alpha_{rand}^m \delta^2}{(\mu^m)^2 - 2(\mu_{max}^m + \delta)\mu^m + (\mu_{max}^m + 2\delta)\mu_{max}^m},$$

$$\gamma_h^m(h^m) = \dfrac{3\delta^2}{(h^m)^2 - 2(h_{min}^m - \delta)h^m + (h_{min}^m - 2\delta)h_{max}^m},$$

$$E_{in}^{end}(t) = \dfrac{a_7 - b_7}{1 + e^{k_7 Hb(t)/TBV - c_7}} + b_7,$$

$$Hb(t) = \int_{\mu_{min}^m}^{\mu_{max}^m} m(t, \mu^m, h^m) d h^m,$$

$$E(t) = E^{ex}(t) + E^{in}(t),$$

and also some auxiliary equations for the iron compartment model $$k_{gastro,1}(H(t)) = \dfrac{a_8 - b_8}{1 + e^{-k_g H(t) + c_8}} + b_8,$$

$$H_{prod}(t) = \dfrac{a_H - b_H}{1 + e^{-k_H C(t) + c_H}} + b_H,$$

$$C(t) = -c_U U(t) + c_{a_5} a_5(t) + c_i i(t),$$

$$U(t) = \int_{\mu_{min}^r}^{\mu_{max}^r} \int_{h_{min}^r}^{h_{max}^r} \int_{\tau_{min}^r}^{\tau_{max}^r} r(t, \mu^r, h^r) d\mu^r dh^r d\tau^r +$$

$$\int_{\mu_{min}^s}^{\mu_{max}^s} \int_{h_{min}^s}^{h_{max}^s} \int_{\tau_{min}^s}^{\tau_{max}^s} s(t, \mu^s, h^s) d\mu^s dh^s d\tau^s,$$

$$k_{41}(H(t)) = \dfrac{a_9 - b_9}{1 + e^{-k_9 H(t) + c_9}} + b_9, \text{ and}$$

$$k_{51}(H(t)) = \dfrac{a_{10} - b_{10}}{1 + e^{-k_{10} H(t) + c_{10}}} + b_{10}.$$

Exemplification of the Above Described Models
5. Simulations for the Iron Model.

TABLE 2

Iron compartments in normal man (estimates for an average man. Height: 177 cm, weight: 70 kg. See Williams Hematology Table 40.1)

| Compartment | Iron content (mg) | Total body iron (%) |
|---|---|---|
| Hemoglobin iron (Precursors + Erythrocytes) | 2200 | 67 |
| Storage iron | 1000 | 27 |
| Labile pool (macrophages) | 80 | 2.2 |

TABLE 2-continued

Iron compartments in normal man (estimates for an average man. Height: 177 cm, weight: 70 kg. See Williams Hematology Table 40.1)

| Compartment | Iron content (mg) | Total body iron (%) |
|---|---|---|
| Transport iron (plasma) | 3 | 0.08 |
| Other tissue iron | 138 | 3.72 |

TABLE 3

Parameter values for the iron model in a steady state.

| Parameter | Meaning | Value |
|---|---|---|
| $k_{12}$ | transfer rate from plasma to precursor cells | 8.5 |
| $k_{15}$ | transfer rate from plasma to storage | 1.62 |
| $k_{23}$ | transfer rate from precursor cells to erythrocytes | 0.1199 |
| $k_{24}$ | transfer rate from precursor cells to macrophages | 0.0101 |
| $k_{34}$ | transfer rate from erythrocytes to macrophages | 0.0012 |
| $k_{41}$ | transfer rate from macrophages to plasma | 0.29965 |
| $k_{45}$ | transfer rate from macrophages to plasma | 0.0256 |
| $k_{51}$ | transfer rate from storage to plasma | 0.007 |

Values for the parameters of the iron submodel are assigned as described below. First, parameters are formed that are able to reflect the situation in a steady state. For this purpose, the population model and the iron model are decoded and the compartment model describing iron homeostasis is the only model investigated. Further, because of steady state, all transfer rates are assumed to be constant. Then, values are assigned to the transfer rates, such that the flow of iron from one compartment to another, and also the total amount of iron in each compartment, are assumed to be within physiological ranges. For a description of the amount of normal daily iron transfer see FIG. 4. Moreover, for instance in Williams Hematology, a table can be found where the iron content for a 70 kg man is presented. See Table 2 for a list of the values.

Parameter values chosen based on this information are shown in Table 3. Note that in the steady state, losses of iron and absorption of iron are equal and, therefore, are not considered here. Thus, for the moment, iron homeostasis is considered as a closed system. Using these parameter values, a simulation was started close to the steady state values for each compartment, as shown in FIG. 10. In addition, a situation was considered where more iron is incorporated in hemoglobin and, as a consequence, storage iron is decreased, as shown in FIG. 11. Since, in this case the model is run with constant transfer rates and no feedback or regulation is taken into account, it takes quite a long time until the system finally reaches its steady state.

Further Development of the Erythropoiesis and Iron Hemeostasis Models

The models presented in Sections 2 and 3 above are very close to physiology and incorporate a lot of physiological mechanisms involved in erythropoiesis and iron homeostasis. As a consequence, the models are very extensive and lead to a class of extremely complicated mathematical equations. To solve the models, special numerical schemes have been developed to find numerical approximations for the population equations. See D. H. Fuertinger. *A model for erythropoiesis*. PhD thesis, University of Graz, Austria, 2012 (hereinafter "Fuertinger Thesis"). Although the approach chosen is very efficient, it is extremely computationally intensive, because systems of several thousands ordinary differential equations (ODE) have to be solved at every time step. Therefore, at the present time, simulations are only realizable on high performance computers, and thus not really practicable or viable in every day clinical practice and patient care, where such computers are not typically available. Since the iron component is such an important part of treatment of the anemia of renal failure, a simplified version of the models presented in Sections 2 and 3 is described hereinafter. The model presented hereinafter is still comprehensive and demanding with regard to computational costs, although the complexity of the numerical approximations reduces significantly. Instead of solving systems of several thousand ODEs, less than about a hundred ODEs have to be solved at every time step, which reduces the computational effort tremendously.

The first step is to restrict the population model presented in Section 2 to population equations with only one structural attribute, namely cell age (also called maturity of the cell). Avoidance of the structural attributes hemoglobin and transferrin receptors makes it necessary to take a step backward and reconsider how an iron model can be linked to a model describing the erythroid cell populations. Several of the assumptions made in Sections 2 and 3 have to be revisited. It is still important to keep track of how much iron is taken up by precursor cells and how much hemoglobin is contained in every cell. The lack of the structural feature hemoglobin, which allowed one to compute this quantity relatively easily, requires that other mechanisms have to be developed to replace it. The equations and assumptions are chosen such that the simplified model is as close to the one previously shown as possible. Nevertheless, these 'workarounds' only enable the description of the phenomenon of the accumulation of hemoglobin in cells and not so much the physiological mechanisms involved. Whereas this might not make a difference in most cases, the more extensive model might be needed to explain the development of RBC comprehensively for some patients with severe changes in these mechanisms.

To ensure that the description below can be read independently, a few important aspects of erythropoiesis and iron homeostasis are repeated hereinafter.

6. Erythropoiesis Model.

The aim is to develop a mathematical model which incorporates the basic mechanisms governing erythropoiesis including the control actions of erythropoietin and the potentially restricting effect of iron. Thus, the model has to include the regulatory processes for iron homeostasis, in particular describing those which are connected to erythropoiesis. The result is a comprehensive mathematical model which is able to predict red blood cell mass under EPO- and iron-therapy.

As a first step, in this chapter a model is developed which focuses solely on the effects of erythropoietin on erythroid cells. Hence, throughout this section, erythropoiesis is assumed to be sufficiently supplied with iron. Hereinafter, this model will be referred to as the Erythropoiesis Model, described in PCT Application No. PCT/US/2012/054264 published as WO 2013/036836 A2 on Mar. 14, 2013, whose contents and teachings are incorporated herein by reference in their entirety. The mathematical model developed in this section is applicable for a number of different situations, as long as it is reasonable to assume that erythropoiesis is not impaired because of a lack of iron availability. For instance, the Erythropoiesis Model is able to describe the recovery of red cell mass after blood donation, the reaction of the body to presurgical administration of ESAs, and changes in the number of erythrocytes of high altitude dwellers descending to sea level. See Fuertinger Thesis; D. H. Fuertinger, F. Kappel, S. Thijssen, N. W. Levin, and P. Kotanko. *Journal of Mathematical Biology*, 66(6):1209-1240, 2013. However, the Erythropoiesis Model is only applicable for a subpopulation of dialysis patients. 80-90% of dialysis patients treated with ESA suffer from functional iron deficiency at some stage in their therapy. See R. M. Schaefer and L. Schaefer. *Nephrology Dialysis Transplantation*, 13:9-12, 1998. It has to be considered carefully whether, even when treated with iron compounds, it is reasonable to assume that iron supply is sufficient in patients suffering from chronic kidney disease (CKD patients on dialysis treatment or not). Moreover, the Erythropoiesis Model helps to understand what the most important dynamics considering red blood cell production are. In Section 7 an Iron Model (compartment model) is developed and in Section 7.2 it is explained how this model is linked to the Erythropoiesis Model and extends it to a even more extensive and detailed model for erythropoiesis, thus providing a solid basis for a more general description of the altered processes during the very complex pathological situation of anemia of renal failure.

The Erythropoiesis Model is based on structured population models describing the different erythroid cell stages. Five different population classes of cells are considered: BFU-Es, CFU-Es, erythroblasts, marrow reticulocytes and mature erythrocytes circulating in the bloodstream (including peripheral reticulocytes). In the Erythropoiesis Model individual cells are distinguished according to their maturity, which can also be referred to as cell age. The commitment to the erythroid lineage is an irreversible event. A differentiated cell cannot regress or switch into another differentiation pathway. Thus, once a multipotent stem cell is committed to the erythroid lineage, it undergoes the complete series of differentiations until it becomes a mature red blood cell, or it dies eventually during this process. While maturing, the cell divides a number of times. Hence, age-structured population models of the form $$\frac{\partial}{\partial t}u(t,\mu) + v(E(t))\frac{\partial}{\partial \mu}u(t,\mu) = (\beta(E(t),\mu) - \alpha(E(t),\mu))u(t,\mu) \quad (10)$$

are used in order to describe the development of the cell populations. Here $u(t,\mu)$ denotes the population density of the cell population at time t with maturity $\mu$. Further, the functions $\beta$ and $\alpha$ describe the division rate and the rate of apoptosis of the cells, respectively. The functions $\alpha$ and $\beta$ a priori depend on the maturity $\mu$ and the concentration of EPO $E(t)$, respectively, at time t. The function v describes the maturation velocity and depends on the concentration $E(t)$.

For the different population classes, the characteristic properties (proliferation rate, rate of apoptosis and maturation velocity) differ. While the cell matures, it changes its morphological characteristics, such as the number of EPO- and transferrin-receptors expressed on the surface.

Figure 6A:
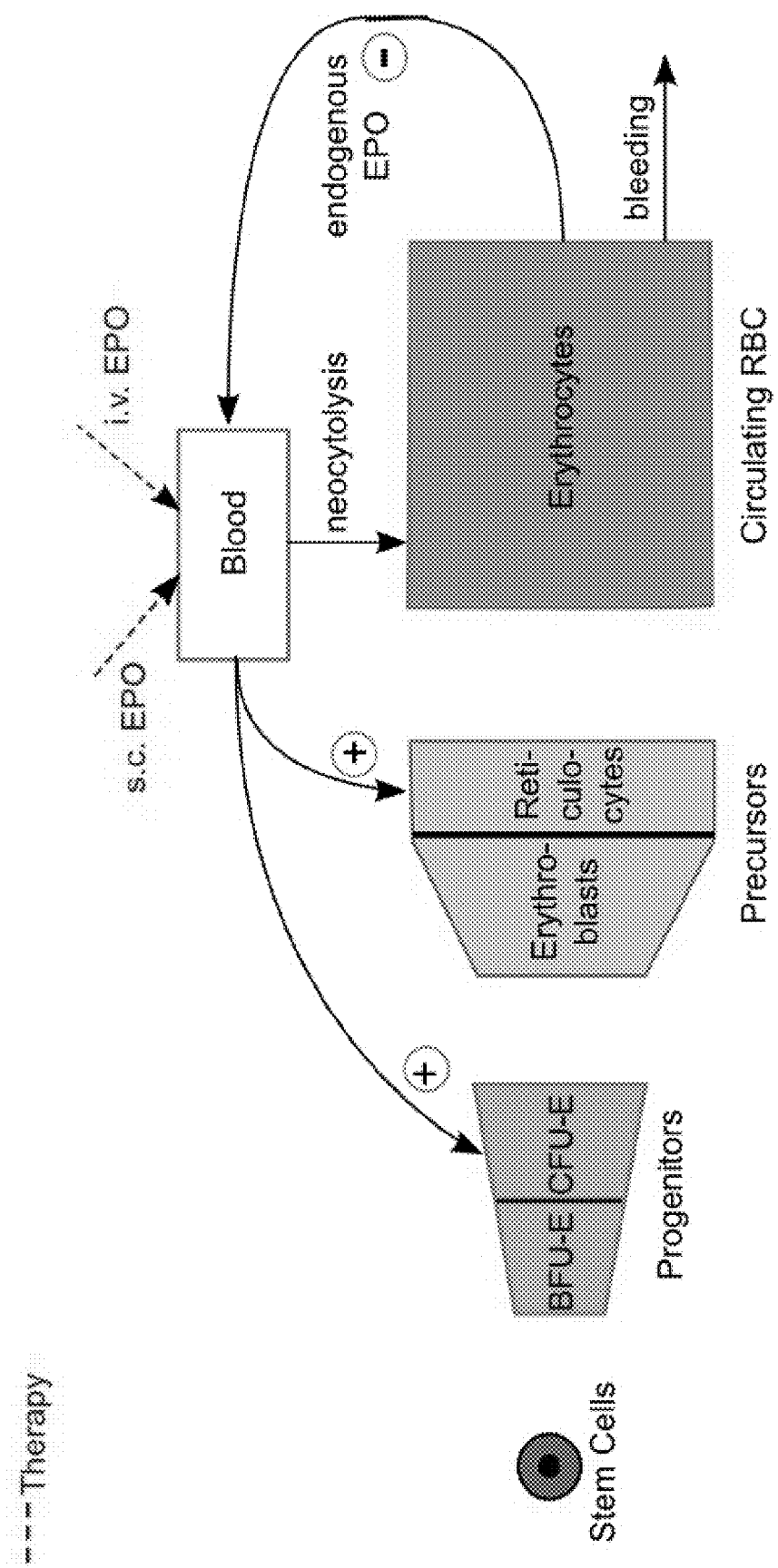
FIG. 6A is a schematic illustration of the organizational diagram of the model. The feedback for the iron submodel is not illustrated here, for reasons of clarity.
Figure 6B:
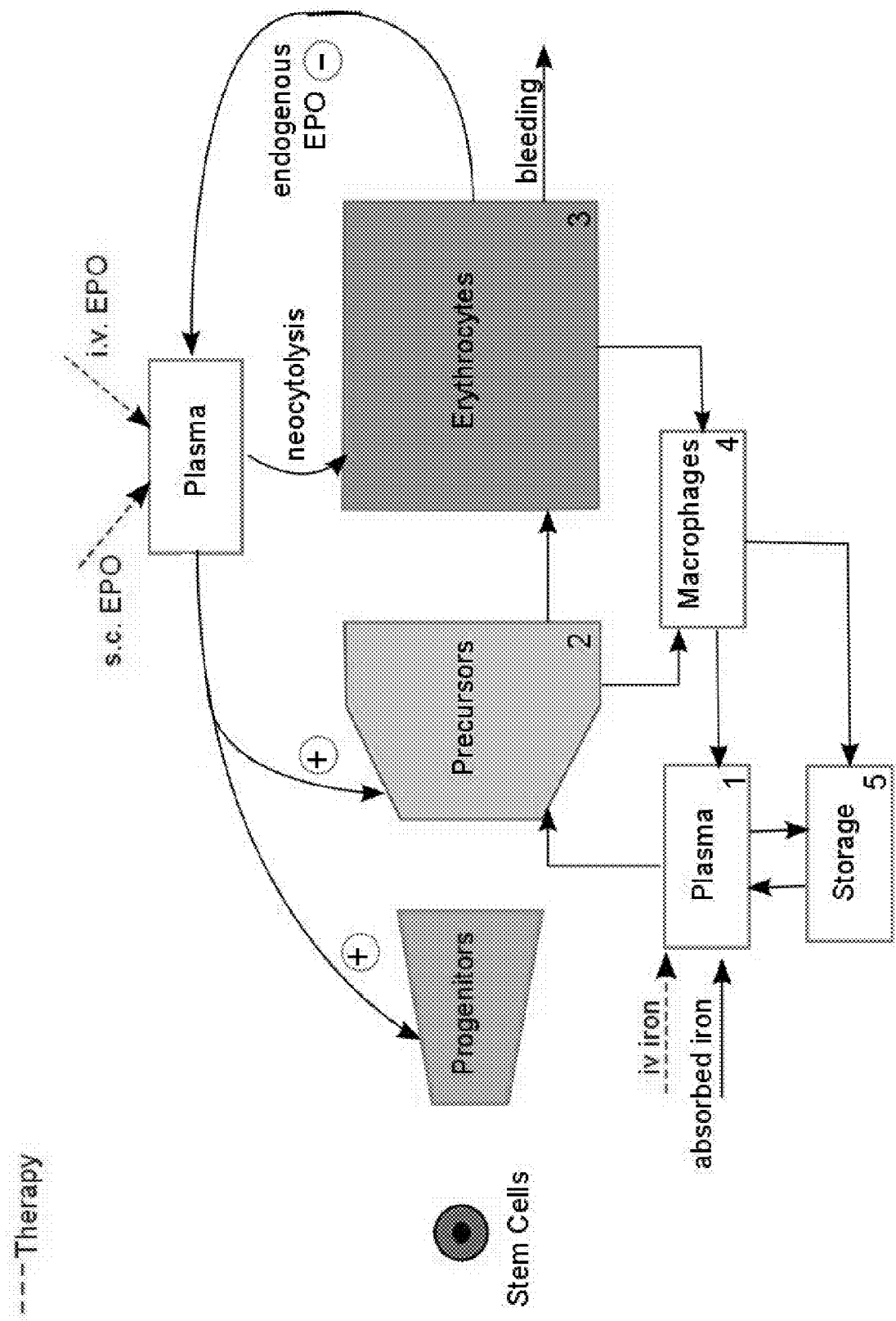
FIG. 6B is a schematic illustration of the organizational diagram of the model including the feedback for the iron submodel.

In the following sections, the assumptions that were made for the different population classes are listed, briefly described, and the mathematical equations that arise in consequence are stated. FIG. 6A gives an overview of the design and organization of the model.

6.1. Progenitor Cells: BFU-E and CFU-E Cells

Assumptions:

1. The number of cells, which commit to the erythroid lineage, is constant.

2. Cells normally stay in this stage for 8 days (3 days BFU-E and 5 days CFU-E).

3. EPO has no effect on the number of divisions or the rate of apoptosis of BFU-E.

4. The proliferation rate of CFU-E cells is constant.

5. The rate of apoptosis of CFU-E depends highly on EPO levels.

6. The maturation velocities of BFU-E and CFU-E cells are constant.

The process by which stem cells are recruited into proliferating progenitor population remains unclear. There are several hypotheses including an environmental dependency, that it is a random event, etc. For the moment, the number of stem cells entering the erythroid lineage is assumed to be independent of EPO and thus constant. The change in population of the progenitor cells over time are described considering two different classes of cells: namely BFU-E and CFU-E cells.

The earliest identifiable erythroid progenitor cell is the Burst-forming Unit Erythroid (BFU-E). At first these cells express only a very small number of EPO receptors on the surface. See Wintrobe's Clinical Hematology. Thus, it is reasonable to assume EPO has no effect on proliferation or apoptosis of these cells. See Wu et al. In culture it lasts around 6-7 days until human BFU-E have all the functional characteristics of the next cell stage—Colony-forming Unit Erythroid cells (CFU-E cells) (Assumption 2). See Williams Hematology. Morphologically, it is difficult to distinguish between those two types of cells, because there are cells in between these two developmental stages which show characteristic properties between BFU-E and CFU-E cells. Therefore, a distinction is valid but artificial.

The BFU-E cell class is described by the following population equation $$\begin{cases} \frac{\partial}{\partial t} p(t, \mu^p) + \frac{\partial}{\partial \mu^p} p(t, \mu^p) &= \beta^p p(t, \mu^p), \\ p(t, 0) &= S_0, \\ p(0, \mu^p) &= p_0(\mu^p), \end{cases}$$

where $p(t, \mu^p)$ is the population density of the cell class at time t with maturity $\mu^p$, $0 \le \mu^p \le \mu_{max}^p = 7$, $t > 0$. Further, $\beta^p$ is a constant proliferation rate and $\alpha^p \equiv 0$ (Assumption 3), $S_0$ describes the number of cells committing to the erythroid lineage (Assumption 1) and $p_0(\mu^p)$ is the population density at t=0.

Once a cell reaches the maximum age for BFU-E cells, it leaves this population class and enters the CFU-E class. Consequently, there is a continual flux of cells from one population class to the next one. CFU-E are more rapidly dividing cells than BFU-E. See Wu et al. During this stage, cells are very sensitive to EPO levels, and, under normal conditions, large numbers of generated CFU-E are not surviving. See Wintrobe's Clinical Hematology. CFU-E are highly dependent on EPO to prevent them from apoptosis, i.e., the mortality for this population class depends on the EPO concentration. Altogether, the following equations for the second class are obtained:

$$\begin{cases} \frac{\partial}{\partial t} q(t, \mu^q) + \frac{\partial}{\partial \mu^q} q(t, \mu^q) &= (\beta^q - \alpha^q(E(t))) q(t, \mu^q), \\ q(t, \mu_{min}^q) &= p(t, \mu_{max}^p), \\ q(0, \mu^q) &= q_0(\mu^q), \end{cases}$$

where $q(t, \mu^q)$ is the population density of the CFU-E class at time t with maturity $\mu^q$, $t > 0$ and $7 = \mu_{min}^q \le \mu^q \le \mu_{max}^q = 13$. Further on, $\beta^q$ stands for a constant proliferation rate (Assumption 4), $\alpha^q(E(t))$ denotes the apoptosis rate depending on the EPO-concentration (Assumption 5), $q(t, \mu_{min}^q) = p(t, \mu_{max}^p)$ describes the number of cells leaving the BFU-E cell stage and entering the CFU-E cell stage and $q_0(\mu^q)$ is the population density at t=0.

A sigmoid function is used to describe the rate of apoptosis, $$\alpha^q(E(t)) = \frac{a_1 - b_1}{1 + e^{k_1 E(t) - c_1}} + b_1,$$

where E(t) is the EPO concentration at time t and $a_1$, $b_1$, $c_1$ and $k_1$ are positive constants with $a_1 > b_1$. The function $\alpha^q$ monotonically decreases with increasing EPO concentration. Thus, a higher level of EPO causes more cells to survive.

Note that, because of Assumption 6, the cell age of progenitor cells coincides with the actual age of the cell, i.e., one defines $v^p = v^q \equiv 1$, $\forall t \ge 0$.

6.2. Precursor Cells: Erythroblasts and Marrow Reticulocytes

Assumptions:

7. Cells stay in this stage for 6-8 days (5 days erythroblasts and 1-3 days marrow reticulocytes).

8. The class erythroblasts consists of all cell stages from proerythroblast to orthochromatophilic erythroblast.

9. EPO has no effect on the number of divisions or the rate of apoptosis of erythroblasts. The proliferation rate of erythroblasts is assumed to be constant.

10. The maturation velocity of erythroblasts is constant.

11. Reticulocytes mature but do not proliferate.

12. The maturation velocity of reticulocytes depends on EPO.

13. A constant portion of marrow reticulocytes is phagocytosed.

After a CFU-E differentiates to a proerythroblast, it takes about another 6-8 days until the cell is released from the bone marrow into the bloodstream. See Jandl. The various stages of maturation from proerythroblast to orthochromatophilic erythroblast (see FIG. 1) are referred to as erythroblasts. The cells undergo several mitotic divisions until, at the stage of orthochromatophilic erythroblast, they lose their ability to divide and enter a maturation period. The erythroblastic pyramids appear normal, with no evidence of additional mitotic divisions, when production increases, i.e., the proliferation of erythroblasts is assumed to be independent of EPO levels and defined to be constant. See Williams Hematology.

Hence, the erythroblast class can be described by the following equation $$\begin{cases} \frac{\partial}{\partial t} r(t, \mu^r) + \frac{\partial}{\partial \mu^r} r(t, \mu^r) &= \beta^r r(t, \mu^r), \\ r(t, \mu_{min}^r) &= q(t, \mu_{max}^q), \\ r(0, \mu^r) &= r_0(\mu^r), \end{cases}$$

where $r(t, \mu^r)$ is the population density of the erythroblasts at time t with maturity $\mu^r$, $t > 0$ and $13 = \mu_{min}^r \le \mu^r \le \mu_{max}^r = 18$. Further, $\beta^r$ is a constant proliferation rate and $\alpha^s \equiv 0$ (Assumption 9), the maturation velocity $v^r \equiv 1$ (Assumption 10), $r(t,\mu_{min}^r)=q(t,\mu_{max}^q)$ describes the number of cells leaving the CFU-E stage and entering the erythroblasts cell stage, and $r_0(\mu^r)$ is the population density at t=0.

The differentiating process from orthochromatophilic erythroblasts to marrow reticulocytes involves the extrusion of the cell nucleus. Reticulocytes are not capable of cell divisions (Assumption 11), i.e., $\beta^s \equiv 0$. In the Erythropoiesis Model, one does not account for an impaired erythropoiesis due to iron deficiency. Still, even when the erythroid cells in the bone marrow are sufficiently supplied with iron, not all precursor cells survive. Some of the reticulocytes die before they are released to the blood stream. See G. Barosi, M. Cazzola, C. Berzuini, S. Quaglini, and M. Stefanelli. *British Journal of Haematology*, 61:357-370, 1985; M. Stefanelli, D. P. Bentley, I. Cavill, and H. P. Roeser. *The American Journal of Physiology*, 247:842-849, 1984. This is why Assumption 13 is made.

A raised EPO concentration shortens the marrow transit time of precursor cells. If the EPO level is elevated, marrow reticulocytes are released prematurely. This aspect is accounted for by allowing the maturation velocity of reticulocytes to vary depending on erythropoietin concentration. Thus, although the maximum cell age of marrow reticulocytes is fixed, the actual transit time for the cells varies between 1-3 days. Hence, altogether the transit time for precursor cells is between 6-8 days (Assumption 7).

The population equation referring to marrow reticulocytes is $$\begin{cases} \frac{\partial}{\partial t}s(t,\mu^s) + v^s(E(t))\frac{\partial}{\partial \mu^s}s(t,\mu^s) &= -\alpha^s s(t,\mu^s), \\ v^s(E(t))s(t,\mu_{min}^s) &= r(t,\mu_{max}^r), \\ s(0,\mu^s) &= r_0(\mu^s), \end{cases}$$

where $s(t,\mu^s)$ is the reticulocytes population density at time t with maturity $\mu^s$, t>0 and $18 = \mu_{min}^s \leq \mu^s \leq \mu_{max}^s = 20$. Further on, $v^s(E(t))$ is the maturation velocity depending on EPO (Assumption 12), $\alpha^s$ denotes the rate with which reticulocytes are phagocytosed (Assumption 13), $v^s(E(t))s(t,\mu_{min}^s)=r(t,\mu_{max}^r)$ describes the number of cells leaving the erythroblast cell stage and entering the reticulocyte cell stage, and $r_0(\mu^s)$ is the population density at t=0.

A sigmoid function is used to describe the changes in maturation velocity, $$v^s(E(t)) = \frac{a_2 - b_2}{1 + e^{-k_2 E(t) + c_2}} + b_2,$$

where E(t) is the EPO concentration at time t and $a_2$, $b_2$, $c_2$ and $k_2$ are positive constants with $a_2 > b_2$. The maturation velocity increases with a rising concentration of EPO. Note that a slower maturation velocity causes the cells to reach the maximum cell age $\mu_{max}^s$ at a later point, whereas a faster maturation velocity shortens the transit time, i.e., the cells reach $\mu_{max}^s$ earlier.

6.3. Erythrocytes.

Assumptions:

14. Erythrocytes and blood reticulocytes are subsumed in one class.
15. Cells mature but do not proliferate.
16. There is a fixed random daily break-down of red blood cells (not to be confused with loss of erythrocytes due to senescence).
17. A drop in EPO concentration beneath a threshold precipitates neocytolysis.
18. Erythrocytes with age between 14-21 days are likely to be affected by neocytolysis.
19. Cells are phagocytosed when they reach the maximum age.
20. The maximum age of erythrocytes in a healthy persons is 120 days.

The reticulocytes are released from the bone marrow into the blood stream and within 1-2 days they mature to erythrocytes. Circulating red blood cells have no nuclei and therefore they are not able to proliferate and they are not able to repair themselves. Thus, the life span of these cells is limited. In healthy adults the average life span is about 120 days, but it can significantly shorten in some pathologies. See e.g., Jandl. If not otherwise stated, 120 days is used as the maximal age of erythrocytes for the Erythropoiesis Model.

Cells can be lost for different reasons:

due to internal or external bleeding, because of random daily-breakdown, because neocytolysis is triggered, and, because of eryptosis of senescent cells.

Altogether, the following equation is obtained for red blood cells:

$$\begin{cases} \frac{\partial}{\partial t}m(t,\mu^m) + \frac{\partial}{\partial \mu^m}m(t,\mu^m) &= -\alpha^m(E(t),\mu^m)m(t,\mu^m), \\ m(t,0) &= v^s(E(t))s(t,\mu_{max}^s), \\ m(0,\mu^m) &= m_0(\mu^m), \end{cases}$$

where $m(t,\mu^m)$ is the population density for the erythrocyte class at time t with maturity $\mu^m$, t>0 and $0 = \mu_{min}^m \leq \mu^m \leq \mu_{max}^m = 120$ (Assumption 20). Moreover, $m(t,0) = v^s(E(t))s(t,\mu_{max}^s)$ describes the number of reticulocytes entering the blood stream and $m_0(\mu^m)$ is the population density at t=0. In the population equation $\alpha^m(E(t),\mu^m)$ denotes a random daily break-down and neocytolysis $$\alpha^m(E(t),\mu^m) = \begin{cases} \gamma^m(\mu^m) + \min(c_E/E(t)^{k_E}, b_E) & \text{for } E(t) < \tau_E, \mu_{min}^{m,n} \leq \mu^m \leq \mu_{max}^{m,n}, \\ \gamma^m(\mu^m) & \text{otherwise}, \end{cases}$$

where $b_E$, $c_E$, $k_E$ are positive constants, $\tau_E$ is the threshold beneath which neocytolysis is triggered (Assumption 17), and $[\mu_{min}^{m,n},\mu_{max}^{m,n}]=[14,21]$ (Assumption 18) is the age-interval during which cells are affected by neocytolysis, and $t \geq 0$. Additionally, it is possible to add a further term $\alpha_{bleed}^m(t)$ to the mortality rate in case of bleeding. Since it is assumed that a cell is phagocytosed when it reaches its maximum age (Assumption 19), the mortality rate $\gamma^m(\mu^m)$ needs to be chosen such that $\gamma^m(\mu^m) = \alpha_{rand}^m$ for $\mu_{min}^m \leq \mu^m \leq \mu_{max}^m - \delta$ with $\delta > 0$ sufficiently small and $\int_{\mu_{max}^m - \delta}^{\mu_{max}^m} \gamma^m(\mu^m) = \infty$. Here $\alpha_{rand}^r$ is a random daily break-down (Assumption 16). A possible choice for $\gamma^m(\mu^m)$ is $$\gamma^m(\mu^m) = \begin{cases} \alpha_{rand}^m & \text{for } \mu^m \in [\mu_{min}^m, \mu_{max}^m - \delta], \\ \dfrac{3\alpha_{rand}^m \delta^2}{(\mu^m)^2 - 2(\mu_{max}^m + \delta)\mu^m + (\mu_{max}^m + 2\delta)\mu_{max}^m} & \text{for } \mu^m \in [\mu_{max}^m - \delta, \mu_{max}^m), \\ \infty & \text{for } \mu^m \geq \mu_{max}^m. \end{cases}$$

6.4. Erythropoietin

Assumptions:

21. Release of EPO is controlled by a negative feedback mechanism according to the oxygen content.

22. Oxygen carrying capacity is directly proportional to the number of erythrocytes.

23. The degradation rate of EPO is constant.

24. There is a slight delay in reaction of the EPO production rate to the number of RBC but this is negligible compared to the duration of development of erythrocytes.

The kidneys adjust the release of EPO according to the oxygen carrying capacity of the blood. If blood oxygen content is lower than normal, then EPO production increases and vice versa. Thus, the production of EPO is controlled by a negative feedback mechanism and allows for more red blood cells to be developed in case of an undersupply of the body with oxygen by opposing programmed cell death of erythroid progenitor cells. Further, if EPO decreases beneath a certain threshold, neocytolysis is triggered, that is, a process wherein macrophages start to phagocytose young erythrocytes (neocytes).

A sigmoid function which depends on blood oxygen partial pressure is used to model the feedback involving the release of erythropoietin $E_{in}^{end}(t)$ from the kidneys into plasma. As a consequence of Assumption 22, the amount of $E_{in}^{end}(t)$ of EPO released by the kidney per unit time can be directly computed by use of the total population of erythrocytes $M(t) = \int_0^{\mu_{max}^m} m(t,\mu^m) d\mu^m$. Recall that this class consists of all circulating red blood cells (Assumption 14).

$$E_{in}^{end}(t) = \frac{a_3 - b_3}{1 + e^{k_3 \tilde{M}(t) - c_3}} + b_3,$$

where $\tilde{M}(t) = 10^{-8} M(t)/TBV$ is a scaled erythrocytes "concentration". Here, TBV is the total blood volume. The constants $a_3$, $b_3$, $c_3$, $k_3$ are positive and satisfy $a_3 > b_3$. The function $E_{in}^{end}(t)$ is monotonically decreasing. Thus, the release of EPO increases if the number of circulating red blood cells decreases (Assumption 21). The dynamics of the endogenous EPO concentration $E^{end}(t)$ in plasma are described by the following ordinary differential equation:

$$\frac{d}{dt}E^{end}(t) = \frac{1}{TBV}E_{in}^{end}(t) - c_{deg}^{end}E^{end}(t), \quad (11)$$

where $E^{end}(t)$ is the endogenous EPO concentration in plasma, $E_{in}^{end}$ is the amount of EPO released by the kidneys and $c_{deg}^{end}$ describes the constant degradation rate of endogenous EPO (Assumption 23).

The degradation rate $c_{deg}^{ex}$ for exogenous EPO differs from the one for endogenous EPO and varies according to the kind of ESA administered. Therefore, an additional ODE is needed to describe the change in the plasma concentration of an ESA $$\frac{d}{dt}E^{ex}(t) = \frac{1}{TBV}E_{in}^{ex}(t) - c_{deg}^{ex}E^{ex}(t). \quad (12)$$

Here $E_{in}^{ex}(t)$ is the rate at which the artificial hormone is administered and $c_{deg}^{ex}$ is the rate with which the exogenous hormone is degraded. In intravenous administration, the total amount of the agent is injected into a vein, within a very short time interval. In this case $E_{in}^{ex}(t)$ can be approximated by $E_0^{ex}(t)\delta_{t_0}(t)$, where $E_0^{ex}$ is the amount of artificial hormone administered and $\delta_{t_0}(t)$ is the Dirac delta impulse located at $t_0$, the time when the administration takes place. The overall concentration of EPO in blood consists of the naturally produced erythropoietin in the body and the administered ESA $$E(t) = E^{ex}(t) + E^{end}(t).$$

6.5. Mathematical Model—Erythropoiesis Model

For the convenience of the reader, all equations of the Erythropoiesis Model are collected in this section:

$$\frac{\partial}{\partial t}p(t,\mu^p) + \frac{\partial}{\partial \mu^p}p(t,\mu^p) = \beta^p p(t,\mu^p),$$

$$\frac{\partial}{\partial t}q(t,\mu^q) + \frac{\partial}{\partial \mu^q}q(t,\mu^q) = (\beta^q - \alpha^q(E(t)))q(t,\mu^q),$$

$$\frac{\partial}{\partial t}r(t,\mu^r) + \frac{\partial}{\partial \mu^r}r(t,\mu^r) = \beta^r r(t,\mu^r),$$

$$\frac{\partial}{\partial t}s(t,\mu^s) + v^s(E(t))\frac{\partial}{\partial \mu^s}s(t,\mu^s) = -\alpha^s s(t,\mu^s),$$

$$\frac{\partial}{\partial t}m(t,\mu^m) + \frac{\partial}{\partial \mu^m}m(t,\mu^m) = -\alpha^m(E(t),\mu^m)m(t,\mu^m),$$

$$\frac{d}{dt}E^{end}(t) = \frac{1}{TBV}E_{in}^{end}(t) - c_{deg}^{end}E^{end}(t),$$

$$\frac{d}{dt}E^{ex}(t) = \frac{1}{TBV}E_{in}^{ex}(t) - c_{deg}^{ex}E^{ex}(t),$$

where $$\alpha^q(E(t)) = \frac{a_1 - b_1}{1 + e^{k_1 E(t) - c_1}} + b_1,$$

$$v^s(E(t)) = \frac{a_2 - b_2}{1 + e^{-k_2 E(t) - c_2}} + b_2.$$

and $$\alpha^m(E(t),\mu^m) = \begin{cases} \gamma^m(\mu^m) + \min\left(\dfrac{c_E}{E(t)^{k_E}}, b_E\right), & \text{for } E(t) < \tau_E, \mu_{min}^{m,n} \leq \mu^m \leq \mu_{max}^{m,n}, \\ \gamma^m(\mu^m), & \text{otherwise,} \end{cases}$$

with $$\gamma^m(\mu^m) = \begin{cases} \alpha_{rand}^m & \text{for } \mu^m \in [\mu_{min}^m, \mu_{max}^m - \delta], \\ \dfrac{3\alpha_{rand}^m \delta^2}{(\mu^m)^2 - 2(\mu_{max}^m + \delta)\mu^m + (\mu_{max}^m + 2\delta)\mu_{max}^m} & \text{for } \mu^m \in [\mu_{max}^m - \delta, \mu_{max}^m), \\ \infty & \text{for } \mu^m \geq \mu_{max}^m. \end{cases}$$

Further, the boundary conditions are given by
$p(t,0) = S_0$,
$q(t,\mu_{min}^q) = p(t,\mu_{max}^p)$,
$r(t,\mu_{min}^r) = q(t,\mu_{max}^q)$,
$v^s(E(t))s(t,\mu_{min}^s) = r(t,\mu_{max}^r)$, $m(t,0)=v^s(E(t))s(t,\mu_{max}^s)$,
$m(0,\mu^m)=m_0(\mu^m)$,
and the initial values are
$p(0,\mu^p)=p_0(\mu^p)$,
$q(0,\mu^q)=q_0(\mu^q)$,
$r(0,\mu^r)=r_0(\mu^r)$,
$s(0,\mu^s)=r_0(\mu^s)$,
$E^{end}(0)=E_0^{end}$,
$E^{ex}(0)=E_0^{ex}$.

The feedback is described by $$E_{in}^{end}(t) = \frac{a_3 - b_3}{1 + e^{k_3 \tilde{M}(t) - c_3}} + b_3,$$

where $\tilde{M}(t)=10^{-8}M(t)/TBV$, with $M(t)=\int_0^{\mu_{max}^m} m(t,\mu^m)d\mu^m$ and one has $$E(t)=E^{ex}(t)+E^{end}(t).$$

7. Iron Homeostasis.

As described above, much of the iron in the human body can be found in circulating erythrocytes incorporated in hemoglobin. However, most of the iron used for the production of new erythrocytes comes from hemoglobin recycling and not from absorption. When a senescent red cell is phagocytosed, the macrophage internalizes hemoglobin, degrades it and exports it back out into blood circulation.

Iron is stored in form of ferritin or hemosiderin, where the latter is more a kind of a long-term storage, because iron within deposits of hemosiderin is very poorly available. Storage sites can be found mainly in the liver, the spleen and the bone marrow but, for instance, small amounts of hemosiderin can be found in almost any tissue. There are differences between men and women in the amount of iron that is stored (Females about 200-400 mg, Males about 1000 mg). See Crepaldi.

Iron is carried around in plasma by a transport protein, which is called transferrin. Transferrin is produced by the liver. Cells that are in need for iron express transferrin receptors, and after transferrin has formed a complex with this receptor, iron is transported into the cell. Transferrin exists in three different forms: iron-free (apotransferrin), one iron (monoferric transferrin) and two iron (differic transferrin) atoms bound. The concentration of iron and the amount of transferrin present in plasma determine the relative abundance of each form. Although iron bound to transferrin amounts to only about 3 mg of total body iron, it is the most important iron pool with the highest rate of turnover, about 30 mg/day. Approximately 80% of this iron is transported to the bone marrow and used by erythroid cells. See Lieu et al. The amount of transferrin-bound iron is determined by three processes: macrophage iron recycling, (hepatic) iron storage and duodenal iron absorption. See Wrighting.

In the last 15 years, understanding of the regulation of systemic iron homeostasis has changed substantially. The antimicrobial peptide hepcidin, which is secreted by the liver, was identified to be the systemic iron regulator. Hepcidin inhibits iron transport by binding to the iron exporter ferroportin. Hence, it keeps gut enterocytes from secreting iron into circulation, thereby functionally reducing iron absorption. Further, it prevents iron release from macrophages and blocks the stores as well, by shutting off the means of transport out of cells. See FIG. 4 for a diagram of the iron cycle and daily turnover rates and FIG. 5 for a sketch of systemic iron regulation.

There exist some sensing mechanisms in the liver that gauge the amount of iron needed to support erythropoiesis. Note that hepatocytes in the liver, which secrete hepcidin, also release transferrin into circulation and are one of the major iron storage sites. If the concentration of iron stores are too low and/or erythropoiesis is increased, then the level of the hormone hepcidin is decreased. Thus, for instance, low hepcidin concentrations are observed in patients with absolute iron-deficiency anemia, or anemias with high erythropoietic activity. See Goodnough 2010. The consequence of a lower hepcidin level is that more iron is taken up via the duodenum and more iron is released from macrophages and from the stores. See Crichton; Fleming. If iron stores are full and/or erythropoiesis is decreased, then more hepcidin is secreted by hepatocytes. Dietary iron absorption, macrophage iron recycling and release of iron from stores is partly or fully blocked as a result of the binding to the iron exporter ferroportin.

Hepcidin is an acute phase-reactant, and, during inflammation, cytokines stimulate overproduction of hepcidin. Hence, the feedback is altered during inflammation, which is a prominent problem in chronic kidney disease. As a consequence, the body is not able to sufficiently supply developing red blood cells with iron and erythropoiesis is impaired, although there might be more than enough iron in stores and macrophages, but it is simply not available. This paradoxical situation is called functional iron deficiency, a condition where stored iron is sufficient, but circulating iron is deficient, whereas a situation where the iron content of the body is too low (depleted stores) is referred to as absolute iron deficiency that occurs when iron stores are depleted.

7.1 Iron Model

Assumptions

25. Five iron pools are considered within the body: a plasma pool, iron in precursor cells, iron in erythrocytes, iron in the macrophages and a storage pool.

26. Other iron in the body is ignored.

27. Hepcidin regulates iron homeostasis.

28. Stressed erythropoiesis and depleted stores decrease the amount of hepcidin released into plasma.

29. Large iron stores and inflammation increase hepcidin levels.

30. The amount of iron in plasma is proportional to the amount of transferrin molecules carrying iron. (Free iron is neglected.)

31. There is no differentiation between monoferric and differic transferrin.

32. Iron is only lost via loss of cells, i.e. iron lost via urine and sweat is neglected.

Iron is a part of hemoglobin which provides the means of $O_2$ transport to the tissue. The rate at which iron can be released to plasma from existing stores and macrophages may easily limit the rate of iron delivery for hemoglobin synthesis. Therefore, a strong relationship between impaired erythropoiesis and total body iron burden exists. See Crichton for an excellent description of iron homeostasis and its effects.

Iron is a substance which is very tightly controlled from the body as iron overload is toxic. Iron homeostasis can be only achieved by the control of absorption because the human body, unlike other mammals, is not able to influence the excretion of iron. Under normal circumstances the average daily loss of iron is very small (men 1 mg, women 2 mg, because of menstruation).

For the Iron Model, five dynamic iron pools are considered within the body: a plasma pool, iron in precursor cells, iron in erythrocytes, iron in the macrophages and a storage pool. Hence, ferritin and hemosiderin stores are lumped together. Other iron in the body is ignored. For a sketch of the organizational structure of the Iron Model see FIG. 8. The amount of iron lost via urine and sweat is neglected. Thus, in this model, excretion of iron only takes place when cells are lost. On one hand, this can be due to loss of RBCs, i.e., due to external bleeding, and, on the other hand, there is a daily loss of epithelial cells. Further, one assumes that only the precursor cells in the bone marrow uptake iron, and ineffective erythropoiesis depends on the amount of iron which can be provided for erythropoiesis. Moreover, the model accounts for the loss of iron from erythrocytes during senescence.

The general form of the compartmental Iron Model is as follows:

$$\frac{d}{dt}a_1 = k_{41}(H)a_4 + k_{iv,1}a_{iv} + k_{gastro,1}(H)a_{gastro} + k_{51}(H)a_5 - k_{15}a_1 - k_{12}a_1,$$

$$\frac{d}{dt}a_2 = k_{12}a_4 - f_{24} - f_{23},$$

$$\frac{d}{dt}a_3 = f_{23} - f_{34} - f_{3,out},$$

$$\frac{d}{dt}a_4 = f_{24} + f_{34}a_3 - k_{41}(H)a_4 - k_{45}a_4,$$

$$\frac{d}{dt}a_5 = k_{15}a_1 + k_{45}a_4 - k_{51}(H)a_5.$$

Note, in the above equations, the dependence of particular components on t was not explicitly stated to simplify notation. Furthermore, $a_i$, i=1, ..., 5, denotes the amount of iron in the compartment i and $k_{ij}$, i, j=1, ..., 5 are the transfer rates from compartment i to compartment j, i.e., $k_{ij}a_i$ is the rate at which iron is moving from compartment i to compartment j. Further, $f_{ij}$ denote the rates at which iron is transferred from compartment i into compartment j, when it is not of the simple form $k_{ij}a_i$; $f_{3,out}$ is the amount of iron which is lost by bleeding. Additionally, $a_{iv}$ denotes the amount of iron intravenously administered, whereas $a_{gastro}$ is the amount of iron in the duodenum. Finally, $k_{iv,1}$ and $k_{gastro,1}(H)$ are the corresponding flow rates. The rate $k_{gastro,1}$ can be described by a decreasing sigmoidal function $$k_{gastro,1}(H(t)) = \frac{a_5 - b_5}{1 + e^{-k_5 H(t) + c_5}} + b_5,$$

where $a_5$, $b_5$, $c_5$ and $k_5$ are positive constants with $a_8 > b_8$. The function H(t) is the solution of the differential equation (13) below.

Since the time needed to administer iron is very short compared to other time constants in the system, the following can be taken $$k_{iv,1}a_{iv} = a_{iv,total}\delta_{t_0}.$$

Here $a_{iv,total}$ is the total amount of iron administered and $\delta_{t_0}$ is the Dirac delta function located at $t_0$.

7.1.1 Hepcidin Feedback

The regulator of iron homeostasis is hepcidin, a peptide hormone produced by the liver. Hepcidin negatively regulates the availability of iron in plasma by direct inhibition of ferroportin. Ferroportin is the iron exporter required for iron egress from iron exporting cells, as for instance, enterocytes and macrophages. Hepcidin acts as a medium to withhold iron from certain invasive bacteria, as they are not able to proliferate under conditions of insufficient iron supply. The dynamics of the hepcidin concentration in plasma is calculated according to $$\frac{d}{dt}H(t) = \frac{1}{TBV}H_{prod}(t) - c_{deg}^H H(t), \quad (13)$$

where $H_{prod}(t)$ is the rate at which hepcidin, produced by the hepatocytes, is released into the plasma at time t. TBV is the total blood volume, and $c_{deg}^H$ is the rate at which hepcidin is degraded. The production rate $H_{prod}(t)$ of hepcidin is obtained as the result of a feedback loop involving the total precursor cell population, the amount of iron stored and the state of inflammation of the patient, $$H_{prod}(t) = f(U(t), a_5(t), i(t)).$$

Here $$U(t) = \int_{\mu_{min}^r}^{\mu_{max}^r} r(t, \mu^r) d\mu^r + \int_{\mu_{min}^s}^{\mu_{max}^s} s(t, \mu^s) d\mu^s,$$

where U(t) describes the total precursor cell population (erythroblasts+reticulocytes). Further, $a_5(t)$ is the amount of iron stored and i(t) is the inflammation status at time t. The feedback is modeled using a monotonically increasing sigmoidal function $$H_{prod}(t) = \frac{a_H - b_H}{1 + e^{-k_H C(t) + c_H}} + b_H,$$

where $a_H$, $b_H$, $c_H$ and $k_H$ are positive constants with $a_H > b_H$. The function $$C(t) = -c_U U(t) + c_{a_5} a_5(t) + c_i i(t)$$

is an auxiliary equation that increases if stores or inflammation status rises, and decreases when more RBCs are produced. Here, $c_U$, $c_{a_5}$ and $c_i$ are positive constants.

7.2. Iron Model Linked to the Erythropoiesis Mode. 1
Assumptions

33. All types of precursor cells synthesize hemoglobin.
34. The rate at which the amount of hemoglobin in precursor cells changes, depends on the number of transferrin receptors (TfR) on the cell membrane and the amount of iron in plasma.
35. Cells with the same age express the same amount of TfR on the membrane.
36. An erythroblast starts with 300,000 TfR on the cell membrane.
37. This number increases sharply and peaks after 1.5 days at 800,000 TfR.
38. After that time, it declines to 100,000 TfR on bone marrow reticulocytes.
39. The number of TfR on bone marrow reticulocytes is constant (100,000 TfR/cell).
40. The rate of apoptosis of precursor cells (erythroblasts AND reticulocytes) depend on cell age and hemoglobin.
41. Iron that enters a precursor cell is incorporated into hemoglobin, i.e., no free iron in the cell is considered.
42. Erythrocytes don't lose iron during senescence.

Some thought has to be given to how the iron model can be linked to the population model. Iron is consumed by precursor cells (erythroblasts and bone marrow reticulocytes) and used for hemoglobin synthesis. The amount of iron that is taken up by a cell depends on the number of transferrin receptors (TfR) expressed on the membrane and the concentration of iron in plasma. In order to simplify notation, the minimal cell age of precursor cells $\mu_{min}^r$ is set to zero, i.e., the cell age for erythroblasts is shifted from $8 = \mu_{min}^r \leq \mu^r \leq \mu_{max}^r = 13$ to $0 = \mu_{min}^r \leq \mu^r \leq \mu_{max}^r = 5$ and the cell age for bone marrow reticulocytes consequently is shifted from $13 = \mu_{min}^s \leq \mu^s \leq \mu_{max}^s = 15$ to $5 = \mu_{min}^s \leq \mu^s \leq \mu_{max}^s = 7$.

The contact rate between the TfRs of a cell and transferrin molecules in plasma carrying iron is governed by the law of mass action and thus is given by:

$$d_1 \tau(t) \frac{a_1(t)}{TBV}, \quad (14)$$

where $d_1$ is a rate constant that differs for different patients, as it depends on the volume of the active bone marrow. Further, $\tau(t)$ is the cumulative amount of TfR on cell membranes of precursor cells (erythroblasts and bone marrow reticulocytes) at time t and $a_1(t)$ is the concentration of iron in plasma at time t. Note that this is at the same time the rate with which iron leaves the plasma compartment and enters the precursor cells. The cumulative sum of TfR expressed on all precursor cells $\tau(t)$ is determined by $$\tau(t) = \int_{\mu_{min}^r}^{\mu_{max}^r} \varphi(\mu^r) r(t, \mu^r) d\mu^r + \int_{\mu_{min}^s}^{\mu_{max}^s} \varphi(\mu^s) s(t, \mu^s) d\mu^s, \quad (15)$$

where $\phi(\mu)$ is the function describing the number of TfR on a cell with cell age $\mu$, $r(t,\mu^r)$ is the density of erythroblasts, and $s(t,\mu^s)$ is the density of bone marrow reticulocytes.

7.2.1. Function for the Transferrin Receptors.

Assumptions 35-39 govern the development of the transferrin receptors. One ensures that Assumptions 35-38 are met by choosing a polynomial of degree 3

$$\phi(\mu) = a_4\mu^3 + b_4\mu^2 + c_4\mu + d_4,$$

and choosing the coefficients $a_4$, $b_4$, $c_4$ and $d_4$ such that the function $\phi$ satisfies the following conditions:

$$\phi(0)=30, \phi(1.5)=80, \phi'(1.5)=0, \phi(5)=10. \quad (16)$$

For computational reasons, the number of TfR is multiplied by $10^{-4}$. Then the first condition in eq. (16) coincides with Assumption 36. The second and third condition reflect Assumption 37 and, with the last condition, one ensures that there is a smooth transition in the number of TfR from erythroblastic cells to reticulocytes. Deriving and solving the linear system that arises from eq. (16) gives $a_4=3.3016$ $b_4=-32.127$ $d_4=30$. Further, using Assumption 38, the function $\phi$ can be extended to bone marrow reticulocytes. Altogether, one has $$\varphi(\mu) = \quad (17)$$

$$\begin{cases} 3.3016 \ \mu^3 - 32.127 \ \mu^2 + 74.0952 \ \mu + 30, & \text{for } \mu \in [\mu_{min}^r, \mu_{max}^r], \\ 10, & \text{for } \mu \in [\mu_{min}^s, \mu_{max}^s]. \end{cases}$$

Figure 12:
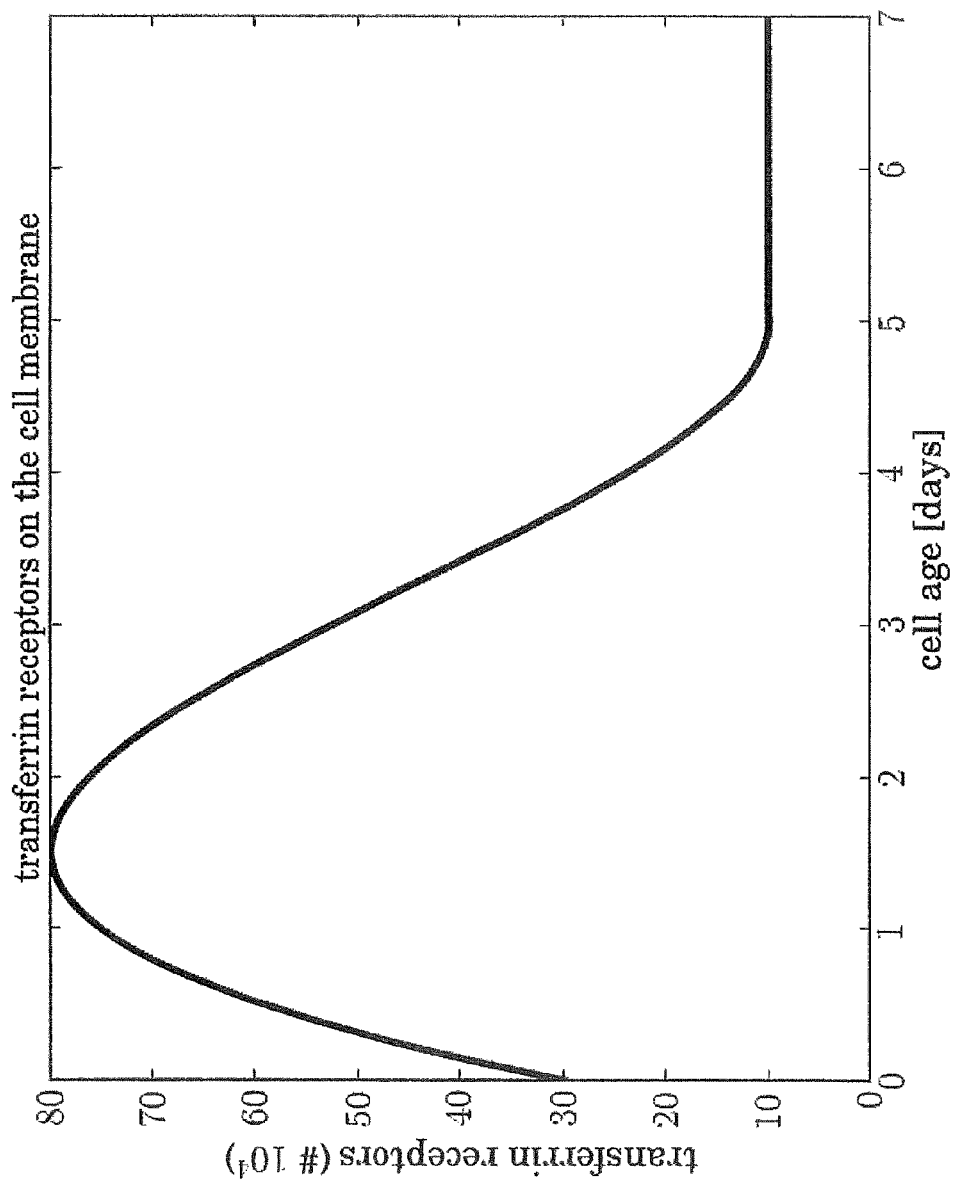
FIG. 12 is a graph of transferrin receptors (#×10$^4$) as a function of cell age (days).

For a plot of the function $\phi$ see FIG. 12.

7.2.2. Accumulation of Hemoglobin

Red blood cells carry hundreds of hemoglobin molecules which enables them to carry oxygen. Hemoglobin has four subunits each containing a heme group. An iron atom is embedded in the middle of the heme group. Hence, in one hemoglobin molecule four iron atoms are incorporated. In order to keep track of the accumulation of hemoglobin molecules in the precursor cells, the development of the TfR and the amount of iron available at certain times have to be considered. A consequence of Assumption 35 is that cells with the same cell age all carry the same amount of hemoglobin. The amount of hemoglobin a cell with age $\bar{\mu}$ accumulated can vary over time t but is invariant among cells with age $\bar{\mu}$ at a specific time $\bar{t}$. First, one focuses on the erythroblast population class, where one has the special case that the maturation velocity $v \equiv 1$, i.e. the cell age and the time for how long a cell has been an erythroblast, and thus had time to accumulate hemoglobin, coincide. Hereinafter, the actual age of the cell, i.e. the time that elapsed since the cell became a precursor cell, will be called calendric age. This is to emphasize the difference between the cell age and the actual age, i.e. the calendric age.

The rate with which hemoglobin increases in a cell is given by $$\frac{d}{dt}(h((t, \mu(t))) = \frac{\partial}{\partial t} h(t, \mu(t)) + \frac{\partial}{\partial \mu} h(t, \mu(t))v(E(t)) \quad (18)$$

$$= d \ \varphi(\mu(t)) \frac{a_1(t)}{TBV},$$

where $h(t,\mu(t))$ denotes the amount of hemoglobin in a cell with age $\mu(t)$ at time t. Note that, in most cases, the dependence of the cell age $\mu$ on time t is not explicitly stated, because there is no necessity to do so. Here, one has to consider this fact, as it is important for the derivation of the function h. Further, d is a rate constant which is different from $d_1$ because here one considers hemoglobin instead of iron, see eq. (14). The ratio between d and $d_1$ is given by the fact that each hemoglobin molecule consists of four iron atoms. The function $\phi(\mu)$ is determined by eq. (17), $a_1(t)$ describes the amount of iron in the plasma compartment and TBV denotes the total blood volume. For a detailed description of how the amount of hemoglobin in a cell with age $\bar{\mu}$ at time $\bar{t}$ can be calculated from eq. (18), see Appendix A4.

Maturation velocity $v \equiv 1$

Cells in the erythroblast population class in the Erythropoiesis Model satisfy the condition that cell age and calendric age of the cell coincide, see Section 6. This makes it easier to keep track of the accumulation of hemoglobin. In order to calculate the amount of hemoglobin a cell with cell age $\bar{\mu}$ at time $\bar{t}$ carries, one has to consider that the cell entered the population class at time $\bar{t}-\bar{\mu}+\mu_{min}$, where $\mu_{min}$ denotes the minimal cell age of the population class. Further, the amount of TfR on the cell membrane of the cell that entered the population at time $\bar{t}-\bar{\mu}+\mu_{min}$ was $\phi(\mu_{min})$ and the amount of iron in plasma at that time was $a_1(\bar{t}-\bar{\mu}+\mu_{min})$. With these considerations, the amount of hemoglobin a cell with cell age $\bar{\mu}$ at time $\bar{t}$ carries is given by the following integral $$h(\bar{t}, \bar{\mu}) = \frac{d}{TBV} \int_{\bar{t}-\bar{\mu}+\mu_{min}}^{\bar{t}} \varphi(s - \bar{t} + \bar{\mu}) a_1(s) \, ds.$$

Note that the calculation makes use of the history of the available amount of iron in plasma from $\bar{t}-\bar{\mu}+\mu_{min}$ to $\bar{t}$.

For the erythroblast population (the cell age was transformed such that $\mu_{min}^r=0$) the above equation simplifies to $$h(t, \mu^r) = \frac{d}{TBV} \int_{t-\mu^r}^{\bar{t}} \varphi(s - t + \mu^r) a_1(s) \, ds. \quad (19)$$

Maturation velocity $v = v(E(t))$

In the case that cells have a variable maturation velocity, it gets more difficult to keep track of the accumulation of hemoglobin. First, one has to calculate at which time $\hat{t}$ a cell that has cell age $\bar{\mu}$ at time $\bar{t}$ entered the population class. Therefore, the following equation has to be solved with regard to $\hat{t}$ $$\bar{\mu} = \mu_{min} + \int_{\hat{t}}^{\bar{t}} v(E(s)) \, ds,$$

i.e., one has to (numerically) find the root of the following function $$f(\bar{t}, \bar{\mu}) = \mu_{min} - \bar{\mu} + \int_{\hat{t}}^{\bar{t}} v(E(s)) \, ds. \quad (20)$$

The value $\eta = \bar{t} - \hat{t}$ reflects the calendric age of the cell. (It represents the time that passed since the cell entered the population class and does not necessarily coincide with the cell age/maturity of the cell.)

In the Erythropoiesis model presented in Section 6, only the reticulocyte population has a variable maturation velocity. Assumption 39 states that cells in this specific population class express a constant number of TfR on their membranes. For the sake of simplicity, the special case $\phi = \text{const.}$ is considered here, and the general case when $\phi = \phi(\mu)$ is not considered.

Thus, the amount of hemoglobin in a reticulocyte with calendric age $\eta^s \in [5,8]$ at time t is given $$h(t, \eta^s) = h(t - \eta^s + \mu_{min}^s, \mu_{max}^r) + \varphi \frac{d}{TBV} \int_{t - \eta^s + \mu_{min}^s}^{\bar{t}} a_1(s) \, ds. \quad (21)$$

The calendric age of the cell has been derived using the solution of eq. (20) and $h(t - \eta^s + \mu_{min}^s, \mu_{max}^r)$ is derived from eq. (19).

7.2.3 Rate of Apoptosis of Precursor Cells

The construction of the rate of apoptosis of precursor cells is inspired by the fact that cells that do not synthesize hemoglobin sufficiently are more likely to die. See Schmidt.

Hereinafter, one is going to refer to cell age of the erythroblasts and the calendric age (see eq. 20) of the reticulocytes, respectively, as $\eta$. Consequently, $\eta \in [0,8]$ and denotes the time that elapsed since a cell became a precursor cell.

First, a "reference hemoglobin accumulation curve" denoted by $h^*(\eta)$ is created using eqs. (19) and (21). The construction is based on an average male healthy adult, assuming that:
  the person's erythropoiesis and iron homeostasis is in steady state,
  the total blood volume is 5 liters,
  and the amount of iron in plasma is 3 mg, i.e., $a_1 \equiv 3$.

Further, healthy persons produce normocytic red blood cells and the amount of Hgb per cell lies within 26-32 pg.

Figure 13:
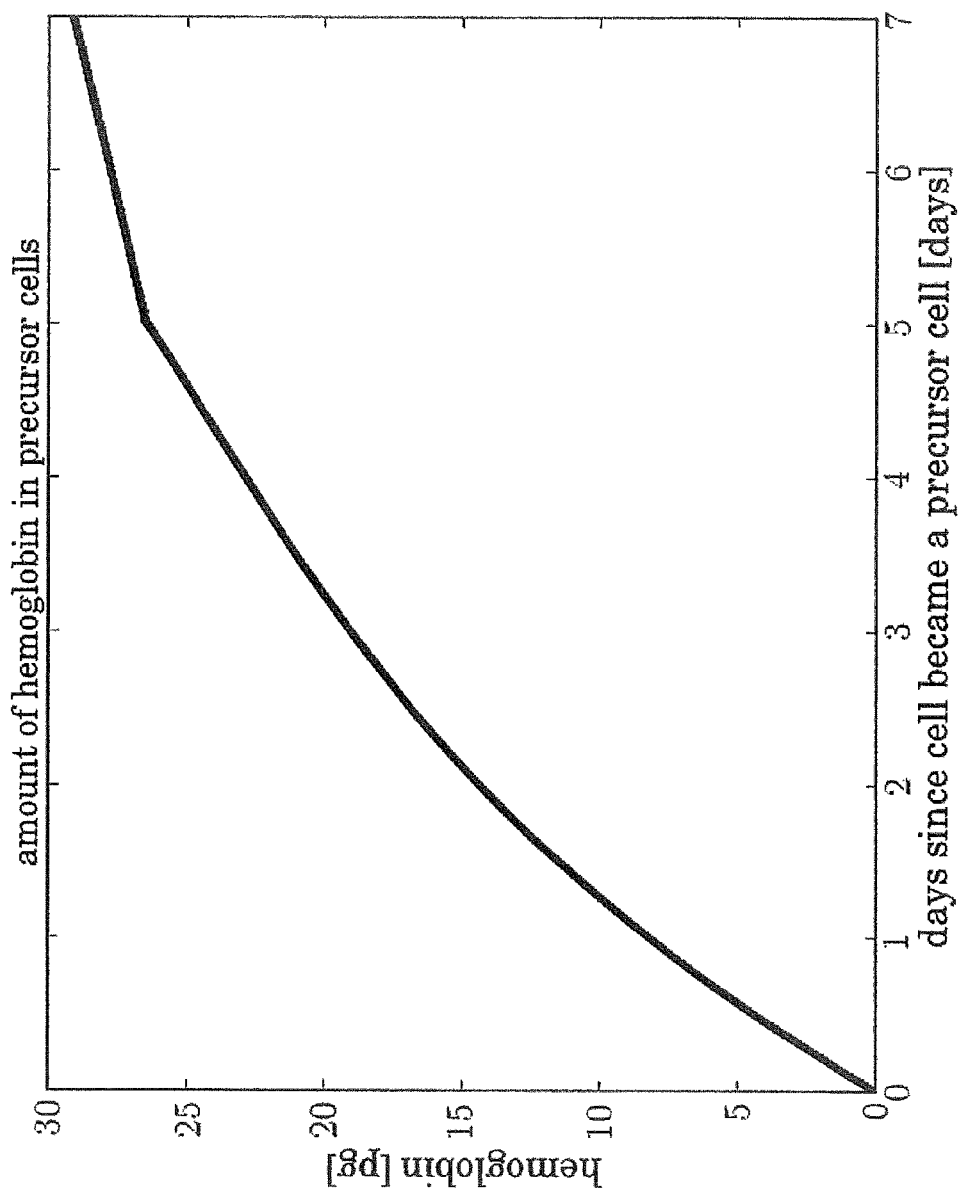
FIGS. 13 and 14A-14B are graphs of hemoglobin as a function of the calendric age of precursor cell, i.e., days since cell became a precursor cell. Depicted are a period of 6, 7 and 8 days.
Figure 14A:
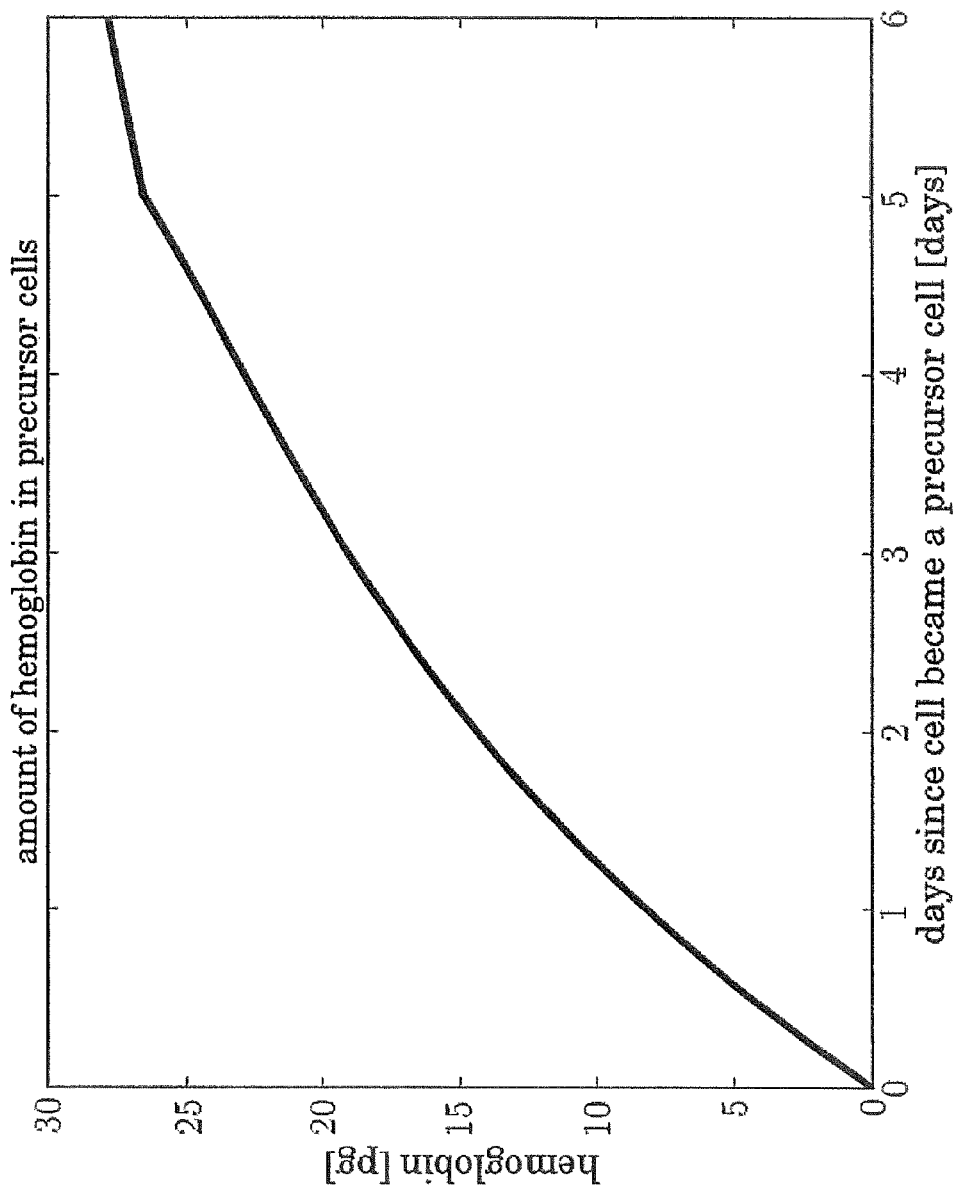
Figure 14B:
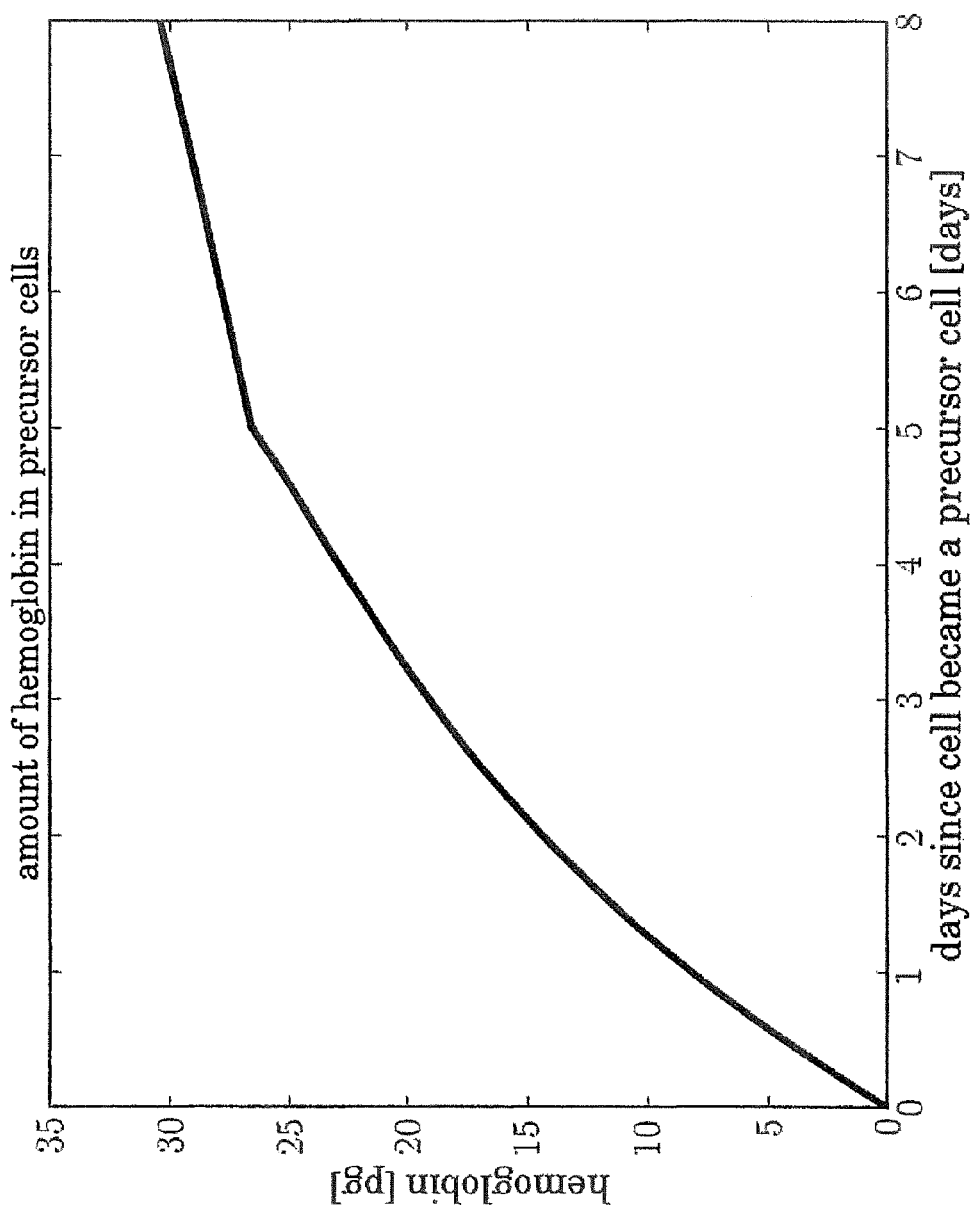

The contact rate d is chosen such that, under the above assumptions and by applying eqs. (19) and (21), respectively, the hemoglobin content of a cell lies well within this range when the cell leaves the reticulocyte population and enters the blood stream. FIG. 13 and FIGS. 14A-14B depict the accumulation of hemoglobin in precursor cells for d=0.215. Note that the label 'days since cell became a precursor cell' is similar to the calendric age $\eta$ and for erythroblast (day 0-5) coincides with the cell age, whereas for the reticulocytes the cell age and the calendric age might differ. Reticulocytes may stay in the bone marrow 1-3 days, but they all leave the bone marrow when they reach maximal maturity, i.e., when their cell age turns 2. This means that reticulocytes might have different timespans to gather iron and synthesize hemoglobin—depending on the maturation velocity v(E(t)), see Section 6.

Figure 15:
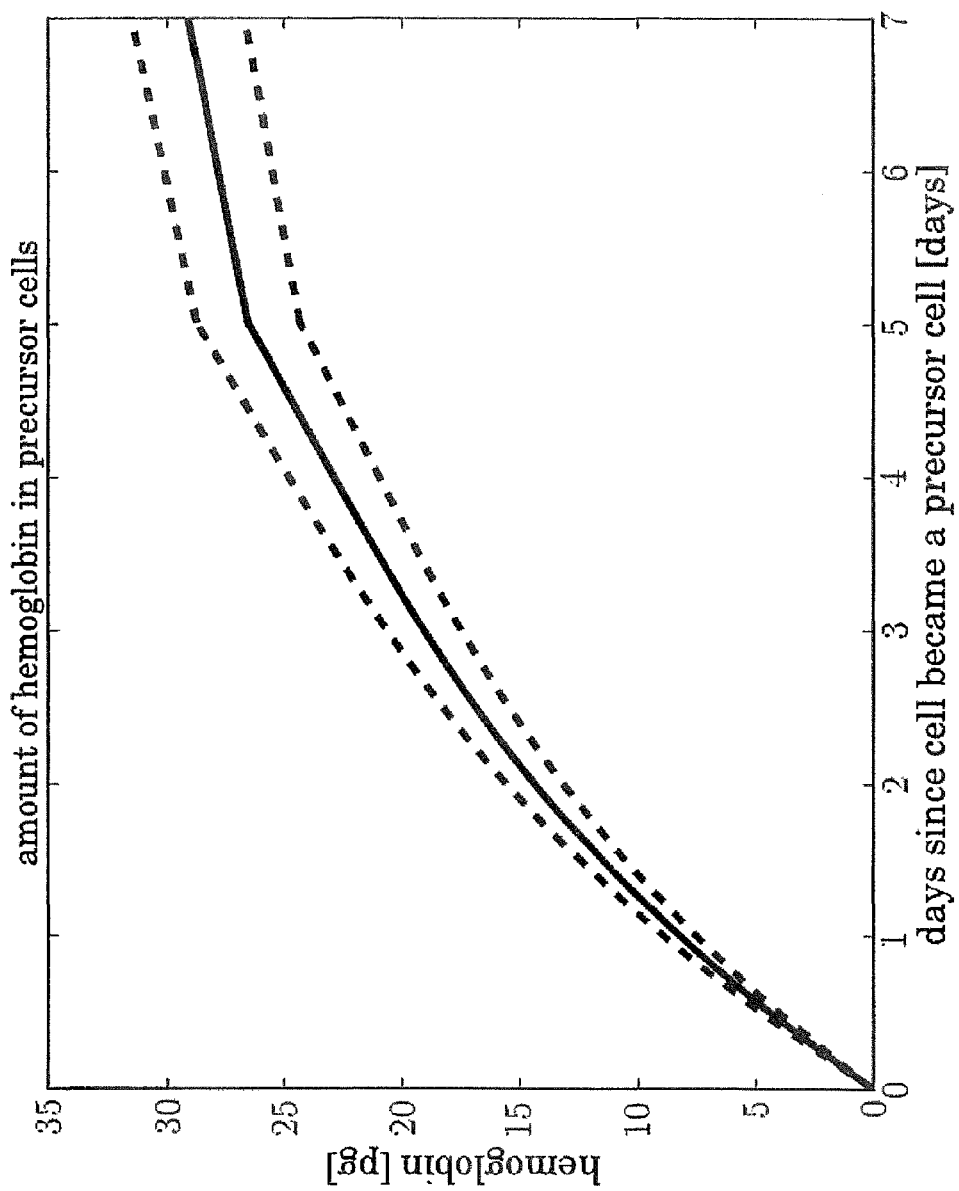
FIG. 15 is a graph of hemoglobin (pg) as a function of days since cell became a precursor cell (days), for a period of 7 days. Shown are a reference curve (solid line), that reflects the average hemoglobin accumulation in cells and two curves (dashed lines) that depict tolerable variations in this average, thereby forming a corridor of acceptable hemoglobin values around the average which acts as a reference curve.
Figure 16:
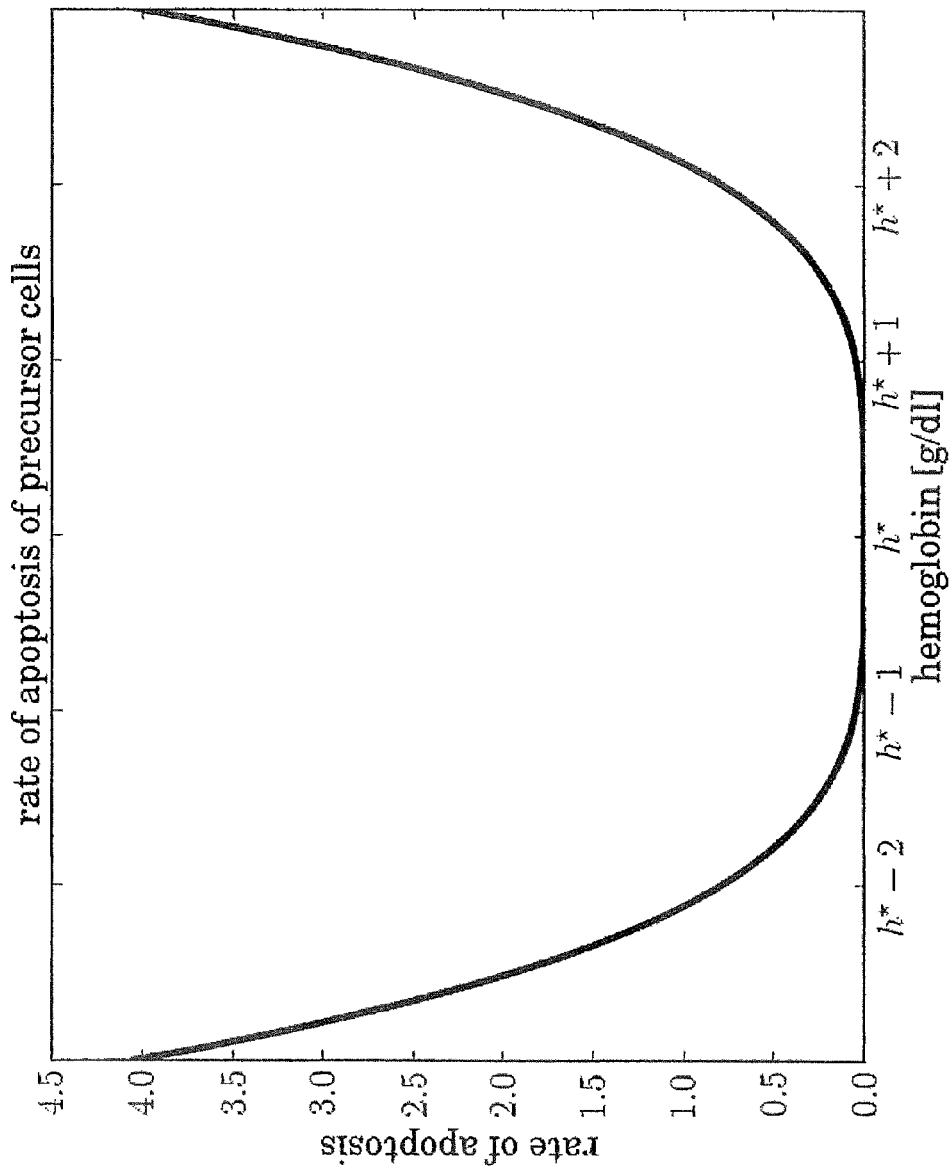
FIG. 16 is a graph of the rate of apoptosis as a function of hemoglobin concentration (g/dl) for a certain cell age.
Figure 17:
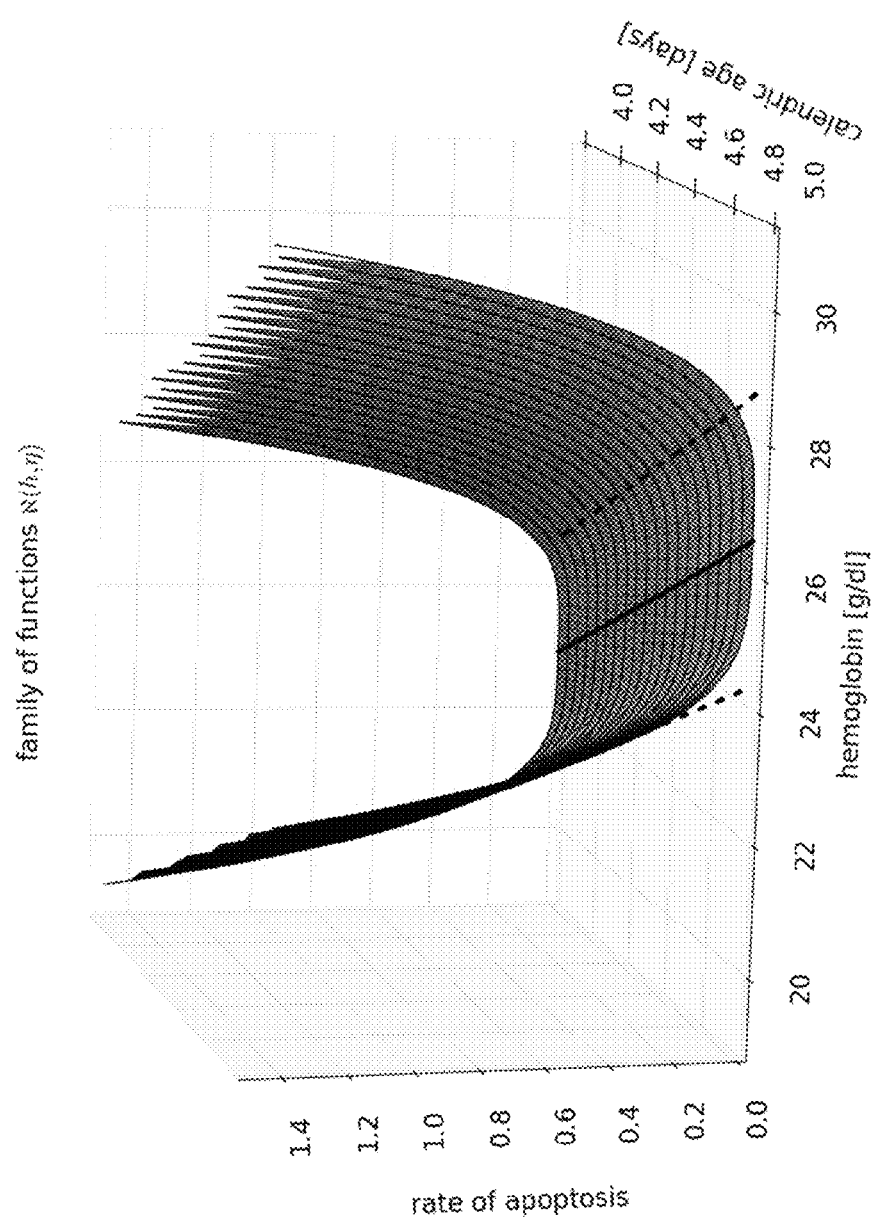
FIG. 17 illustrates the family of functions $\aleph(h,\eta)$. It is a graph of the rates of apoptosis as a function of hemoglobin concentration (g/dl) and calendric age (days). For exemplification, only calendric ages between 4-5 days are depicted. The solid line illustrates the hemoglobin reference curve, and the dash-dotted lines illustrate the corridor around this line (see FIG. 15).

Next, the reference curve is shifted, by slightly reducing or increasing, respectively, the amount of iron in plasma ($a_1 \equiv 2.75$ mg and $a_1 \equiv 3.25$ mg, respectively). The consequence being that a corridor develops around the reference curve. In FIG. 15 the reference curve is shown as a solid line and the shifted curves appear as dashed lines. The next step is to design functions in a way that cells that leave this corridor are more likely to die, the farther they diverge from it, the higher the rate of apoptosis gets. A family of functions is created that describes this increase in mortality as cells diverge from the reference curve $$\aleph(h, \eta) = (c_\aleph / (\eta+1)^3)(h - h^*(\eta))^4 \quad (22)$$

where $c_\aleph$ is a constant, h denotes the amount of hemoglobin that a cell carries at cell age/calendric-age $\eta$ and $h^*$ is the reference hemoglobin value at the age $\eta$. Polynomial functions of degree 4 are used to design this function, because one of their characteristics is that they have a flat bottom (i.e. apoptosis within the corridor is low) and then increase sharply. See FIG. 16 for a graphical depiction of the function $\aleph(\cdot, \bar{\eta})$ for a fixed calendric age $\bar{\eta}$. For a graphical description of the family of functions $\aleph$ that are created, see FIG. 17. Finally, to get the rate of apoptosis $\alpha$ for the precursor cells, a discrete set of N+1 equidistant data points $\mu_i$, i=0, . . . , N are defined along $\mu \in [\mu_{min}^r, \mu_{max}^s]$ at which the following calculations are done
  calculate the amount of Hgb $h_i$ in cells of age $\mu_i$ using eq. (19), (20) and (21),
  calculate the values of the function $\aleph$ at the grid points $\eta_i$ and the corresponding Hgb value $h_i$
  interpolate the resulting values using cubic splines.

Figure 18:
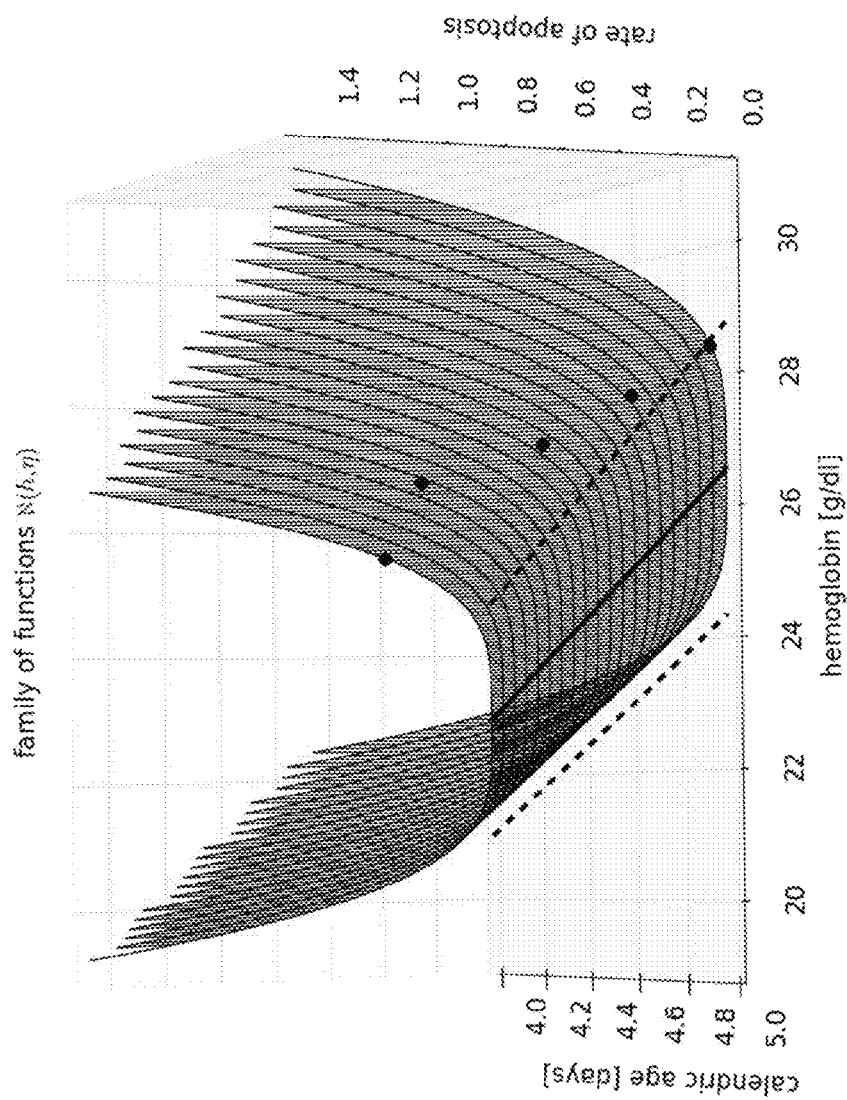
FIG. 18 is a graph describing the rates of apoptosis as a function of hemoglobin concentration (g/dl) and calendric age illustrating the evaluation of the functions $\aleph(h,\eta)$ at the grid points $\eta_i$ and the corresponding hemoglobin values $h_i$. The resulting values (large dots) are interpolated using cubic splines. For exemplification, only calendric ages between 4-5 days are depicted.
Figure 19:
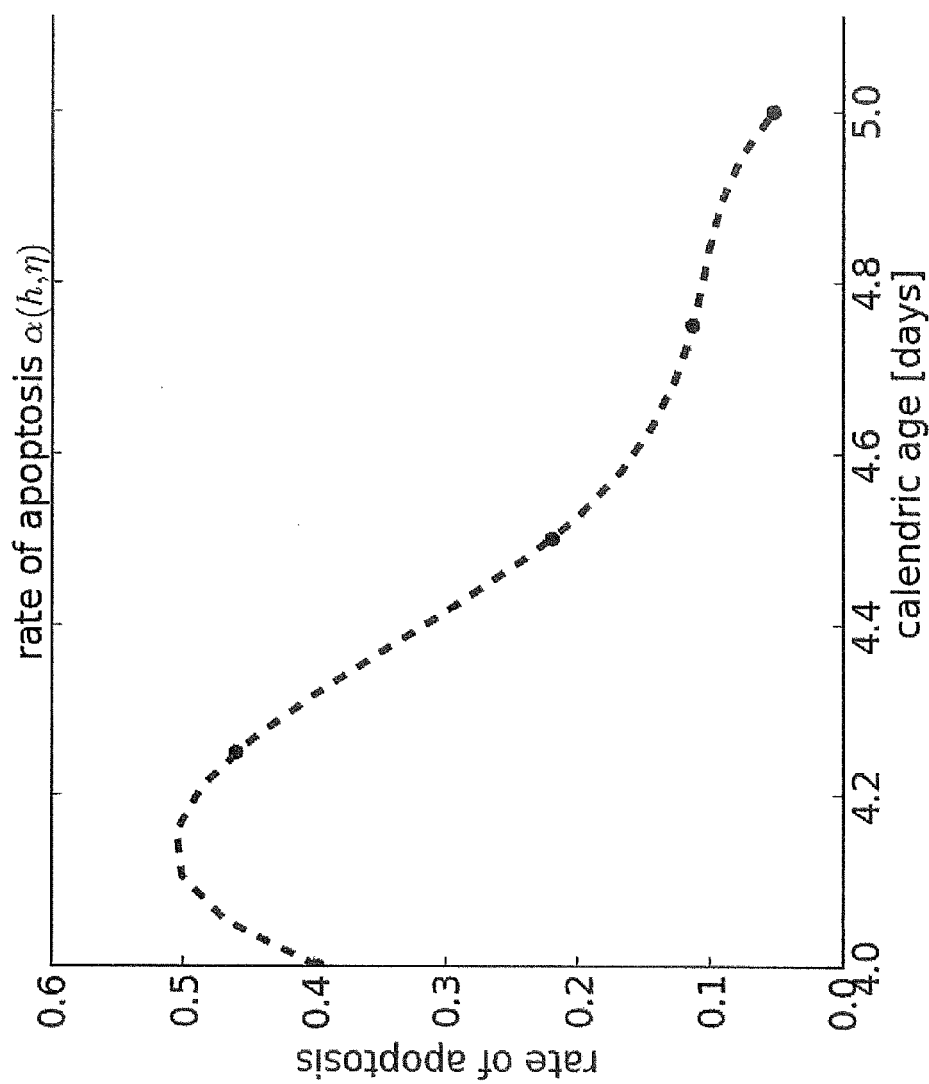
FIG. 19 is a graph of the rate of apoptosis as a function of calendric age (days), illustrating the computation of the apoptosis function $\alpha$. The values of the functions $\aleph$ at the discrete time points $\eta_i$ and the corresponding hemoglobin values $h_i$ (large dots) are interpolated using cubic splines (dashed line). The resulting curve represents the rate of apoptosis of the cells. The function is only plotted for a calendric age in a range of between 4 days and 5 days, for clarity.

The result is the function $\alpha(h, \eta)$ describing the rate of apoptosis of precursor cells shown in FIGS. 18 and 19. Note that the above calculations have to be repeated at every time step.

7.3. Detailed Description of the Iron Compartments.
7.3.1. Plasma (Compartment 1).

The rate at which iron enters erythroid cells at time t is given by $$d_1 a_1(t) \tau(t),$$

where the number of transferrin receptors $\tau$ on all precursor cells is $$\tau(t) = \int_{\mu_{min}^r}^{\mu_{max}^r} \varphi(\mu^r) r(t, \mu^r) \, d\mu^r + \int_{\mu_{min}^s}^{\mu_{max}^s} \varphi(\mu^s) s(t, \mu^s) \, d\mu^s,$$

where $\phi(\mu)$ is given by eq. (17). Further, $r(t, \mu^r)$ and $s(t, \mu^s)$ denote the population densities of hemoglobin synthesizing cells, erythroblasts and reticulocytes, respectively. At the same time this is the rate at which iron leaves the plasma compartment and enters the precursor cell compartment.

Only a very small amount of iron can be found in this pool (about 3 mg; ≤1%) bound to transferrin, but it is a very important compartment because of its rapid turnover rate. See Finch 1982. Iron normally turns over at least 10 times each day. See Williams Hematology. Inflow into the plasma compartment comes from macrophages, the storage pool, iron absorbed through the duodenum, and via intravenously administered iron. Outflow leaves the plasma compartment to the precursor cells and the storage compartment. The flow rates $k_{41}$, $k_{gastro,1}$ and $k_{51}$ are dependent on the hepcidin concentration $H(t)$ at time $t$. They decrease when the hepcidin level rises and vice versa. Inflammation and full iron stores increase the release of hepcidin from the hepatocytes in the liver, whereas a stressed erythropoiesis and depleted stores suppress the production of hepcidin. The outflow to the precursor cell compartment $k_{12}a_1$ is altered by the amount of iron needed from the cells to synthesize hemoglobin. As erythroid cells are only able to take up iron through transferrin receptors, their need for iron can be associated with the number of receptors expressed on precursor cells. Thus, the rate $k_{12}$ is given by $$k_{12} = d_1 \left( \int_{\mu_{min}^r}^{\mu_{max}^r} \varphi(\mu^r) r(t, \mu^r) d\mu^r + \int_{\mu_{min}^s}^{\mu_{max}^s} \varphi(\mu^s) s(t, \mu^s) d\mu^s \right).$$

For an explanation of the various terms see the statements about erythroblasts in Section 6.2. Hence, the change of amount of iron in the plasma compartment is $$\frac{d}{dt}a_1(t) =$$
$$k_{41}(H(t))a_4(t) + a_{iv,total}(t)\delta_{t_0}(t) + k_{gastro,1}(H(t))a_{gastro}(t) + k_{51}(H(t))a_5(t) -$$
$$k_{15}a_1(t) - d_1 \left( \int_{\mu_{min}^r}^{\mu_{max}^r} \varphi(\mu^r) r(t, \mu^r) d\mu^r + \int_{\mu_{min}^s}^{\mu_{max}^s} \varphi(\mu^s) s(t, \mu^s) d\mu^s \right) a_1(t).$$

The transfer rate $k_{41}(H(t))$ and $k_{51}(H(t))$ can be described by monotonically decreasing sigmoidal functions $$k_{41}(H(t)) = \frac{a_6 - b_6}{1 + e^{-k_6 H(t) + c_6}} + b_6, \quad (23)$$

and $$k_{51}(H(t)) = \frac{a_7 - b_7}{1 + e^{-k_7 H(t) + c_7}} + b_7, \quad (24)$$

respectively. The parameters $a_6$, $b_6$, $c_6$, $k_6$, $a_7$, $b_7$, $c_7$ and $k_7$ are positive constants with $a_6 > b_6$ and $a_7 > b_7$. The hepcidin level $H(t)$ at time $t$ is determined by eq. (13).

7.3.2. Precursor Cells (Compartment 2).

Inflow into the precursor cell compartment comes from plasma. One outflow of this compartment leaves to the erythrocytes compartment and describes the amount of hemoglobin carried from reticulocytes, which enter the blood stream. Thus, the flow $f_{23}(\bullet)$ from compartment 2 to compartment 3, is defined by the cells that leave the bone marrow and the amount of hemoglobin these cells are carrying. First, one has to compute how long cells that leave the bone marrow at time $t$ have actually stayed there as precursor cells. Hence, one needs to solve $f(\hat{t}, \mu_{max}^s)$ and one denotes the root of eq. (20) by $\eta_{max}^s$. Note that $\eta_{max}^s$ might change over time as reticulocytes are released in the blood stream faster or more slowly.

$$k_{23}a_2 = f_{23}(v^s(E(t))s(t,\mu_{max}^s), h^s(t,\eta_{max}^s)),$$

where $v^s(E(t))s(t,\mu_{max}^s)$ determines how many reticulocytes are leaving the bone marrow at a certain time $t$ and the function $h^s(t,\eta_{max}^s)$ indicates how much hemoglobin they carry. $v^s(E(t))$ is the maturation velocity of reticulocytes depending on EPO and $s(t,\mu_{max}^s)$ is the density of the reticulocyte population with maximal maturity $\mu_{max}^s$ at time $t$. The function $h^s(t,\eta_{max}^s)$ is given by eq. (21).

The second outflow of this compartment leaves to the macrophages and is defined by the precursor cells that die. Hence, the flow from compartment 2 to compartment 4 is defined by the amount of iron that dying cells carry, i.e.

$$k_{24}a_4 = \int_{\mu_{min}^r}^{\mu_{max}^r} \alpha(h, \mu^r) h(t, \mu^r) r(t, \mu^r) d\mu^r + \int_{\mu_{min}^s}^{\eta_{max}^s(t)} \alpha(h, \eta^s) h(t, \eta^s) s \left( t, \mu_{min} + \int_{t-\eta^s}^{t} v(E(s)) ds \right) d\eta^s. \quad (25)$$

For the first part of the above equation, $\eta$ and $\mu^r$ are exchangeable without any difficulties as, for erythroblasts, both describe the cell age of the cell, see Section 6.2.

Altogether the change of amount of iron in the iron-precursors compartment is given by $$\frac{d}{dt}a_2(t) = d_0 \left( \int_{\mu_{min}^r}^{\mu_{max}^r} \varphi(\mu^r) r(t, \mu^r) d\mu^r + \int_{\mu_{min}^s}^{\mu_{max}^s} \varphi(\mu^s) s(t, \mu^s) d\mu^s \right) a_1(t) -$$
$$f_{23}(v^s(E(t))s(t,\mu_{max}^s), h^s(t,\mu_{max}^s)) - \int_{\mu_{min}^r}^{\mu_{max}^r} \alpha(h, \mu^r) h(t, \mu^r) r(t, \mu^r) d\mu^r -$$
$$\int_{\mu_{min}^s}^{\eta_{max}^s(t)} \alpha(h, \eta^s) h(t, \eta^s) s \left( t, \mu_{min} + \int_{t-\eta^s}^{t} v(E(s)) ds \right) d\eta^s.$$

Note that it is not necessary to determine the function $f_{23}$ as, in fact, there is no need to explicitly observe the rate of change of the precursor cell compartment. The amount of iron $a_2(t)$ in this compartment at time $t$ can be directly computed from eqs. (19), (20), (21), and the population equations for the erythroblasts and reticulocytes. It is defined by the total number of precursor cells and the amount of hemoglobin they carry:

$$a_2(t) = \int_{\mu_{min}^r}^{\mu_{max}^r} \alpha(h, \mu^r) r(t, \mu^r) d\mu^r + \int_{\mu_{min}^s}^{\eta_{max}^s(t)} \alpha(h, \eta^s) h(t, \eta^s) s \left( t, \mu_{min} + \int_{t-\eta^s}^{t} v(E(s)) ds \right).$$

However, it is important to know the flux of hemoglobin to the macrophage compartment, which arises from dying cells, because this flux (see eq. (25)) is a source term in the macrophage compartment.

7.3.3. Erythrocytes (Compartment 3)

Inflow into the erythrocytes compartment comes from the precursor cell compartment, and iron leaves the compartment to the macrophages compartment (phagocytosis of senescent cells, random break-down of cells and neocytolysis)

$$k_{34}a_3 = \int_{\mu_{min}^m}^{\mu_{max}^m} h(t-\mu^m, \eta_{max}^s)\alpha^m(E(t), \mu^m)m(t, \mu^m)d\mu^m, \quad (26)$$

or is excreted via bleeding $$k_{3,out}a_3 = \int_{\mu_{min}^m}^{\mu_{max}^m} h(t-\mu^m, \eta_{max}^s)\alpha_{bleed}^m(t)m(t, \mu^m)d\mu^m.$$

An erythrocyte of age $\mu^m$ left the reticulocyte population at time $t-\mu^m$ and, making use of Assumption 42, the amount of hemoglobin it carries can be computed using eq. (21). Further, $\alpha^m$ denotes the mortality rate of erythrocytes due to phagocytosis of senescent cells, random break-down of cells, and neocytolysis. Furthermore, h is the amount of hemoglobin carried by a cell, $m(t,\mu^m)$ is the population density of erythrocytes with cell age $\mu^m$ at time t, and $\alpha_{bleed}^m(t)$ is the rate with which RBCs are lost due to bleeding.

Thus, the change of the amount of iron in the erythrocyte compartment is $$\frac{d}{dt}a_3(t) = f_{23}(v^s(E(t))s(t, \mu_{max}^s), h^s(t, \mu_{max}^s)) -$$
$$\int_{\mu_{min}^m}^{\mu_{max}^m} h(t-\mu^m, \eta_{max}^s)\alpha^m(E(t), \mu^m)m(t, \mu^m)d\mu^m -$$
$$\int_{\mu_{min}^m}^{\mu_{max}^m} h(t-\mu^m, \eta_{max}^s)\alpha_{bleed}^m(t)m(t, \mu^m)d\mu^m.$$

Similar to compartment 2, it is not necessary to observe the rate of change of the erythrocyte cell compartment to compute the amount of iron $a_3(t)$ at time t. The quantity $a_3(t)$ can be directly computed from the population class and is defined by the total number of circulating red blood cells and the amount of hemoglobin they carry:

$$a_3(t) = \int_{\mu_{min}^m}^{\mu_{max}^m} h(t-\mu^m, \eta_{max}^s)m(t, \mu^m)d\mu^m.$$

However, the term $k_{34}a_3(t)$ needs to be known explicitly (see eq. (26)). This flux, which is the rate of hemoglobin released by erythrocytes, appears as a source term in the macrophage compartment.

7.3.4 Macrophages (Compartment 4)

Inflow into the macrophages compartment comes from the erythrocytes compartment (erythrocytes phagocytosed by macrophages, iron set free by random break-down of RBCs and shedding of hemoglobin containing vesicles) and the precursor cells compartment. Outflow of this compartment leaves to the plasma and to the storage compartment. Therefore, the change of iron in the compartment is $$\frac{d}{dt}a_4(t) = \int_{\mu_{min}^r}^{\mu_{max}^r} \alpha(h, \mu^r)h(t, \mu^r)r(t, \mu^r)d\mu^r +$$
$$\int_{\mu_{min}^s}^{\eta_{max}^s(t)} \alpha(h, \eta^s)h(t, \eta^s)s\left(t, \mu_{min} + \int_{t-\eta^s}^t v(E(s))ds\right)d\eta^s +$$
$$\int_{\mu_{min}^m}^{\mu_{max}^m} h(t-\mu^m, \eta_{max}^s)\alpha^m(E(t), \mu^m)m(t, \mu^m)d\mu^m -$$
$$k_{41}(H(t))a_4(t) - k_{45}a_4(t),$$

where $k_{41}(H(t))$ is given by eq. (23).

7.3.5. Storage (Compartment 5)

Inflow into the storage compartment comes from the plasma and the macrophages compartment and iron leaves this compartment to the plasma compartment. Hence, the change of iron in the storage compartment is $$\frac{d}{dt}a_5(t) = k_{15}a_1(t) + k_{45}a_4(t) - k_{51}(H(t))a_5(t),$$

where $k_{51}(H(t))$ is given in eq. (24).

7.4. Mathematical Model—Iron Model

For the convenience of the reader, all equations of the Iron Model are collected in this section:

$$\frac{d}{dt}a_1(t) =$$
$$k_{41}(H(t))a_4(t) + a_{iv,total}(t)\delta_{t_0}(t) + k_{gastro,1}(H(t))a_{gastro}(t) + k_{51}(H(t))a_5(t) -$$
$$k_{15}a_1(t) - d_1\left(\int_{\mu_{min}^r}^{\mu_{max}^r} \varphi(\mu^r)r(t, \mu^r)d\mu^r + \int_{\mu_{min}^s}^{\mu_{max}^s} \varphi(\mu^s)s(t, \mu^s)d\mu^s\right)a_1(t),$$

$$a_2(t) = \int_{\mu_{min}^r}^{\mu_{max}^r} \alpha(h, \mu^r)r(t, \mu^r)d\mu^r -$$
$$\int_{\mu_{min}^s}^{\eta_{max}^s(t)} \alpha(h, \eta^s)h(t, \eta^s)s\left(t, \mu_{min} + \int_{t-\eta^s}^t v(E(s))ds\right)d\eta^s$$

$$a_3(t) = \int_{\mu_{min}^m}^{\mu_{max}^m} h(t-\mu^m, \eta_{max}^s)m(t, \mu^m)d\mu^m$$

$$\frac{d}{dt}a_4(t) = \int_{\mu_{min}^r}^{\mu_{max}^r} \alpha(h, \mu^r)h(t, \mu^r)r(t, \mu^r)d\mu^r +$$
$$\int_{\mu_{min}^s}^{\eta_{max}^s(t)} \alpha(h, \eta^s)h(t, \eta^s)s\left(t, \mu_{min} + \int_{t-\eta^s}^t v(E(s))ds\right)d\eta^s +$$
$$\int_{\mu_{min}^m}^{\mu_{max}^m} h(t-\mu^m, \eta_{max}^s)\alpha^m(E(t), \mu^m)m(t, \mu^m)d\mu^m -$$
$$k_{41}(H(t))a_4(t) - k_{45}a_4(t),$$

$$\frac{d}{dt}a_5(t) = k_{15}a_1(t) + k_{45}a_4(t) - k_{51}(H(t))a_5(t),$$

$$\frac{d}{dt}H(t) = \frac{1}{TBV}H_{prod}(t) - c_{deg}^H H(t),$$

where the initial values are given by $a_1(0)=a_{1,0}$,
$a_2(0)=a_{2,0}$,
$a_3(0)=a_{3,0}$,
$a_4(0)=a_{4,0}$,
$a_5(0)=a_{5,0}$,
$H(0)=H_0$.

Moreover, a number of auxiliary equations are needed $$k_{gastro,1}(H(t)) = \frac{a_5 - b_5}{1 + e^{-k_5 H(t) + c_5}} + b_5,$$

$$k_{41}(H(t)) = \frac{a_6 - b_6}{1 + e^{-k_6 H(t) + c_6}} + b_6,$$

$$k_{51}(H(t)) = \frac{a_7 - b_7}{1 + e^{-k_7 H(t) + c_7}} + b_7,$$

where the hepcidin feedback is given by $$H_{prod}(t) = \frac{a_H - b_H}{1 + e^{-k_H C(t) + c_H}} + b_H,$$

$$C(t) = -c_U U(t) + c_{a_5} a_5(t) + c_i i(t),$$

$$U(t) = \int_{\mu_{min}^r}^{\mu_{max}^r} r(t, \mu^r) d\mu^r + \int_{\mu_{min}^s}^{\mu_{max}^s} s(t, \mu^s) d\mu^s.$$

Furthermore, we have $$\varphi(\mu) = \begin{cases} 3.3016 \mu^3 - 32.127 \mu^2 + 74.0952\mu + 30, & \text{for } \mu \in [\mu_{min}^r, \mu_{max}^r], \\ 10, & \text{for } \mu \in [\mu_{min}^s, \mu_{max}^s], \end{cases}$$

$$h(t, \mu^r) = \frac{d}{TBV} \int_{t-\mu^r}^{t} \varphi(s - t + \mu^r) a_1(s) ds$$

$$h(t, \eta^s) = h(t - \eta^s + \mu_{min}^s, \mu_{max}^r) + \varphi \frac{d}{TBV} \int_{t-\eta^s + \mu_{min}^s}^{t} a_1(s) ds.$$

The calendric age $\eta$ of cells is calculated using $$f(\bar{t}, \bar{\mu}) = \mu_{min} - \bar{\mu} + \int_{\bar{t}}^{\bar{t}} v(E(s)) ds,$$

and $\eta = t - \hat{t}$.

Further, to create the function $\alpha(h, \eta)$ (for $\eta$ either $\mu^r$ or $\eta^s$ can be inserted) a discrete set of N+1 equidistant data points $\mu_i$, $i=0, \ldots, N$, along $\mu \in [\mu_{min}^r, \mu_{max}^s]$ is defined and at every time step the following calculations are done calculate the amount of Hgb $h_i$ in cells of age $\mu_i$ using the formula for $\eta$, $f(t, \mu)$, $h(t, \mu^r)$ and $h(t, \eta^s)$, calculate the values of the function $\aleph$ at the grid points $\eta_i$ and the corresponding Hgb value $h_i$ $$\aleph(h, \eta) = (c_\aleph / (\eta + 1)^3)(h - h^*(\eta))^4$$

interpolate the resulting values using cubic splines.

Derivation of Population Equations

A.1. Population Equations with One Structural Variable.

Let $u(t, \cdot)$ denote the density of the population at time t, i.e., for $0 \leq a < b$, $\int_a^b u(t, x) dx$ is the number of cells with maturity level $x \in [a, b]$. The rate of change is $$\frac{d}{dt} \int_a^b u(t, x) dx = \int_a^b u_t(t, x) dx, \; t \geq 0, \; 0 \leq a < b. \tag{A.1}$$

Here, u is assumed to be continuously differentiable with respect to t. The rate of change with respect to t of the number of cells with maturity level in [a,b] is the sum of several components:

the flux of cells across the boundary points a and b at time t because of changing maturity;

the rate at which cells with maturity in [a,b] die at time t;

the rate at which cells with maturity in [a,b] proliferate.

a) Flux Across a and b.

The flux of cells across maturity level is denoted x at time t by $q(t, x)$ and assume that the maturity of a cell is changing according to $$\dot{x}(t) = v(t, x(t)), \; t \geq 0,$$

where the "velocity" v is continuous in t and Lipschitzean with respect to x, $t \geq 0$, $0 \geq 0$. Moreover, it is assumed that $v(t, x) > 0$, i.e., the maturity of a cell is always strictly increasing.

Then the flux of cells across a maturity level x is given by $$q(t, x) = v(t, x) u(t, x), \; t \geq 0, \; x \geq 0.$$

Consequently, the net flux of cells at time t into the interval [a, b] is $$q(t, a) - q(t, b) = v(t, a) u(t, a) - v(t, b) u(t, b) \tag{A.2}$$

$$= -\int_a^b ((v(t, x) u(t, x))_x dx, \; t \geq 0.$$

b) Mortality.

Let $x_i^N = a + i \Delta x$, $i = 0, \ldots, N$, with $\Delta x = (b - a)/N$ be a uniform mesh on [a, b]. By the mean value theorem for integrals, the number of cells with maturity level $x \in [x_i^N, x_{i+1}^N]$ at time t for some $x^*_i \in [x_i^N, x_{i+1}^N]$ is given by $$u(t, x^*_i) \Delta x.$$

The rate at which cells with maturity in $[x_i^N, x_{i+1}^N]$ die at time t is assumed to be proportional to the number of cells with maturity in this interval and therefore is given by $$\alpha(t, x^{**}_i) u(t, x^*_i) \delta x,$$

where $\alpha(t, x) \geq 0$, $t \geq 0$, $x \geq 0$, is the mortality rate which is assumed to be a continuous function and $x^{**}_i \in [x_i^N, x_{i+1}^N]$. Summing $i = 0, \ldots, N-1$ and taking $N \to \infty$ yields $$\int_a^b \alpha(t, x) u(t, x) dx, \; t \geq 0, \tag{A.3}$$

for the rate at which cells with maturity level in [a, b] die at time t.

c) Proliferation.

The assumption concerning proliferation is that a cell with maturity level x dividing at time t gives rise to two daughter cells with maturity x. By analogous considerations as in the case of mortality, the following expression is obtained for the rate at which cells enter the interval [a, b] at time t because of proliferation:

$$2 \int_a^b \beta(t, x) u(t, x) dx - \int_a^b \beta(t, x) u(t, x) dx = \int_a^b \beta(t, x) u(t, x) dx,$$
$$t \geq 0, \tag{A.4}$$

where $\beta(t, x) \geq 0$ $t \geq 0$, $x \geq 0$, is the proliferation rate in the population which is assumed to be continuous.

d) The Model.

Using (A.1)-(A.4) yields $$\int_a^b u_t(t, x) dx = -\int_a^b ((v(t, x) u(t, x))_x dx - \int_a^b \alpha(t, x) u(t, x) dx + \int_a^b \beta(t, x) u(t, x) dx, \; t \geq 0, \; x \geq 0.$$

Assuming that the integrands in the above integrals are continuous and observing that the interval $[a, b] \subset R_+$ is arbitrary yields $$u_t(t, x) + ((v(t, x) u(t, x))_x = (\beta(t, x) - \alpha(t, x)) u(t, x), \; t \geq 0, \; x \geq 0. \tag{A.5}$$

In addition to this equation, an initial condition needs to be prescribed as $$u(0,x)=u_0(x), x \geq 0$$

and a boundary condition for x=0. Assuming v(t,0)>0, t≥0, this boundary condition is written as a flux condition at x=0:

$$v(t,0)u(t,0)=f_0(t), t \geq 0.$$

A.2. Population Equations with Several Structural Variables.

Models for populations structured by several attributes can be derived analogously to those for populations with just one attribute. For simplicity of notation, populations are restricted to three structural variables and cell populations with the attributes cell age x, amount of hemoglobin in the cell y, and amount of transferrin receptors on the cell membrane z are considered.

Let u(t,x,y,z) be the density of the cell population and $\Omega$ be a subset of the positive cone $R_+^3$ in $R^3$ which is the admissible set for the attributes. Then the number of cells with attributes $(x,y,z) \in \Omega$ at time t is given by $$\int_\Omega u(t,x,y,z) d\omega.$$

Of interest is the rate at which the number of cells with attributes in $\Omega$ at time t changes, i.e., in the quantity $$\frac{d}{dt} \int_\Omega u(t,x,y,z) d\omega = \int_\Omega u_t(t,x,y,z) d\omega, \quad (A.6)$$

where it is assumed that u is continuously differentiable with respect to t. The rate at which the number of cells with attributes in $\Omega$ changes at time t is composed of several components:
- the flux of cells across $\partial\Omega$ because the attributes change;
- the rate at which cells with attributes in $\Omega$ die at time t;
- the rate at which cells enter or leave $\Omega$ at time t because of proliferation.

a) Flux Across $\partial\Omega$.

The attributes of a cells change according to $$\dot{x}(t)=f(t,x(t),y(t),z(t)),$$

$$\dot{y}(t)=g(t,x(t),y(t),z(t)),$$

$$\dot{z}(t)=h(t,x(t),y(t),z(t)), \quad (A.7)$$

where $f$, g, h are functions $R_+ \times R_+^3 \to R$ which are continuous with respect to t and Lipschitzean with respect to x, y, z. Then the flux of cells at time t and at $(x,y,z) \in R_+^3$ is given by $$F(t, x, y, z) = u(t, x, y, z) \begin{pmatrix} f(t, x, y, z) \\ g(t, x, y, z) \\ h(t, x, y, z) \end{pmatrix}.$$

Consequently the flux of cells across $\partial\Omega$ at time t is given by $$\int_{\partial\Omega} \langle F(t,x,y,z), v(x,y,z) \rangle \, d\sigma, \quad (A.8)$$

where v(x,y,z) denotes the unit outside normal to $\partial\Omega$ at the point (x,y,z). By Gauss' integral theorem we get $$\int_{\partial\Omega} \langle F(t,x,y,z), v(x,y,z) \rangle d\sigma = \quad (A.9)$$

-continued $$\int_\Omega \mathrm{div} F(t,x,y,z) d\omega = \int_\Omega ((f(t,x,y,z)u(t,x,y,z))_x + (g(t,x,y,z)u(t,x,y,z))_y + (h(t,x,y,z)u(t,x,y,z))_z) d\omega.$$

b) Mortality.

Let $\Omega = \bigcup_{i=1}^N \Omega_i$ such that diam $\Omega_i \leq \epsilon$, i=1, ..., N. By the mean value theorem for integrals, the number of cells with attributes in $\Omega_i$ at time t is given by $u(t,x^*_i,y^*_i,z^*_i)\Delta\Omega_i$, where $\Delta\Omega_i$ denotes the volume of $\Omega_i$ and $(x^*_i,y^*_i,z^*_i) \in \Omega_i$. It is assumed that the rate at which cells with attributes in $\Omega_i$ die at time t is proportional to the number of cells with attributes in $\Omega_i$ at time t, i.e., it is given by $$\alpha(t,x^{}_i,y^{}_i,z^{**}_i)u(t,x^*_i,y^*_i,z^*_i),$$

where $(x^{}_i,y^{}_i,z^{**}_i)$, $(x^*_i,y^*_i,z^*_i) \in \Omega_i$ and $\alpha(t,x,y,z)$ is the mortality rate, i.e., the rate at which cells with attributes (x,y,z) die at time t. Summing up and taking $\epsilon \to 0$, the rate at which individuals with attributes in $\Omega$ die at time t is given by $$\int_\Omega \alpha(t,x,y,z) u(t,x,y,z) d\omega. \quad (A.10)$$

c) Proliferation.

A basic assumption for proliferation is that division at time t of a cell with cell age x, amount of hemoglobin y and amount of transferrin receptors z results in two cells each with cell age x, amount of hemoglobin y/2 and amount of transferrin receptors z/2. Furthermore, the rate at which cells with attributes (x,y,z) divide at time t is assumed to be given by $\beta(t,x,y,z)$.

For a subset $\Omega \subset R_+^3$ the subsets $\Omega^{(1/2)}$, $\Omega^{(2)} \subset R_+^3$ are defined by $$\Omega^{(1/2)} = \{(x,y,z) | (x,2y,2z) \in \Omega\}, \Omega^{(2)} = \{(x,y,z) | (x,y/2,z/2) \in \Omega\}.$$

From now on, it is assumed that $$\Omega^{(1/2)} \cap \Omega = \emptyset \text{ and } \Omega^{(2)} \cap \Omega = \emptyset. \quad (A.11)$$

The following results are important when the equations governing the development of a structured population are derived:

Lemma A.1 For any $(x_0,y_0,z_0) \in R_+^3$ with $y_0 > 0$ or $z_0 > 0$ there exists a subset $\Omega \subset R_+^3$ with $(x_0,y_0,z_0) \in \Omega$ satisfying condition (A.11).

Proof. The case $y_0 > 0$ is the only case considered. For $\epsilon = y_0/3 > 0$, set $$\Omega = \{(x,y,z) \in R_+^3 | |x-x_0| < \epsilon, |y-y_0| < \epsilon, |z-z_0| < \epsilon\}$$

and assume that $(x,y,z) \in \Omega \cap \Omega^{(1/2)}$. By the definition of $\Omega^{(1/2)}$, this is equivalent to $$|x-x_0| < \epsilon, |y-y_0| < \epsilon, |2y-y_0| < \epsilon, |z-z_0| < \epsilon, \text{ and } |2z-z_0| < \epsilon.$$

The inequalities for y and the definition of $\epsilon$ imply that $y > y_0 - \epsilon = 2y_0/3$ and $y < (y_0+\epsilon)/2 = 2y_0/3$, a contradiction, which proves that $\Omega^{(1/2)} \cap \Omega = \emptyset$. The proof for $\Omega^{(2)} \cap \Omega = \emptyset$ is analogous.

The rate of change of the number of cells with attributes in $\Omega$ due to proliferation equals the rate at which the daughter cells of cells with attributes in $\Omega^{(2)}$ move into $\Omega$ minus the rate at which the daughter cells of cells with attributes in $\Omega$ leave $\Omega$ (and move to $\Omega^{(1/2)}$). By analogous considerations as in the case of the effect of mortality, the following expression is obtained for the rate at which the number of cells with attributes in $\Omega$ changes because of proliferation:

$$2\int_{\Omega^{(2)}} \beta(t,\tilde{x},\tilde{y},\tilde{z}) d\tilde{\omega} - \int_\Omega \beta(t,x,y,z) u(t,x,y,z) d\omega = 8\int_\Omega \beta(t,x,2y,2z) u(t,x,2y,2z) d\omega - \int_\Omega \beta(t,x,y,z) u(t,x,y,z) d\omega \quad (A.12)$$

d) The model.

Using (A.6), (A.9), (A.10) and (A.12) yields $$\int_\Omega u_t(t,x,y,z)d\omega = -\int_\Omega ((f(t,x,y,z)u(t,x,y,z))_x + (g(t,x,y,z)u(t,x,y,z))_y + (h(t,x,y,z)u(t,x,y,z))_z)d\omega - \int_\Omega (\alpha(t,x,y,z) + \beta(t,x,y,z))u(t,x,y,z)d\omega + 8\int_\Omega \beta(t,x,2y,2z)u(t,x,2y,2z)d\omega.$$

Assuming that the integrands in the above integrals are continuous and using Lemma 1 yields $$u_t(t, x, y, z) + (f(t, x, y, z)u(t, x, y, z))_x + \quad (A.13)$$

$$(g(t, x, y, z)u(t, x, y, z))_y + (h(t, x, y, z)u(t, x, y, z))_z =$$

$$-(\alpha(t, x, y, z) + \beta(t, x, y, z))u(t, x, y, z) +$$

$$8\beta(t, x, 2y, 2z)u(t, x, 2y, 2z), t \geq 0, x > 0, y > 0, z > 0.$$

An initial condition is prescribed $$u(0,x,y,z)=u_0(x,y,z),\ x>0,\ y>0,\ z>0,$$

and boundary conditions which, because of their special form, are considered directly in Section 2.

A.3. List of Parameters for Models Described in Sections 6 and 7

TABLE 4

List of parameters and their meaning.

| Parameter | Meaning |
|---|---|
| $\beta^p$ | proliferation rate for BFU-E cells |
| $\beta^q$ | proliferation rate for CFU-E cells |
| $\beta^r$ | proliferation rate for erythroblasts |
| $\mu_{max}^p$ | maximal maturity for BFU-E cells |
| $\mu_{min}^q$ | minimal maturity for CFU-E cells |
| $\mu_{max}^q$ | maximal maturity for CFU-E cells |
| $\mu_{min}^r$ | minimal maturity for erythroblasts |
| $\mu_{max}^r$ | maximal maturity for erythroblasts |
| $\mu_{min}^s$ | minimal maturity for marrow reticulocytes |
| $\mu_{max}^s$ | maximal maturity for marrow reticulocytes |
| $\alpha_{rand}^m$ | intrinsic mortality rate for erythrocytes |
| $a_1, b_1, c_1, k_1$ | constants for the sigmoid apoptosis rate for CFU-E cells |
| $a_2, b_2, c_2, k_2$ | constants for the sigmoid maturation velocity for marrow reticulocytes |
| $d_1$ | rate constant for transferrin to bind to its receptor |
| $d$ | rate constant with which hemoglobin is synthesized after transferrin bound to the TfR |
| $a_3, b_3, c_3, k_3$ | constants for the sigmoid function governing the release of endogenous EPO |
| $\mu_{min}^{m,n}$ | lower bound of erythrocytes which are possibly exposed to neocytolysis |
| $\mu_{max}^{m,n}$ | lower bound of erythrocytes which are possibly exposed to neocytolysis |
| $\mu_{max}$ | maximal life span for erythrocytes |
| $c_E$ | constant in the mortality rate for erythrocytes |
| $\tau_E$ | EPO threshold for neocytolysis |
| $c_{deg}^{end}$ | degradation rate of EPO released by the kidneys |
| $c_{deg}^{ex}$ | degradation rate of administered EPO (Epoetin alfa) |
| $S_0$ | number of cells committing to the erythroid lineage |
| TBV | total blood volume |
| $a_4, b_4, c_4, k_4$ | constants for the polynomial function describing the number of TfR expressed on erythroblasts |
| $\eta$ | calendric age of the cell |
| $\eta^s$ | calendric age of the reticulocyte |
| $c_x$ | constant in the function describing the apoptosis rate for cells with age $\eta$ at time t |
| $h^*$ | reference hemoglobin value |
| $k_{ij}$ | transfer rates from iron compartment i to iron compartment j |
| $a_{iv}$ | the amount of iron administered intravenously |
| $a_{gastro}$ | the amount of iron in the duodenum |
| $a_5, b_5, c_5, k_5$ | constants for the sigmoid function governing the flow rate from the duodenum into the plasma compartment |

TABLE 4-continued

List of parameters and their meaning.

| Parameter | Meaning |
|---|---|
| $a_H, b_H, c_H, k_H$ | constants for the sigmoid function governing the release of hepcidin by the liver |
| $c_U, c_{a5}, c_i$ | constants for the auxiliary equation used in the sigmoid function governing the release of hepcidin by the liver |
| $c_{deg}^H$ | degradation rate of hepcidin |
| $a_6, b_6, c_6, k_6$ | constants for the sigmoid function describing the flow rate from the macrophages into the plasma compartment |
| $a_7, b_7, c_7, k_7$ | constants for the sigmoid function governing the flow rate from the storage into the plasma compartment |

A.4. Derivation of the Hgb Accumulation Function.

Let $h(t,\mu)$ respectively $\phi(\mu)$ denote the amount of hemoglobin in a cell of maturity $\mu \geq \mu_{min}$ at time $t \in R$ respectively the number of transferrin receptors on the membrane of a cell of maturity $\mu \geq \mu_{min}$. Then the rate at which $h(t,\mu)$ changes in time is given by $$\frac{d}{dt}h(t, \mu(t)) = \frac{\partial}{\partial t}h(t, \mu(t)) + \frac{\partial}{\partial \mu}h(t, \mu(t))v(t) = d\phi(\mu(t))a_1(t), \quad (A.4.1)$$

$$t \in R,$$

where $d>0$ is a constant, $a_1(t)$ denotes the iron concentration in plasma at time t and $v(t)$ is the velocity at which the maturity of a cell increases, $v(t)=\dot{\mu}(t)$. For equation (A.4.1) one has the boundary condition $$\mu(t,\mu_{min}) \equiv 0, t \in R. \quad (A.4.2)$$

We solve the problem (A.4.1), (A.4.2) using the method of characteristics. Let $s \to (t(s), \mu(s), u(s))$, $s \geq 0$, be the characteristic through a point $(t_0, \mu_{min}, 0)$. Then the functions $t(s)$, $\mu(s)$ and $u(s)$ are solutions of the following initial value problem ("prime(')"=d/ds):

$$t'(s)=1,\ t(0)=t_0,$$

$$\mu'(s)=v(t(s)),\ \mu(0)=\mu_{min},$$

$$u'(s)=d\phi(\mu(s))a_1(t(s)),\ u(0)=0. \quad (A.4.3)$$

This gives, for $s \geq 0$, $$t(s)=t_0+s, \quad (A.4.4)$$

$$\mu(s)=\mu_{min}+\int_0^s v(t_0+\sigma)d\sigma, \quad (A.4.5)$$

$$u(s)=h(t(s), \mu(s))=d\int_0^s \phi(\mu_{min}+\int_0^\sigma v(t_0+\rho)d\rho)a_1(t_0+\sigma)d\sigma. \quad (A.4.6)$$

In order to determine $h(\bar{t},\bar{\mu})$ with $\bar{t} \in R$ and $\bar{\mu} \geq \mu_{min}$ one has to compute two numbers $\bar{s} \geq 0$ and $\hat{t} \in R$ such that $\bar{t}=t(\bar{s})$, $\bar{\mu}=\mu(\bar{s})$ and $h(\bar{t},\bar{\mu})=u(\bar{s})$ where $t(\cdot)$, $\mu(\cdot)$ and $u(\cdot)$ solve system (A.4.3) with $t_0=\hat{t}$. From equations (A.4.4) and (A.4.5) for s=$\bar{s}$ we get $$\hat{t}=\bar{t}-\bar{s},\ \bar{\mu}=\mu_{min}+\int_0^{\bar{t}-\hat{t}} v(\hat{t}+\sigma)d\sigma=\mu_{min}+\int_{\hat{t}}^{\bar{t}} v(\sigma)d\sigma.$$

This implies $\bar{s}=\bar{t}-\hat{t}$ and that $\hat{t}$ has to satisfy the equation $$g(\hat{t}):=\int_{\hat{t}}^{\bar{t}} v(\sigma)d\sigma=\bar{\mu}-\mu_{min}. \quad (A.4.7)$$

The function $\hat{t} \to g(\hat{t})$ is monotonically decreasing with $g(\bar{t})=0$. Equation (A.4.7) has a unique solution $\hat{t} \leq \bar{t}$ if, for instance, $v(t) \geq \delta$ for $t \in [T, \hat{t}]$ with $\delta T \geq \mu_{max}-\mu_{min}$ or if for some $t^* \in R$ one has $$\int_{-\infty}^{t^*} v(\sigma)d\sigma=\infty.$$

In case v≡1 one gets $\bar{\mu}=\mu_{min}+\bar{t}-\hat{t}$ and $\bar{s}=\bar{t}-\hat{t}$, i.e., $\hat{t}=\bar{t}-(\bar{\mu}-\mu_{min})$ and $\bar{s}=\bar{\mu}-\mu_{min}$.

Furthermore, one has $h(\bar{t},\bar{\mu})=u(\bar{s})=d\int_0^{\bar{\mu}-\mu_{min}}\phi(\mu_{min}+\sigma)a_1(\sigma+\bar{t}-(\bar{\mu}-\mu_{min}))d\sigma=d\int_{-(\bar{\mu}-\mu_{min})}^{0}\phi(\bar{\mu}+\sigma)a_1(\bar{t}+\sigma)d\sigma$.

Anemia of Renal Disease

Anemia affects almost all patients with chronic kidney disease (CKD). It is caused by failure of renal excretory and endocrine function. It often develops once renal function decreases to 50% and the degree of anemia increases with severity of renal failure. See Strippoli, et. al. Anemia develops because of a deficiency in endogenous erythropoietin production by the kidneys, increased blood losses, functional or absolute iron deficiency and decreased red cell survival. See J. B. Wish, *Clinical Journal of the American Society of Nephrology*, 1:S4-S8, 2006. Concerning endogenous erythropoietin production by the kidneys, one has to note that kidneys of end-stage renal disease patients can still produce some EPO, and thus can maintain higher hemoglobin levels than those found in anephric patients. Reasons for blood losses can be purpura, gastrointestinal and gynecologic bleeding (which occur in one third to one half of all CKD patients), frequent blood sampling, blood left in the extracorporeal circuit, multiple vascular surgeries, etc. Furthermore, neocytolysis contributes to renal anemia and it explains the often demonstrable hemolytic component and the worsening of hemolysis with more pronounced renal disease. A description of neocytolysis is provided above. It further explains the responsiveness of hemolysis to ESA therapy and the increased efficiency of subcutaneous (s.c.) compared to intravenous therapy (i.v.), because in s.c. administration nadirs in EPO levels which precipitate neocytolysis are avoided. See Rice 1999. In general, renal anemia is normocytic and normochromic and the number of reticulocytes is normal or slightly decreased, which is inappropriate in the context of a reduced RBC population. Certain deficiency states, especially iron, but also folate or vitamin $B_{12}$ deficiency may alter the nature of the anemia. See Finch 1982; M. Polenakovic and A. Sikole, *Journal of American Society of Nephrology*, 7:1178-1182, 1996.

Untreated anemia is associated with decreased oxygen delivery to the tissues. For compensatory reasons, cardiac output increases, resulting in left ventricular hypertrophy. Cardiac disease is the most common cause of death among patients who are on maintenance dialysis. Partial correction of anemia in these patients was shown to reduce cardiac ischemia and ameliorate cardiomegaly, thus reducing cardiac related morbidity. See A. Besarab, W. K. Bolton, J. K. Browne, J. C. Egrie, A. R. Nissenson, D. M. Okamoto, S. J. Schwab, and D. A. Goodkin, *The New England Journal of Medicine*, 339:584-590, 1998. Further consequences of uncorrected anemia are decreased cognition and mental acuity and overall decrease in patient welfare.

ESA Therapy

Erythropoiesis stimulating agents have been used to treat anemia in patients suffering from chronic renal failure for more than two decades. Optimal hemoglobin targets are still a matter of discussion. Studies have shown (see e.g. Singh et al.; Strippoli et al., R. N. Foley, B. M. Curtis, and P. S. Parfrey. *Clinical Journal of the American Society of Nephrology*, 4:726-733, 2009 (hereinafter "Foley et al.") that a partial correction of anemia is preferable to a full correction. A number of complications can occur in patients with CKD when they have near-normal/normal hemoglobin levels, i.e., higher vascular access thrombosis, hypertension and greater requirements for antihypertensives, cardiovascular events, earlier need for renal replacement therapy and higher mortality. Normal hemoglobin levels for women are in a range of between about 12 g/dl and 16 g/dl, and in a range of between about 13 g/dl and about 17.5 g/dl for men.

Defining an optimal hemoglobin target is not the only issue regarding ESA therapy. Another problem is: how can the target hemoglobin be achieved and how to keep the patient near this hemoglobin level over a long time period? The dose and frequency of administration of an ESA treatment regimen are most often determined based on the prior experience of the physician and on established guidelines. This approach bears some limitations and level of hemoglobin tends to fluctuate greatly and cycling phenomena are observed. An analysis of 31,267 patients on hemodialysis in the Fresenius Medical Care-North America database found that only 5% of patients persistently remained within a desired Hb range of 11-12 g/dl for a period of 6 months. See A. J. Collins, R. M. Brenner, J. J. Ofman, E. M. Chi, N. Stuccio-White, M. Krishnan, C. Solid, N. J. Ofsthun, and J. M. Lazarus. *American Journal of Kidney Diseases*, 46:481-488, 2005 (hereinafter "Collins et al."). Fishbane et al. analyzed data of dialysis patients collected over five years in a hospital and came to a similar conclusion. See S. Fishbane and J. S. Berns. *Kidney International*, 68:1337-1343, 2005 (hereinafter "Fishbane et al."). More than 90% of the patients experienced hemoglobin cycling. The authors state that changes in ESA dose were the most important driver and were associated with hemoglobin excursion in about 80% of cases. The ESA dose adjustment protocol that was used was similar to the protocol used in most dialysis centers.

Therapy with ESAs is quite different than biological erythropoietin secretion. In hemodialysis patients, i.v. administration route is primarily used, because of the availability of venous access. Intravenous treatment involves short, intermittent, non-physiologic bursts of EPO concentration. The bursts are followed by a fast decline to very low levels of EPO. These fluctuations in plasma concentration do not coincide, either temporally or in magnitude, with physiologic perturbations. Therefore, it may not be surprising that Hb levels fluctuate widely and that it is extremely difficult for physicians to adjust dosing schemes such that no cycling phenomena occur. Note that fluctuations in hemoglobin result in varying oxygen delivery to vital organs. Consequences include repeated episodes of relative ischemia and compensatory mechanisms in organs (e.g., heart) that may result in disordered growth signals, pathologic organ function and worsened patient outcomes. (See Fishbane et al.).

A predictive model of erythropoiesis can help deal with this situation. For instance, a physician can try different ESA treatment regimens and observe their effects on hemoglobin levels over the next few months. Dosing regimens can be tested/chosen with regard to avoidance of neocytolysis, minimal amounts of ESA administered and avoidance of cycling patterns in Hb concentration.

Iron Therapy

Patients with anemia of chronic kidney disease have to be followed for symptoms of iron deficiency. See J. W. Fisher. *Experimental Biology and Medicine*, 28:1-24, 2003. 80-90% of dialysis patients on ESA therapy will require iron at some stage. See R. M. Schaefer and L. Schaefer. *Nephrology Dialysis Transplantation*, 13:9-12, 1998. This very pronounced need for supplementary iron has different reasons. On one hand iron stores can be depleted (absolute iron deficiency). Iron loss in hemodialysis patients (due to continuous gastrointestinal, purpural and gynecological bleeding, frequent blood sampling, surgeries, . . . ) is about 1500-3000 mg/year, as compared to iron loss for a healthy adult that is about 400-800 mg/year, and can be even higher under certain circumstances. Hence, the daily need for iron can be well above the absorptive capacity of the intestinal. This is aggravated by the fact that the uptake via the duodenum is often impaired in these patients. On the other hand, a functional iron deficiency is often observed in renal anemia. During ESA therapy, the number of erythroid progenitor and precursor cells in the bone marrow increase drastically and this imposes a lot of stress on systemic iron homeostasis. Supply and demand often do not match. It is difficult, even for healthy persons, to increase the rate at which iron is released from stores and is recycled from hemoglobin to deliver enough iron to the bone marrow to keep up with supraphysiologic rates of RBC production during ESA treatment. Matters are further complicated in chronic kidney disease because of inflammation, which frequently occurs with various degrees of severity. Thus, iron utilization is regularly decreased in renal insufficiency. See above for a detailed description of the effects of inflammation on systemic iron homeostasis.

In the pre-ESA era iron overload, because of excessive blood transfusions, was a major cause of morbidity in dialysis patients. Its significance in the post-EPO era remains unclear. See K. Kalantar-Zadeh, D. L. Regidor, C. J. McAllister, B. Michael, and Warnock D. G., *Journal of American Society of Nephrology*, 16:3070-3080, 2005. A continuous administration of i.v. iron certainly results in overfilled iron-stores and imposes serious health risks. Hence, decisions on when to supply the patient with i.v. iron and when to withdraw therapy have to be thoroughly evaluated. A mathematical model can help keep track of the current iron status of a patient and can help to make decisions on adaptations of treatment.

Finally, there is a very complex interaction between hemoglobin cycling and iron storage whose dynamical behavior under ESA and iron treatment, even for an experienced physician, is barely predictable. In Alfrey et al., the authors suggest that: "[ . . . ] the current therapeutic paradigm of hemoglobin monitoring, iron treatment, and rHuEPO treatment results in recurrent nonphysiologic cycling of hemoglobin levels in hemodialysis patients."

Computation of Hematocrit and Hemoglobin Concentrations

In order to compute the hematocrit (HCT) and the hemoglobin concentration (Hb) for a subject from the model output (which is the number of red blood cells circulating in blood), estimates of the total blood volume of the subject are needed. The Nadler and Allen formula (see Nadler, S. B., Hidalgo, J. U., and Bloch, T., Surgery, 1962, Vol. 51, pp. 224-232) can be used to estimate the total blood volume (TBV) of a healthy subject according to her/his weight and height:

Women: TBV [ml]=183.3+356.1×(height [m])$^3$+ 33.08×weight [kg],

Men: TBV [ml]=604.1+366.9×(height [m])$^3$+32.19× weight [kg].

The TBV for a dialysis patient can be measured by radio-labeling red blood cells with chromium-51 as described above. Using these estimates for the total blood volume, the hematocrit (HCT) and the hemoglobin concentration (Hb) can be computed for a patient from the number of red blood cells circulating in blood via the following formulae:

$$HCT[\%] = \frac{(M(t) \times MCV[fl])}{TBV[ml]},$$

where $M(t)=\int_0^{\mu_{max}^m} m(t,\mu^m)d\mu^m$ is the total number of erythrocytes circulating in blood and MCV is the mean corpuscular volume of a RBC which is obtained from measurement, and $$Hb\left[\frac{g}{l}\right] = 1000 \times \frac{M(t) \times MCH[pg]}{TBV[ml]},$$

where MCH is the mean cellular hemoglobin, which is also obtained via measurements.

Implementation in a Computer Network

Figure 20:
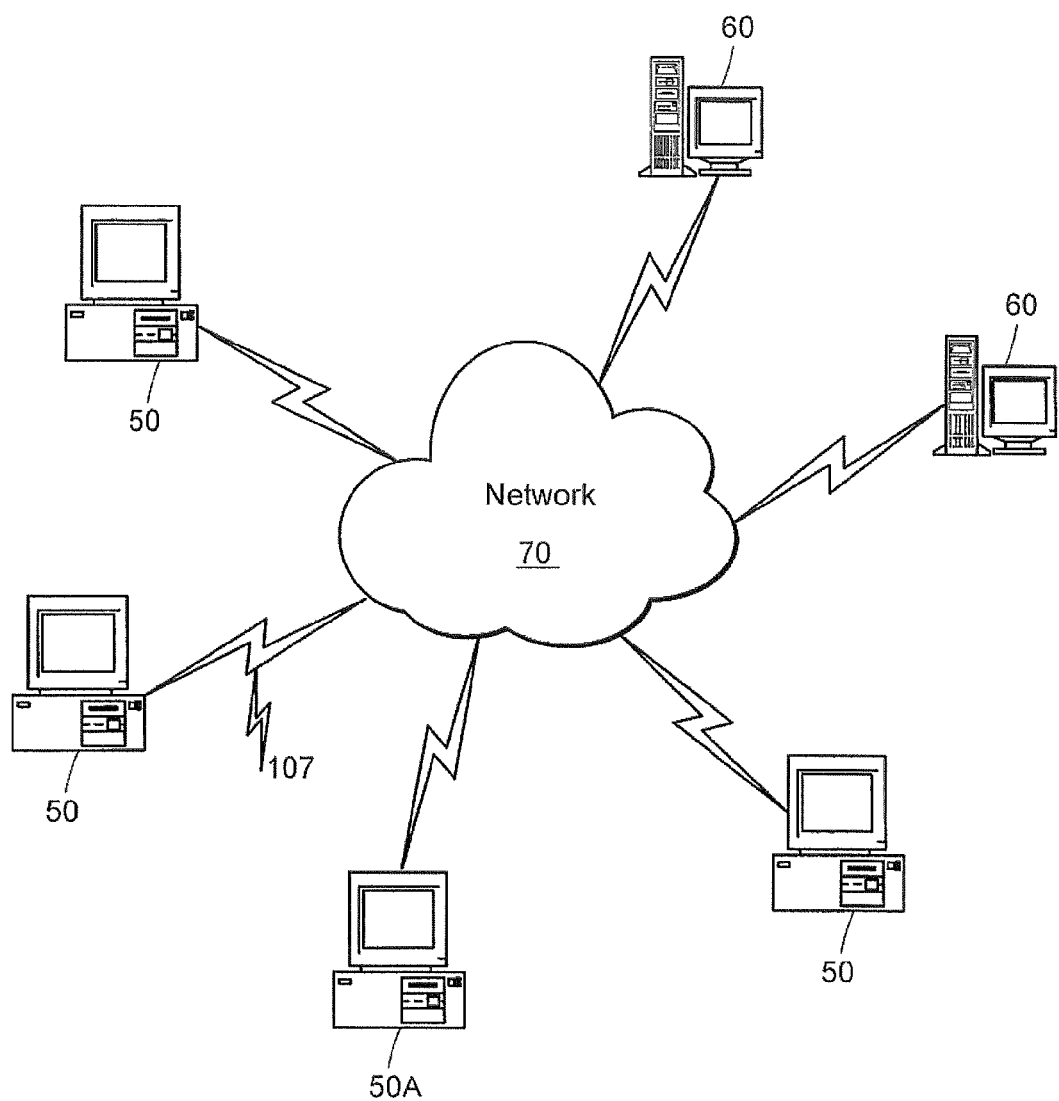
FIG. 20 is a schematic view of a computer network in which the present invention can be implemented.

FIG. 20 illustrates a computer network or similar digital processing environment in which the present invention can be implemented.

Computer(s)/devices 50 and server computer(s) 60 provide processing, storage, and input/output devices executing application programs and the like. Computer(s)/devices 50 can also be linked through communications network 70 to other computing devices, including other devices/processes 50, digital processor dialysis machines 50A, including machines with integrated modular drug delivery devices (as shown in FIGS. 2 and 3), and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 21:
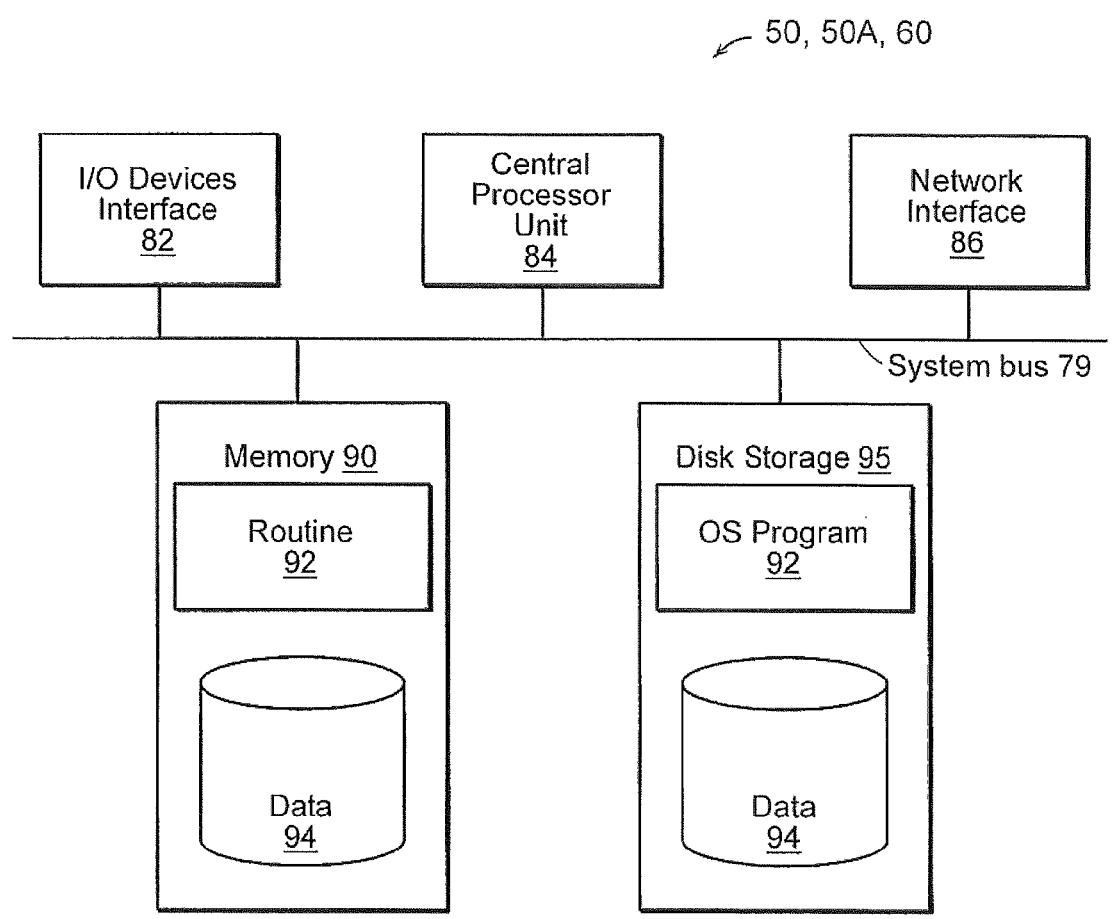
FIG. 21 is a block diagram of a computer of the network of FIG. 20.

FIG. 21 is a diagram of the internal structure of a computer (e.g., processor/device 50, digital processor dialysis machines 50A, or server computers 60) in the computer system of FIG. 20. Each computer 50, 50A, 60 contains a system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements which could be data collected during a treatment, but also instructions to a machine with integrated modular drug delivery devices to follow a drug delivery scheme provided by a central erythropoiesis modeling engine. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 20). Memory 90 provides volatile storage for computer software instructions 92 and data 94 used to implement an embodiment of the present invention (e.g., Eqs. described above and listed in Section 4 or any other erythropoiesis modeling engine detailed above). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the system. Computer program product 92 can be installed by any suitable software installation procedure, as is well known in the art. In another embodiment, at least a portion of the software instructions can also be downloaded over a cable, communication and/or wireless connection. In other embodiments, the programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 can receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

The relevant teachings of all patents, published patent applications and literature references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A hemodialysis system comprising:
a hemodialysis machine comprising
a blood pump;
a modular drug delivery device comprising at least one erythropoiesis stimulating agent (ESA) pump, at least one iron replacement product pump, at least one ESA vial holder, and at least one iron replacement product vial holder; and
a housing to which the blood pump and the modular drug delivery device are secured;
a blood line set comprising multiple blood lines and a drip chamber in fluid communication with the multiple blood lines, at least one of the blood lines being connected to the drip chamber, the blood line set being connected to the blood pump in a manner such that, when the blood line set is connected to a patient and the blood pump is operated, blood of the patient is passed through the blood line set;
a drug administration fluid line set comprising multiple drug lines, at least two of the drug lines of the drug line set being connected to the drip chamber of the blood line set, and the drug line set being connected to the at least one ESA pump and the at least one iron replacement product pump in a manner such that, when the drug line set is fluidly connected to an ESA vial contained in the at least one ESA vial holder and to an iron replacement product vial contained in the at least one iron replacement product vial holder, and the at least one ESA pump and the at least one replacement product pump are operated, ESA and iron replacement product are delivered from the ESA vial and the iron replacement vial, respectively, to the drip chamber of the blood line set via the drug line set; and a control unit comprising a mathematical model of erythropoiesis and iron metabolism and instructions that, when executed, cause the control unit to adjust the patient's undesired hematocrit and/or hemoglobin concentration to a value within a desired range at a predetermined time by i) employing the model to predict the patient's hematocrit and/or hemoglobin concentration at a predetermined time, the model including iron homeostasis, and by ii) operating the blood pump, the at least one ESA pump, and the at least one iron replacement product pump to deliver blood, ESA, and iron replacement product to the drip chamber via the at least one of the blood lines connected to the drip chamber and the at least two of the drug lines connected to the drip chamber, according to an ESA administration regimen predicted to adjust the patient's hematocrit and/or hemoglobin concentration to a value within the desired range at the predetermined time, wherein the mathematical model of erythropoiesis and iron metabolism comprises the functions:

$$\frac{\partial}{\partial t}p(t,\mu^p) + \frac{\partial}{\partial \mu^p}p(t,\mu^p) = \beta^p p(t,\mu^p),$$

$$\frac{\partial}{\partial t}q(t,\mu^q) + \frac{\partial}{\partial \mu^q}q(t,\mu^q) = (\beta^q - \alpha^q(E(t)))q(t,\mu^q),$$

$$\frac{\partial}{\partial t}r(t,\mu^r) + \frac{\partial}{\partial \mu^r}r(t,\mu^r) = \beta^r r(t,\mu^r),$$

$$\frac{\partial}{\partial t}s(t,\mu^s) + v^s(E(t))\frac{\partial}{\partial \mu^s}s(t,\mu^s) = -\alpha^s s(t,\mu^s),$$

$$\frac{\partial}{\partial t}m(t,\mu^m) + \frac{\partial}{\partial \mu^m}m(t,\mu^m) = -\alpha^m(E(t),\mu^m)m(t,\mu^m),$$

$$\frac{d}{dt}E^{end}(t) = \frac{1}{TBV}E_{in}^{end}(t) - c_{deg}^{end}E^{end}(t),$$

$$\frac{d}{dt}E^{ex}(t) = \frac{1}{TBV}E_{in}^{ex}(t) - c_{deg}^{ex}E^{ex}(t),$$

where $$\alpha^q(E(t)) = \frac{a_1 - b_1}{1 + e^{k_1 E(t) - c_1}} + b_1,$$

$$v^s(E(t)) = \frac{a_2 - b_2}{1 + e^{-k_2 E(t) + c_2}} + b_2.$$

and $$\alpha^m(E(t),\mu^m) = \begin{cases} \gamma^m(\mu^m) + \min\left(\frac{c_E}{E(t)^{k_E}}, b_E\right), & for E(t) < \tau_E, \mu_{min}^{m,n} \leq \mu^m \leq \mu_{max}^{m,n}, \\ \gamma^m(\mu^m), & \text{otherwise,} \end{cases}$$

with $$\gamma^m(\mu^m) =$$

-continued $$\begin{cases} \alpha_{rand}^m & \text{for } \mu^m \in [\mu_{min}^m, \mu_{max}^m - \delta], \\ \dfrac{3\alpha_{rand}^m \delta^2}{(\mu^m)^2 - 2(\mu_{max}^m + \delta)\mu^m + (\mu_{max}^m + 2\delta)\mu_{max}^m} & \text{for } \mu^m \in [\mu_{max}^m - \delta, \mu_{max}^m), \\ \infty & \text{for } \mu^m \geq \mu_{max}^m. \end{cases}$$

and $$\frac{d}{dt}a_1(t) = k_{41}(H(t))a_4(t) + a_{iv,total}(t)\delta_{t_0}(t) + k_{gastro,1}(H(t))a_{gastro}(t) + k_{51}(H(t))a_5(t) - k_{15}a_1(t) - d_1\left(\int_{\mu_{min}^r}^{\mu_{max}^r} \varphi(\mu^r)r(t,\mu^r)d\mu^r + \int_{\mu_{min}^s}^{\mu_{max}^s} \varphi(\mu^s)s(t,\mu^s)d\mu^s\right)a_1(t),$$

$$a_2(t) = \int_{\mu_{min}^r}^{\mu_{max}^r} \alpha(h,\mu^r)r(t,\mu^r)d\mu^r + \int_{\mu_{min}^s}^{\eta_{max}^s(t)} \alpha(h,\eta^s)h(t,\eta^s)s\left(t,\mu_{min} + \int_{t-\eta^s}^{t} v(E(s))ds\right)d\eta^s$$

$$a_3(t) = \int_{\mu_{min}^m}^{\mu_{max}^m} h(t-\mu^m, \eta_{max}^s)m(t,\mu^m)d\mu^m$$

$$\frac{d}{dt}a_4(t) = \int_{\mu_{min}^r}^{\mu_{max}^r} \alpha(h,\mu^r)h(t,\mu^r)r(t,\mu^r)d\mu^r + \int_{\mu_{min}^s}^{\eta_{max}^s(t)} \alpha(h,\eta^s)h(t,\eta^s)s\left(t,\mu_{min} + \int_{t-\eta^s}^{t} v(E(s))ds\right)d\eta^s + \int_{\mu_{min}^m}^{\mu_{max}^m} h(t-\mu^m, \eta_{max}^s)\alpha^m(E(t),\mu^m)m(t,\mu^m)d\mu^m - k_{41}(H(t))a_4(t) - k_{45}a_4(t),$$

$$\frac{d}{dt}a_5(t) = k_{15}a_1(t) + k_{45}a_4(t) - k_{51}(H(t))a_5(t),$$

$$\frac{d}{dt}H(t) = \frac{1}{TBV}H_{prod}(t) - c_{deg}^H H(t);$$

wherein TBV is a total blood volume, $p(t,\mu^p)$ is a population density of a BFU-E cell class at time t with maturity $\mu^p$, $\beta^p$ is a proliferation rate for BFU-E cells, $q(t,\mu^q)$ is a population density of a CFU-E cell class at time t with maturity $\mu^q$, $\beta^q$ is a proliferation rate for CFU-E cells, $\alpha^q(E(t))$ is an apoptosis rate for CFU-E cells which depends on erythropoietin (EPO)-concentration $E(t)$ at time t, $r(t,\mu^r)$ is a population density of an erythroblast class at time t with maturity $\mu^r$, $\beta^r$ is a proliferation rate for erythroblasts, $s(t,\mu^s)$ is a population density of a marrow reticulocytes class at time t with maturity $\mu^s$, $v^s(E(t))$ is a maturation velocity of cells leaving the erythroblast class an entering the reticulocytes population class which depends on EPO-concentration $E(t)$ at time t, $\alpha^s$ is an apoptosis rate for marrow reticulocytes, $m(t,\mu^m)$ is a population density of an erythrocyte class at time t with maturity $\mu^m$, $\alpha^m(E(t),\mu^m)$ is an apoptosis rate for erythrocytes which depends on EPO-concentration $E(t)$ at time t and maturity $\mu^m$, $E^{end}(t)$ is an endogenous EPO concentration at time t, $E_{in}^{end}(t)$ is an amount of EPO released by a patient's kidneys, $c_{deg}^{end}$ is a degradation rate of endogenous EPO, $E^{ex}(t)$ is an exogenous EPO concentration at time t, $E_{in}^{ex}(t)$ is an amount of EPO administered to the patient, $c_{deg}^{ex}$ is a degradation rate of exogenous EPO, $a_1$, $b_1$, $c_1$ and $k_1$ are constants for the apoptosis rate for CFU-E cells, $a_2$, $b_2$, $c_2$ and $k_2$ are constants for the maturation velocity for marrow reticulocytes, $\gamma^m(\mu^m)$ is a mortality rate of erythrocytes which depends on maturity $\mu^m$, $b_E$, $c_E$, and $k_E$ are constants in the mortality rate of erythrocytes, $\tau_E$ is a threshold beneath which neocytolysis is triggered, $\mu_{min}^{m,n}$ is a lower bound of erythrocytes which are possibly exposed to neocytolysis, $\mu_{max}^{m,n}$ is an upper bound of erythrocytes which are possibly exposed to neocytolysis, $\alpha_{rand}^m$ is an intrinsic mortality rate for erythrocytes, $\delta_{t_0}(t)$ is a Dirac delta impulse at a time of administration $t_0$, $H(t)$ is a hepcidin concentration and time t, $\alpha_{iv,total}(t)$ is a total amount of iron intravenously administered at time t, $\alpha_{gastro}(t)$ is an amount of iron in the duodenum of the patient at time t, $k_{15}$ is a transfer rate of iron from plasma to storage, $k_{41}$ is a transfer rate of iron from macrophages to plasma, $k_{45}$ is a transfer rate of iron from macrophages to plasma, $k_{51}$ is a transfer rate of iron from storage to plasma, $k_{gastro}$ is a transfer rate of iron in the duodenum of the patient, $a_1(t)$ is a concentration of iron in plasma at time t, $a_2(t)$ is a concentration of iron in a precursor cell compartment at time t, $a_3(t)$ is a concentration of iron in a erythrocyte cell compartment at time t, $a_4(t)$ is a concentration of iron in a macrophage compartment at time t, $a_5(t)$ is a concentration of iron in a storage compartment at time t, $\phi(\mu)$ is a function describing a number of TfR on a cell with cell age $\mu$, $r(t,\mu^r)$ is the density of erythroblasts, $s(t,\mu^s)$ is the density of bone marrow reticulocytes, $h(t,\mu(t))$ denotes an amount of hemoglobin in a cell with age $\mu(t)$ at time t, and $\alpha(h,\eta)$ is a rate of apoptosis of precursor cells with calendric age $\eta$.

2. The hemodialysis system of claim 1, wherein the ESA administration regimen includes iron administration, and the model includes iron homeostasis with iron administration.

3. The hemodialysis system of claim 1, wherein predicting the patient's hematocrit and/or hemoglobin concentration includes modeling influence of iron homeostasis on erythropoiesis.

4. The hemodialysis system of claim 1, wherein the predetermined time is in a range of between about 5 days and about 200 days into the ESA administration regimen.

5. The hemodialysis system of claim 1, wherein the patient undergoes a medical procedure prior, during, or after initiation of the ESA administration regimen, the medical procedure selected from the group consisting of blood donation, surgery, and dialysis, or any combination thereof.

6. The hemodialysis system of claim 1, wherein the patient is a dialysis patient and the desired hematocrit is in the range of between about 28 percent and about 36 percent and the desired hemoglobin concentration is in a range of between about 9.5 g/dL and about 12 g/dL.

* * * * *